(12) United States Patent
Iverson et al.

(10) Patent No.: US 9,901,295 B2
(45) Date of Patent: Feb. 27, 2018

(54) NEAR INFRARED FLUORESCENT SINGLE WALLED CARBON NANOTUBES AS TISSUE LOCALIZABLE BIOSENSORS

(71) Applicant: Massachusetts Institute of Technology, Cambridge, MA (US)

(72) Inventors: Nicole M. Iverson, Boston, MA (US); Michael S. Strano, Lexington, MA (US); Nigel F. Reuel, Cambridge, MA (US); Thomas P. McNicholas, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 301 days.

(21) Appl. No.: 14/488,040

(22) Filed: Sep. 16, 2014

(65) Prior Publication Data

US 2015/0133752 A1    May 14, 2015

Related U.S. Application Data

(60) Provisional application No. 61/878,303, filed on Sep. 16, 2013.

(51) Int. Cl.

| A61B 5/1455 | (2006.01) |
|---|---|
| A61B 5/1459 | (2006.01) |
| B82Y 15/00 | (2011.01) |
| B82Y 30/00 | (2011.01) |
| A61B 5/145 | (2006.01) |
| G01N 21/64 | (2006.01) |
| G01N 21/77 | (2006.01) |

(52) U.S. Cl.
CPC ........ *A61B 5/14556* (2013.01); *A61B 5/1459* (2013.01); *A61B 5/14552* (2013.01); *B82Y 15/00* (2013.01); *B82Y 30/00* (2013.01); *A61B 5/14532* (2013.01); *A61B 2562/0285* (2013.01); *A61B 2562/12* (2013.01); *G01N 2021/6432* (2013.01); *G01N 2021/7723* (2013.01); *G01N 2021/7786* (2013.01)

(58) Field of Classification Search
None
See application file for complete search history.

(56) References Cited

U.S. PATENT DOCUMENTS

| 5,114,676 A | 5/1992 | Leiner et al. |
|---|---|---|
| 2005/0037512 A1 | 2/2005 | Yeh et al. |
| 2006/0009409 A1 | 1/2006 | Woolf |
| 2007/0125181 A1 | 6/2007 | Ofek et al. |
| 2011/0045523 A1 | 2/2011 | Strano et al. |

OTHER PUBLICATIONS

Notification Concerning Transmittal of International Preliminary Report on Patentability (Chapter I of The Patent Cooperation Treaty) dated Dec. 22, 2014, issued in International Application No. PCT/US2014/055911.
International Search Report dated Dec. 22, 2014, issued in International Application No. PCT/US2014/055911.
Written Opinion of the International Searching Authority dated Dec. 22, 2014, issued in International Application No. PCT/US2014/055911.

*Primary Examiner* — Eric Winakur
*Assistant Examiner* — Marjan Fardanesh
(74) *Attorney, Agent, or Firm* — Steptoe & Johnson LLP

(57) ABSTRACT

A nanosensor for detecting an analyte can include a substrate, a photoluminescent nanostructure, and a polymer interacting with the photoluminescent nanostructure. The nanosensor can be used in in vivo for biomedical applications.

43 Claims, 37 Drawing Sheets

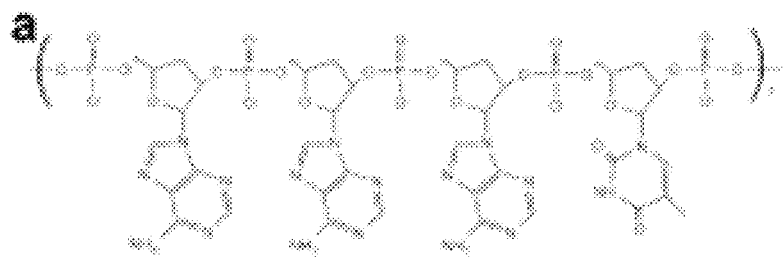
FIG. 1A
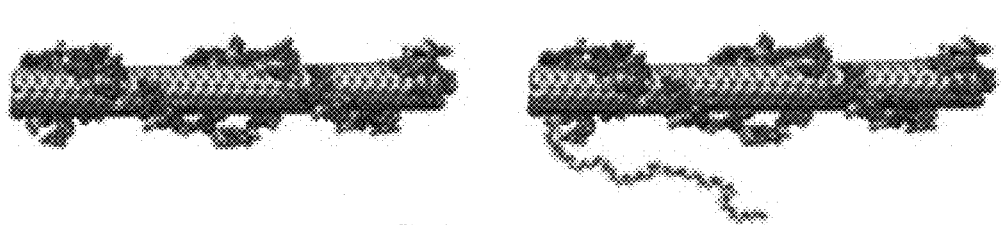
FIG. 1B
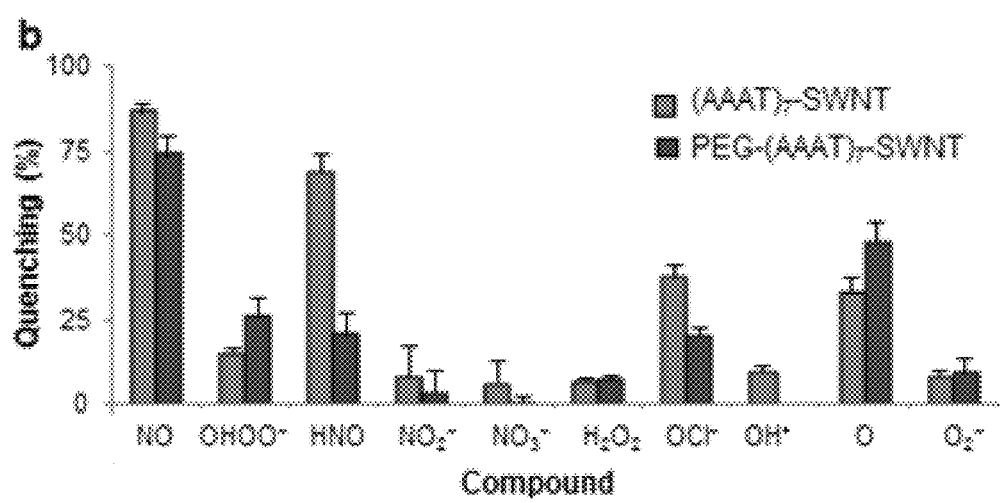

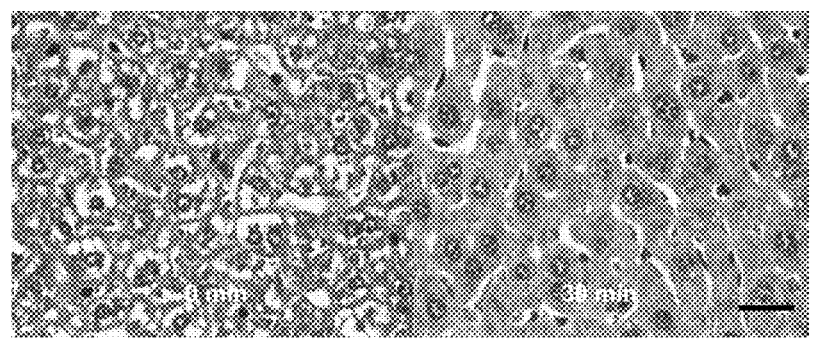
FIG. 3A
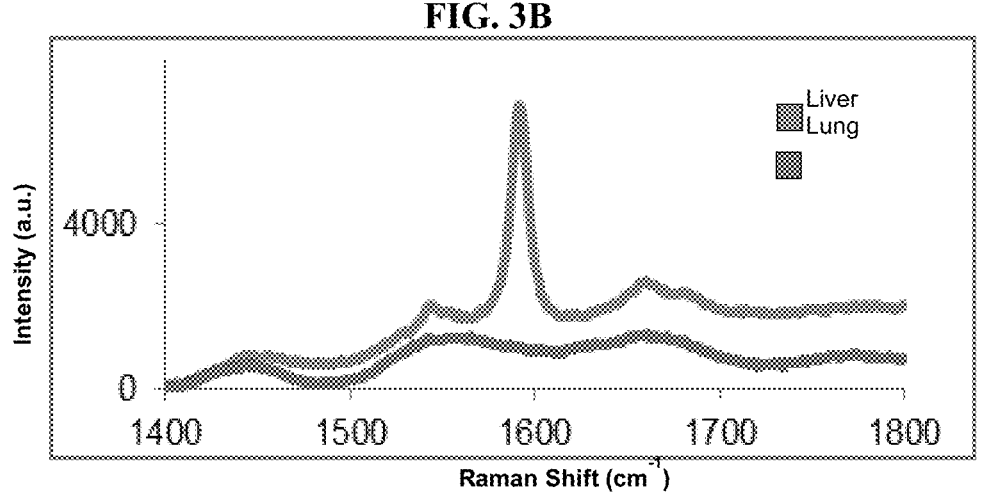
FIG. 3B
FIG. 3C

Day 4        Day 180        Day 400

1: Control DNA
2: 5kDa PEG-(AAAT)$_7$

NEAR INFRARED FLUORESCENT SINGLE WALLED CARBON NANOTUBES AS TISSUE LOCALIZABLE BIOSENSORS

CLAIM OF PRIORITY

This application claims priority to U.S. Patent Application No. 61/878,303, filed Sep. 16, 2013, which is incorporated by reference in its entirety.

FEDERALLY SPONSORED RESEARCH OR DEVELOPMENT

This invention was made with government support under Grant No. ES007020, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 13, 2015, is named 14952.0460_SL.txt and is 1,106 bytes in size.

TECHNICAL FIELD

The invention features systems and methods related to optical nanosensors including photoluminescent nanostructures.

BACKGROUND

Small molecules can play roles as intracellular messengers for signaling pathways within the human body. For example, nitric oxide (NO) can participate in signaling in the cardiovascular and nervous systems, and can be employed in the human immune response system. Detection of small molecules has traditionally been relatively difficult, and becomes even more difficult at low concentrations. Examples of tools that may be used to detect such species include, for example, visible-fluorescence probes, chemiluminescence-based devices, and X-ray photoelectron and electron paramagnetic resonance (EPR) spectroscopy. For example, in the case of NO, a series of diaminofluoresceins and metal-fluorophore complexes have been widely applied to detect cellular NO. However, such methods may include significant limitations. For example, diaminofluoresceins generally detect molecules indirectly (e.g., via oxidation products). Other limitations include photobleaching and lack of optical penetration through biological tissues for metal-fluorophore complexes. Therefore, the design of more robust schemes for the biological detection of relatively small molecules is still an active area of research. Nanotechnology has produced several new classes of biosensors, but their extension to in vivo application has been limited.

SUMMARY

In general, a nanosensor for detecting an analyte can include a substrate hydrogel arranged on a support, a sensor hydrogel arranged on the substrate hydrogel, a photoluminescent nanostructure embedded in the sensor hydrogel, and a polymer interacting with the photoluminescent nanostructure.

The analyte can have a molecule weight of less than 100 g/mol. For example, the analyte can be nitric oxide. The concentration of the analyte can be less than 1 micromolar.

The photoluminescent nanostructure of the nanosensor can include a carbon nanotube. The carbon nanotube can be a single-walled carbon nanotube. In one embodiment, the single-walled carbon nanotube can be a semiconductive single-walled carbon nanotube. The photoluminescent nanostructure can emit near-infrared radiation either in the absence of the analyte, or in the presence of the analyte.

The polymer of the nanosensor can include an oligonucleotide or a polynucleotide. In one embodiment, the oligonucleotide can include $ds(AAAT)_7$ (SEQ ID NO: 1). In another embodiment, the polymer can include polyvinyl alcohol, poly(acrylic acid), poly(ethylene oxide), poly(vinyl pyrrolidinone), poly(allyl amine), poly(2-vinylpyridine), or poly(maleic acid). In yet another embodiment, the polymer can include a copolymer of a hydrophilic polymer and an oligonucleotide, where the hydrophilic polymer can be poly(ethylene oxide) and the oligonucleotide can be $ds(AAAT)_7$ (SEQ ID NO: 1). The copolymer can be formed with poly(ethylene oxide) and $ds(AAAT)_7$ (SEQ ID NO: 1).

In one aspect, a method of detecting an analyte in a subject can include introducing a sensor into a subject, where the sensor include a substrate hydrogel arranged on a support, a sensor hydrogel arranged on the substrate hydrogel, a photoluminescent nanostructure embedded in the sensor hydrogel, a polymer interacting with the photoluminescent nanostructure, and monitoring emission of radiation from the sensor in the subject. In one embodiment, the method of detecting an analyte further include detecting photoluminescence from the photoluminescent nanostructure. The sensor can be introduced into a subject by injecting the sensor into a tissue of the subject.

In another aspect, a method of making a sensor for detecting an analyte can include arranging a substrate hydrogel on a support, casting a sensor hydrogel from a sensor hydrogel precursor composition on the substrate hydrogel, where the sensor hydrogel precursor composition includes a photoluminescent nanostructure in the sensor hydrogel, and a polymer interacting with the photoluminescent nanostructure.

In another aspect, a nanosensor for detecting an analyte can include a photoluminescent nanostructure in a liquid medium, and a housing with pores, where the photoluminescent nanostructure is contained in the housing and transported through the pores.

In another aspect, a method of detecting an analyte in a subject can include introducing a sensor into a subject, where the sensor includes a photoluminescent nanostructure in a liquid medium and a housing with pores, wherein the photoluminescent nanostructure is contained in the housing and transported through the pores, and monitoring emission of radiation from the sensor in the subject.

Other aspects, embodiments, and features will be apparent from the following description, the drawings, and the claims.

BRIEF DESCRIPTION OF THE DRAWINGS

FIGS. 1A-1D depict characterization and 2Dλ imaging analysis of DNA wrapped SWNT complexes. FIG. 1A shows chemical composition of complex with $d(AAAT)_7$ (SEQ ID NO: 1) and wrapped $(AAAT)_7$-SWNT (SEQ ID NO: 1) and PEG-$(AAAT)_7$-SWNT (SEQ ID NO: 1). FIGS. 1B-1C are graphs depicting quenching activity of $(AAAT)_7$-SWNT (SEQ ID NO: 1) (red) and PEG-(AA AT)$_7$-SWNT (SEQ ID NO: 1) (blue) sensors quantified by percent quenching of original fluorescence following exposure to RNS and ROS compounds (FIG. 1B) and NO (FIG. 1C). FIG. 1D is an imaging analysis for (AAAT)$_7$-SWNT (SEQ ID NO: 1) in an excised mouse liver after a tail vein injection of PEG-(AAAT)$_7$-SWNT (SEQ ID NO: 1).

FIG. 2A is an image depicting (AAAT)$_7$-SWNT (SEQ ID NO: 1) remaining within the tail following injection into left then right tail veins. FIG. 2B is a graph depicting gel electrophoresis data showing the difference in electrophoretic mobility of (AAAT)$_7$-SWNT (SEQ ID NO: 1) (red) when mixed with FBS as opposed to PEG-(AAAT)$_7$-SWNT (SEQ ID NO: 1) (blue) which was not altered by the addition of FBS. FIG. 2C is an image depicting mouse tail following injection of PEG-(AAAT)$_7$-SWNT (SEQ ID NO: 1) into the left tail vein.

FIGS. 3A-3G depict biodistribution and biocompatibility of PEG-(AAAT)$_7$-SWNT (SEQ ID NO: 1) in mice (specific strain 129X1/SvJ). Data from mice sacrificed at various time points following tail vein injection of PEG-(AAAT)$_7$-SWNT (SEQ ID NO: 1). FIG. 3A is a set of histology images (H&E staining) of liver tissue sections for a control mouse and a mouse that received PEG-(AAAT)$_7$-SWNT (SEQ ID NO: 1). FIG. 3B is a table representing SWNT presence (+) or absence (−) in blood, tail (site of injection), lung, liver, kidney and urine following sacrifice and excision. FIG. 3C is a graph depicting representative Raman spectrum of those used to determine SWNT localization in FIG. 3B. FIG. 3D is a series of images of excised livers deconvoluted with 2Dλ technology. FIG. 3E is a graph depicting quantification of SWNT fluorescence in mouse livers excised at various time points following tail vein injection PEG-(AAAT)$_7$-SWNT (SEQ ID NO: 1). FIG. 3F is a graph depicting SWNT fluorescence distribution in mouse livers shown in FIG. 3E. FIG. 3G is a graph depicting a mathematical model of PEG-(AAAT)$_7$-SWNT (SEQ ID NO: 1) concentration in mouse liver over time.

FIG. 4A is a series of images depicting inflamed (RcsX treated) and healthy (control) mice imaged after tail vein injection of PEG-(AAAT)$_7$-SWNT (SEQ ID NO: 1) with their livers exposed then immediately following sacrifice. FIG. 4B is a graph depicting quantification of SWNT fluorescence. FIG. 4C is a graph depicting SWNT fluorescence distribution in mouse livers shown in FIGS. 4A-4B.

FIGS. 5A-5B are graphs depicting quenching activity of (AAAT)$_7$-SWNT (SEQ ID NO: 1) (red) and Alginate-(AAAT)$_7$-SWNT (SEQ ID NO: 1) (green) sensors following exposure to RNS and ROS compounds (FIG. 5A) and NO (FIG. 5B). FIG. 5C is images of mouse following implantation of two Alginate-(AAAT)$_7$-SWNT (SEQ ID NO: 1) gels on day 0 (immediately after implantation of gel 2) and on day 4 after the fluorescence has returned. FIG. 5D is a series of images of Alginate-(AAAT)$_7$-SWNT (SEQ ID NO: 1) gel prior to subcutaneous implantation and at various time points. FIG. 5E is a graph depicting quantification of peak SWNT fluorescence for one of the mice tested displaying long term consistency of SWNT signal. FIG. 5F is a series of histology images (H&E staining) from mice sacrificed at three different time points following the subcutaneous implantation of Alginate-(AAAT)$_7$-SWNT (SEQ ID NO: 1).

FIG. 17A is strain sweep of alginate. FIG. 17B is PEG gels with constant 1 Hz frequency. FIGS. 17C and 17D is frequency sweep of alginate gels under 0.1% strain (FIG. 17C) and of PEG gels under 0.01% strain (FIG. 17D).

DETAILED DESCRIPTION

Figure 1C:
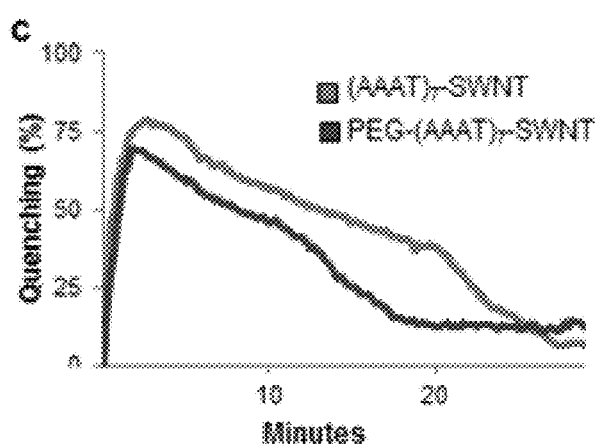

The near infrared region of the electromagnetic spectrum has advantages for in vivo fluorescence imaging, due to minimal auto fluorescence and absorption of blood and tissue. See, Frangioni, J. V. In vivo near-infrared fluorescence imaging. *Curr Opin Chem Biol* 7, 626-634 (2003), and Wray, S., Cope, M., Delpy, D., Wyatt, J. & Reynolds, E. Characterization of the near infrared absorption spectra of cytochrome aa3 and haemoglobin for the non-invasive monitoring of cerebral oxygenation. *Biochimica et Biophysica Acta* 933, 184-192 (1988), each of which is incorporated by reference in its entirety. Common nIR fluorescent agents include organic nIR fluorophores, such as Indocyanine green (ICG), semiconductor quantum dots (Qdots), and single-walled carbon nanotubes (SWNT). The ICG dye was utilized for real time detection of liver cancer, and sentinel lymph node mapping in breast cancer patient. Biofunctionalized CdSe/ZnS Qdots and InAs/InP/ZnSe Qdots were used for tumor targeting and fluorescent imaging in mice. See, Schaafsma, B. E. et al. The clinical use of indocyanine green as a near-infrared fluorescent contrast agent for image-guided oncologic surgery. *Journal of Surgical Oncology* 104, 323-332, doi:10.1002/jso.21943 (2011), Michalet, X. et al. Quantum dots for live cells, in vivo imaging, and diagnostics. *Science* 307, 538-544, doi:10.1126/science.1104274 (2005), Medintz, I. L., Uyeda, H. T., Goldman, E. R. & Mattoussi, H. Quantum dot bioconjugates for imaging, labelling and sensing. *Nat Mater* 4, 435-446, doi:10.1038/nmat1390 (2005), Pinaud, F. et al. Advances in fluorescence imaging with quantum dot bio-probes. *Biomaterials* 27, 1679-1687, doi:10.1016/j.biomaterials.2005.11.018 (2006), Bachilo, S. M. et al. Structure-Assigned Optical Spectra of Single-Walled Carbon Nanotubes. *Science* 298, 2361-2366, doi:10.1126/science.1078727 (2002), Ishizawa, T. et al. Real-time identification of liver cancers by using indocyanine green fluorescent imaging. *Cancer* 115, 2491-2504, doi:10.1002/cncr.24291 (2009), Troyan, S. L. et al. The FLARE intraoperative near-infrared fluorescence imaging system: a first-in-human clinical trial in breast cancer sentinel lymph node mapping. *Ann Surg Oncol* 16, 2943-2952, doi:10.1245/s10434-009-0594-2 (2009), Gao, X., Cui, Y., Levenson, R. M., Chung, L. W. & Nie, S. In vivo cancer targeting and imaging with semiconductor quantum dots. *Nat Biotechnol* 22, 969-976, doi:10.1038/nbt994 (2004), and Gao, J. et al. In Vivo Tumor-Targeted Fluorescence Imaging Using Near-Infrared Non-Cadmium Quantum Dots. *Bioconjugate Chemistry* 21, 604-609, doi:10.1021/bc900323v (2010), each of which is incorporated by reference in its entirety. Moreover, nIR fluorescent phosphine coated CdTe/CdSe Qdots, which were intradermally injected into mice and pigs, were utilized for sentinel lymph node mapping. See, Kim, S. et al. Near-infrared fluorescent type II quantum dots for sentinel lymph node mapping. *Nat Biotechnol* 22, 93-97, doi:10.1038/nbt920 (2004), which is incorporated by reference in its entirety. These demonstrations exploited the first nIR window (<950 nm), however, the second nIR window (950-1400 nm) benefits from further reduced autofluorescence and lower photon scattering, even though water absorption is higher. See, Yi, H. et al. M13 Phage-Functionalized Single-Walled Carbon Nanotubes As Nanoprobes for Second Near-Infrared Window Fluorescence Imaging of Targeted Tumors. *Nano Lett* 12, 1176-1183, doi:10.1021/nl2031663 (2012), and Welsher, K. et al. A route to brightly fluorescent carbon nanotubes for near-infrared imaging in mice. *Nature Nanotechnology* 4, 773-780 (2009), each of which is incorporated by reference in its entirety. Although the properties of quantum dots can be altered to tune their emission peak to longer wavelengths, the availability of inorganic precursors and their toxicity is still a constraint. See, Ma, Q. & Su, X. Near-infrared quantum dots: synthesis, functionalization and analytical applications. *Analyst* 135, 1867-1877, doi:10.1039/cOan00233j (2010), and Rogach, A. L., Eychmüller, A., Hickey, S. G. & Kershaw, S. V. Infrared-Emitting Colloidal Nanocrystals: Synthesis, Assembly, Spectroscopy, and Applications. *Small* 3, 536-557, doi:10.1002/smll.200600625 (2007), each of which is incorporated by reference in its entirety.

Single walled carbon nanotubes have great potential for biomedical applications due to their unique optical properties and their ability to fluoresce in the nIR range of 900-1400 nm. Moreover, they are preferable in vivo imaging agents as they can be rendered biocompatible with proper surface wrapping, and due to their lack of photobleaching, as opposed to organic dyes and Qdots. See, Schipper, M. L. et al. A pilot toxicology study of single-walled carbon nanotubes in a small sample of mice. *Nature nanotechnology* 3, 216-221 (2008), Liu, Z., Tabakman, S., Welsher, K. & Dai, H. Carbon Nanotubes in Biology and Medicine: In vitro and in vivo Detection, Imaging and Drug Delivery. *Nano Research* 2, 85-120 (2009), Cherukuri, P., Bachilo, S. M., Litovsky, S. H. & Weisman, R. B. Near-infrared fluorescence microscopy of single-walled carbon nanotubes in phagocytic cells. *Journal of the American Chemical Society* 126, 15638-15639 (2004), Graff, R. A. et al. Achieving individual-nanotube dispersion at high loading in single-walled carbon nanotube composites. *Advanced Materials* 17, 980-984 (2005), and Barone, P. W., Parker, R. S. & Strano, M. S. In vivo fluorescence detection of glucose using a single-walled carbon nanotube optical sensor: Design, fluorophore properties, advantages, and disadvantages. *Analytical Chemistry* 77, 7556-7562 (2005), each of which is incorporated by reference in its entirety. First demonstration of SWNT imaging within a living organism was manifested in *Drosophila melanogaster*, which was fed SWNT suspended in bovine serum albumin (BSA) solution. See, Leeuw, T. K. et al. Single-walled carbon nanotubes in the intact organism: near-IR imaging and biocompatibility studies in *Drosophila. Nano Lett* 7, 2650-2654, doi:10.1021/n10710452 (2007), which is incorporated by reference in its entirety. Polyethylene glycol (PEG) coated SWNT, which are biocompatible, were fluorescently imaged in mice following tail vein injection, apparently localized in the liver and spleen, which play a role in excretion foreign objects from the body. The circulation time of SWNT in mice was found to be of the order of 1 day, where total clearance can take 2 months. See, Liu, Z. et al. Circulation and long-term fate of functionalized, biocompatible single-walled carbon nanotubes in mice probed by Raman spectroscopy. *Proceedings of the National Academy of Sciences* 105, 1410 (2008), which is incorporated by reference in its entirety.

An additional advantage of SWNT is that tailored functionalization of the nanotube's surface can result in a selective fluorescent modulation upon the interaction with a specific analyte, rendering the SWNT an optical sensor. See, Barone, P. W., Bak S., Heller, D. A. & Strano, M. S, Near-infrared optical sensors based on single-walled carbon nanotubes. *Nat Mater* 4,86-U16 (2005), Kruss, S. et al. Carbon nanotubes as optical biomedical sensors. *Advanced Drug Delivery Reviews* 65, 1933-1950 (2013), and Zhang, J. et al. Molecular recognition using a corona complex made of artificial polymers adsorbed on carbon nanotubes. *Nature Nanotechnology* 8, 959-968 (2013), each of which is incorporated by reference in its entirety. However, in vivo localization of the SWNT in a region of interest and the stability of the signal once the SWNT are delivered are of crucial importance for any imaging application. One possibility to minimize variation in SWNT localization is to encapsulate the nanoparticles within a biocompatible hydrogel that can be implanted within the animal. See, Iverson, N. M. et al. In Vivo Biosensing Via Tissue Localizable Near Infrared Fluorescent Single Walled Carbon Nanotubes. *Nature Nanotechnology* 8, 873-880 (2013), which is incorporated by reference in its entirety.

Single-walled carbon nanotubes as optical sensors are photostable and fluoresce in the near-infrared (n-IR), where blood and tissue absorption and autofluorescence is minimal. See, Wray, S., Cope, M., Delpy, D., Wyatt, J. & Reynolds, E. Characterization of the near infrared absorption spectra of cytochrome aa3 and haemoglobin for the non-invasive monitoring of cerebral oxygenation. *Biochimica et Biophysica Acta* 933, 184-192 (1988), which is incorporated by reference in its entirety. SWNT have demonstrated single-molecule sensitivity, and can be functionalized to selectively detect a variety of molecules (see Heller, D. A. et al. Multimodal optical sensing and analyte specificity using single-walled carbon nanotubes. *Nature Nanotechnology* 4, 114-120 (2009), which is incorporated by reference in its entirety), including alkylating chemotherapeutic drugs, hydrogen peroxide (see Jin, H., Heller, D. A., Kim, J. H. & Strano, M. S. Stochastic Analysis of Stepwise Fluorescence Quenching Reactions on Single-Walled Carbon Nanotubes: Single Molecule Sensors. *Nano Letters* 8, 4299-4304 (2008), and Jin, H. et al. Detection of single-molecule H2O2 signalling from epidermal growth factor receptor using fluorescent single-walled carbon nanotubes. *Nature Nanotechnology* 5, 302-309 (2010), each of which is incorporated by reference in its entirety) and NO (see Kim, J. H. et al. The rational design of nitric oxide selectivity in single-walled carbon nanotube near-infrared fluorescence sensors for biological detection. *Nature Chemistry* 1, 473-481 (2009), and Zhang, J. Q. et al. Single Molecule Detection of Nitric Oxide Enabled by d(AT)(15) (SEQ ID NO: 3) DNA Adsorbed to Near Infrared Fluorescent Single-Walled Carbon Nanotubes. *Journal of the American Chemical Society* 133, 567-581 (2011), each of which is incorporated by reference in its entirety). SWNT have been functionalized for biocompatibility, demonstrating long circulation times (Liu, X. et al. Optimization of surface chemistry on single-walled carbon nanotubes for in vivo photothermal ablation of tumors. *Biomaterials* 32, 144-151 (2011), Liu, Z. et al. In vivo biodistribution and highly efficient tumour targeting of carbon nanotubes in mice. *Nature Nanotechnology* 2, 47-52 (2007), Liu, Z. et al. Drug delivery with carbon nanotubes for in vivo cancer treatment. *Cancer Research* 68, 6652 (2008), Liu, Z. et al. Circulation and long-term fate of functionalized, biocompatible single-walled carbon nanotubes in mice probed by Raman spectroscopy. *Proceedings of the National Academy of Sciences* 105, 1410 (2008), and Liu, Z. et al. Supramolecular stacking of doxorubicin on carbon nanotubes for in vivo cancer therapy. *Angewandte Chemie International Edition* 48, 7668-7672 (2009), each of which is incorporated by reference in its entirety), favorable biodistribution in several mammalian animal models (see Cherukuri, P. et al. Mammalian pharmacokinetics of carbon nanotubes using intrinsic near-infrared fluorescence. *Proceedings of the National Academy of Sciences* 103, 18882-18886 (2006), and Singh, R. et al. Tissue biodistribution and blood clearance rates of intravenously administered carbon nanotube radiotracers. *Proceedings of the National Academy of Sciences of the United States of America* 103, 3357-3362 (2006), each of which is incorporated by reference in its entirety) and highly favorably toxicological profiles for in vivo utility. See, Liu, Z., Tabakman, S., Welsher, K. & Dai, H. Carbon nanotubes in biology and medicine: In vitro and in vivo detection, imaging and drug delivery. *Nano Research* 2, 85-120 (2009), Liu, Z., Tabakman, S. M., Chen, Z. & Dai, H. Preparation of carbon nanotube bioconjugates for biomedical applications. *Nature protocols* 4, 1372-1381 (2009), Robinson, J. T. et al. High performance in vivo near-IR (>1 μm) imaging and photothermal cancer therapy with carbon nanotubes. *Nano Research* 3, 779-793 (2010), Sato, Y. et al. Influence of length on cytotoxicity of multi-walled carbon nanotubes against human acute monocytic leukemia cell line THP-1 in vitro and subcutaneous tissue of rats in vivo. *Molecular BioSystems* 1, 176-182 (2005), Schipper, M. L. et al. A pilot toxicology study of single-walled carbon nanotubes in a small sample of mice. *Nature nanotechnology* 3, 216-221 (2008), and Welsher, K. et al. A route to brightly fluorescent carbon nanotubes for near-infrared imaging in mice. *Nature Nanotechnology* 4, 773-780 (2009), each of which is incorporated by reference in its entirety. Proposed in vivo uses of SWNT include image contrast agents for bioimaging and drug delivery agents, however their use as diagnostic sensors has not yet been demonstrated in vivo. Such use requires a synthetic strategy that incorporates biocompatibility, molecular recognition, high quantum efficiency and optical transduction of analyte binding.

These constraints are addressed by demonstrating the synthesis and operation of a complex that allows for analyte detection from within complex tissues and organs in vivo. In some cases, nanosensors may be useful in determining relatively small analytes. For example, in some embodiments, the analyte can have a molecular weight of about 1000 g/mol or less, about 500 g/mol or less, about 100 g/mol or less, or about 30 g/mol or less. For example, the nanosensors can be used to determine nitric oxide, which has a molecular weight of about 30 g/mol. Exemplary analytes that can be determined using the systems and methods described herein include, for example, nitric oxide, hydrogen peroxide, hydroxyl radical, glutamate, aspartate, serine, g-aminobutyric acid, glycine, dopamine, norepinephrine, epinephrine, serotonin, melatonin, acetylcholine, adenosine, anandamide, histamine, and the like.

In some embodiments, the systems and methods described herein may be capable of determining relatively low concentrations of an analyte. The ability to determine low concentrations of an analyte may be useful, for example, in detecting trace pollutants or trace amounts of toxins within a subject. In some embodiments, nanosensors can determine analyte concentrations of less than about 100 micromolar, less than about 10 micromolar, less than about 1 micromolar, less than about 100 nanomolar, less than about 10 nanomolar, or less than about 1 nanomolar. In some cases, nanosensors can be used to determine a single molecule of an analyte.

The in vivo detection of nitric oxide (NO) is utilized as a model since it is a free-radical involved in diverse biological processes, such as apoptosis, neurotransmission, blood pressure control and innate immunity (see Moncada, S., Palmer, R. M. & Higgs, E. A. Nitric oxide: physiology, pathophysiology, and pharmacology. *Pharmacology Review* 43, 109-142 (1991), which is incorporated by reference in its entirety) and has not been probed in intraperitoneal tissues. Current technology allows for in vivo NO detection through an electrochemical probe surgically implanted in a rat's brain (see Park, S. S. et al. Real-Time in Vivo Simultaneous Measurements of Nitric Oxide and Oxygen Using an Amperometric Dual Microsensor. *Analytical Chemistry* 82, 7618-7624 (2010), which is incorporated by reference in its entirety), but does not permit long term or non-invasive NO detection. Of critical importance to NO function is its steady-state concentration in tissues, with biologically relevant concentrations ranging over three orders-of-magnitude. On the basis of literature estimates, Thomas et al. proposed the following concentration categories for NO functions: (a) GMP-mediated signaling processes at 1-30 nM; (b) modulation of kinase and transcription factor activity at 30-400 nM; and (c) pathological nitrosative and oxidative stresses above 500 nM. See, Thomas, D. D. et al. The chemical biology of nitric oxide: implications in cellular signaling. *Free Radical Biology and Medicine* 45, 18-31 (2008), which is incorporated by reference in its entirety. Activated macrophages are the major source of pathologically high levels of NO (see Lewis, R. S., Tamir, S., Tannenbaum, S. R. & Deen, W. M. Kinetic analysis of the fate of nitric oxide synthesized by macrophages in vitro. *The Journal of Biological Chemistry* 270, 29350-29355 (1995), which is incorporated by reference in its entirety), producing local steady-state concentrations approaching 1 µM (see, Dedon, P. C. & Tannenbaum, S. R. Reactive nitrogen species in the chemical biology of inflammation. *Archives of Biochemistry and Biophysics* 423, 12-22 (2004), which is incorporated by reference in its entirety). NO rapidly reacts with superoxide anion ($O_2.^-$) to form peroxynitrite ($ONOO^-$), a potent oxidant. peroxynitrite further reacts with $CO_2$ to form nitrosoperoxycarbonate ($ONOOOCOO^-$), which decomposes into nitrogen dioxide ($NO_2.$) and carbonate radical ($CO_3.^-$), which are also very strong oxidants. Overproduction of these reactive species in chronic inflammation can cause damage to all types of cellular biomolecules and thus contribute to the mechanistic link between inflammation and diseases such as cancer. See, Coussens, L. M. & Werb, Z. Inflammation and cancer. *Nature* 420, 860-867 (2002), which is incorporated by reference in its entirety.

A variety of polymers may be used in association with the embodiments described herein. In some embodiments, the polymer may include a polysaccharide such as, for example, dextran, amylose, chitin, or cellulose. In some embodiments, the polymer may include a protein. Examples of suitable proteins include, but are not limited to glucose oxidase, bovine serum albumin and alcohol dehydrogenase. The polymer may include a synthetic polymer (e.g., polyvinyl alcohol, poly(acrylic acid), poly(ethylene oxide), poly(vinyl pyrrolidinone), poly(allyl amine), poly(2-vinylpyridine), poly(maleic acid), and the like), in some embodiments. In some embodiments, the polymer may comprise a polynucleotide or oligonucleotide. For example, the polymer may comprise a series of repeated base pairs (e.g., repeated adenine-thymine (AT) base pairs, repeated guanine-thymine (GT) base pairs, etc.), repeated base triplets (e.g., AAA, CCC, TTT, GGG, etc.), or repeated base quartets (e.g., AAAT, TTTA, CCCA, GGGA, AAAC, AAAG, TTTC, TTTG, GGGC, or GGGC, etc.). Each repeat can be present two, three, four, five, six, seven, eight, nine or ten times in a row in the oligonucleotide or polynucleotide. In some embodiments, the polymer may comprise at least about 5, at least about 15, at least about 25, at least about 50, or at least about 100, between 5 and 30, or between 10 and 20, or about 15 repeated base pairs (e.g., AT, GT, and the like) in succession. In certain embodiments, the polymer can include an oligonucleotide conjugated to synthetic polymer.

In another aspect, methods for sensing an analyte using nanosensors including photoluminescent nanostructures are provided. The method can comprise providing a photoluminescent nanosensor including a photoluminescent nanostructure and a polymer that interacts with the photoluminescent nanostructure. The polymer may interact with the photoluminescent nanostructure, for example, via any of the mechanisms described above. The method may further comprise exposing the photoluminescent nanosensor to a composition containing an analyte (e.g., any of the analytes described above including, for example, nitric oxide). The method may also comprise determining the analyte based upon the interaction between the analyte and the photoluminescent nanosensor. In some embodiments, the method may comprise determining an analyte with a relatively low molecular weight (e.g., about 1000 g/mol or less, about 500 g/mol or less, about 100 g/mol or less, or about 30 g/mol or less). In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte).

In general, a sensor can include a hydrogel and a photoluminescent nanostructure. In one aspect, a sensor for detecting an analyte can include a substrate hydrogel arranged on a support, a sensor hydrogel arranged on the substrate hydrogel, a photoluminescent nanostructure embedded in the sensor hydrogel, a polymer interacting with the photoluminescent nanostructure. A sensor can include a support which supports substrate hydrogel, which in turn supports sensor hydrogel. Sensor hydrogel can include hydrogel network, photoluminescent nanostructures and associated linking polymers, optional crosslinks between linking polymers, and a polymer interacting with the photoluminescent nanostructure. Sensor hydrogel will typically be formed in the absence of analyte, and analyte may be contacted with sensor hydrogel after formation. Thus in some states, sensor gel is free of analyte and in other states includes analyte (e.g., associated with analyte-binding compound). The presence of the analyte alters the photoluminescent properties of the photoluminescent nanostructures.

A variety of nanostructures can be used in association with the nanosensors described herein. In some embodiments, carbon-based nanostructures are described. As used herein, a "carbon-based nanostructure" includes a fused network of aromatic rings wherein the nanostructure includes primarily carbon atoms. In some instances, the nanostructures have a cylindrical, pseudo-cylindrical, or horn shape. A carbon-based nanostructure can includes a fused network of at least about 10, at least about 50, at least about 100, at least about 1000, at least about 10,000, or, in some cases, at least about 100,000 aromatic rings. Carbon-based nanostructures may be substantially planar or substantially non-planar, or may comprise a planar or non-planar portion. Carbon-based nanostructures may optionally comprise a border at which the fused network terminates. For example, a sheet of graphene includes a planar carbon-containing molecule including a border at which the fused network terminates, while a carbon nanotube includes a nonplanar carbon-based nanostructure with borders at either end. In some cases, the border may be substituted with hydrogen atoms. In some cases, the border may be substituted with groups including oxygen atoms (e.g., hydroxyl). In other cases, the border may be substituted as described herein.

In some embodiments, the nanostructures described herein may comprise nanotubes. As used herein, the term "nanotube" is given its ordinary meaning in the art and refers to a substantially cylindrical molecule or nanostructure including a fused network of primarily six-membered rings (e.g., six-membered aromatic rings). In some cases, nanotubes may resemble a sheet of graphite formed into a seamless cylindrical structure. It should be understood that the nanotube may also comprise rings or lattice structures other than six-membered rings. Typically, at least one end of the nanotube may be capped, i.e., with a curved or nonplanar aromatic group. Nanotubes may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may comprise a carbon nanotube. The term "carbon nanotube" refers to nanotubes including primarily carbon atoms. Examples of carbon nanotubes include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The photoluminescent nanostructures described herein can be, in some cases, substantially free of dopants, impurities, or other non-nanostructure atoms. For example, in some embodiments, the nanostructure can comprise a carbon nanostructure that is substantially free of dopants. As a specific example, in some embodiments, the nanostructures may comprise single-walled carbon nanotube that contain only aromatic rings (each of which contains only carbon atoms) within the shell portion of the nanotube.

In some embodiments, the photoluminescent nanostructures described herein may emit radiation within a desired range of wavelengths. For example, in some cases, the photoluminescent nanostructures may emit radiation with a wavelength between about 750 nm and about 1600 nm, or between about 900 nm and about 1400 nm (e.g., in the near-infrared range of wavelengths). In some embodiments, the photoluminescent nanostructures may emit radiation with a wavelength within the visible range of the spectrum (e.g., between about 400 nm and about 700 nm).

Some embodiments can be particularly advantageous due to the biocompatible nature of hydrogels. Hydrogels are particularly resistant to biological fouling. When sensors are used in vitro, biological entities (e.g., endothelial cells, proteins, etc.) may adhere to the sensor and block and/or consume the compound to be detected (e.g., glucose). When this occurs, the sensor may fail to detect the presence of the compound, or may detect a concentration of the compound that is lower than the amount in the surrounding fluid (e.g., blood), thus rendering the sensor inaccurate or unusable. Because hydrogels can be resistant to biological fouling, such disadvantages can be mitigated. In addition, in some embodiments where the hydrogels are not biodegradable, undesired leaching of nanostructures may be prevented.

As used herein, the term "hydrogel" is given its ordinary meaning in the art and refers to a material including a polymer network that is able to trap and contain water. The hydrogel may include polymer chains that are crosslinked, either directly or via a crosslinking agent. The degree of crosslinking may be varied, in some cases, to tailor the extent to which the gel absorbs or retains fluids. Examples of polymers capable of forming hydrogels include, but are not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. A hydrogel can be an alginate hydrogel.

The hydrogel can be a porous structure. The pore sizes in the porous structure can be determined by factors including the concentration of polymers and crosslinks in the hydrogel. A hydrogel having a desired pore size or desired pore size distribution can be prepared by selecting the concentrations of monomers and crosslinkers present during polymerization to form a hydrogel. It can be advantageous for the hydrogel pores to be large enough to permit free access of analytes to components embedded in the hydrogel, e.g., to photoluminescent nanostructures. The pore size can be in the range of, for example, 10 nm to 1,000 nm, 20 nm to 500 nm, 50 nm to 250 nm, or 10 nm to 100 nm. When the analyte is a macromolecule (e.g., a protein, such as an immunoglobulin), a pore size greater than 10 nm, greater than 20 nm, greater than 30 nm, greater than 40 nm, greater than 50 nm, greater than 60 nm, greater than 70 nm, greater than 80 nm, greater than 90 nm, or 100 nm or greater can be desirable.

PEG hydrogels are widely used due to their variability and ease of use, allowing for the equal distribution of functional groups and a large degree of flexibility. See, Arshady, R. Beaded polymer supports and gels: II. Physicochemical criteria and functionalization. *Journal of Chromatography A* 586, 199-219 (1991), and Meldal, M. Properties of Solid Supports. *Methods in Enzymology* 289, 83-104 (1997), each of which is incorporated by reference in its entirety. PEG is also known for its hydrophilicity and biocompatibility, antigenicity and immunogenicity, making it an ideal candidate for encapsulation of SWNT sensors. Alginate, the most widely used material for microbead formation, is a naturally occurring anionic polysaccharide derived from brown algae and is another good candidate for SWNT encapsulation. See, Wei, X. et al. Biodegradable poly(e-caprolactone)-poly(ethylene glycol) copolymers as drug delivery system. *International Journal of Pharmaceutics* 381, 1-18 (2009), and Hall, K. K., Gattás-Asfura, K. M. & Stabler, C. L. Microencapsulation of islets within alginate/poly(ethylene glycol) gels cross-linked via Staudinger ligation. *Acta Biomaterialia* 7, 614-624 (2011), each of which is incorporated by reference in its entirety. Alginate has been approved for wound dressings and as a cell carrier due to its lack of toxicity, however it has been found that the ionically bonded hydrogels frequently suffer from degradation, unable to endure the mechanical and chemical strain of implantation and the exchange of cations that occurs in physiological conditions. See, Cho, W. J., Oh, S. H. & Lee, J. H. Alginate film as a novel post-surgical tissue adhesion barrier. *Journal of Biomaterials Science Polymer Edition* 21, 701-713 (2010), Lee, K. Y. & Mooney, D. J. Alginate: properties and biomedical applications. *Progress in Polymer Science* 37, 106-126 (2012), Ulery, B. D., Nair, L. S. & Laurencin, C. T. Biomedical applications of biodegradable polymers. *Journal of Polymer Science Part B: Polymer Physics* 49, 832-864 (2011), Benson, J. P., Papas, K. K., Constantinidis, I. & Sambanis, A. Towards the development of a bioartificial pancreas: effects of poly-L-lysine on alginate beads with BTC3 cells. *Cell Transplant* 6, 395-402 (1997), and Thu, B. et al. Alginate polycation microcapsules. II. Some functional properties. *Biomaterials* 17, 1069-1079 (1996), each of which is incorporated by reference in its entirety.

Essential to the success of a sensor implant is the ability to detect and transmit molecular detection from within the live, intact animal. Recent work shows detection of alginate encapsulated SWNT subcutaneously, but deeper tissue implantation was not investigated. See, Iverson, N. M. et al. In Vivo Biosensing Via Tissue Localizable Near Infrared Fluorescent Single Walled Carbon Nanotubes. *Nature Nanotechnology* 8, 873-880 (2013), which is incorporated by reference in its entirety. The goal of the following work is to provide a quantitative, materials-based framework from which to engineer implantable fluorescent sensors of various kinds. To this end, the relationship between tissue depth and signal detection for SWNT as a specific example in both alginate and PEG gels are analyzed and in vivo fluorescent imaging was demonstrated within a mouse, facilitating future in vivo use of such sensors and determine the potential of these gel encapsulates for deep tissue imaging.

In some embodiments, a nanosensor for detecting an analyte can include a photoluminescent nanostructure in a liquid medium, and a housing with pores, where the photoluminescent nanostructure is contained in the housing and transported through the pores. A housing can have pores that are big enough for an analyte to freely pass through but small enough to restrict the nanostructure to pass through. The housing can confine the nanostructure from external surroundings while allowing an analyte to interact with the nanosensor. A housing can be a membrane or a polymeric structure with suitable size pores to confine the nanosensor within the housing while allowing an analyte to pass through the housing. For example, the housing can include a membrane, such as a dialysis membrane. A liquid medium can be any solution compatible with the environment of the nanosensor, for example, a physiologically compatible buffer solution, such as PBS. For example, a dialysis tube filled with SWNT sensors in a buffer can be placed in a subject.

In one aspect, a sensor for detecting an analyte can be introduced to a subject by any effective route. Exemplary routes of introduction include, but not limited to, injection (such as subcutaneous, intramuscular, intradermal, intraperitoneal, and intravenous), oral, sublingual, rectal, transdermal, intranasal, vaginal and inhalation routes.

Disclosed herein is a sensor including single-walled carbon nanotubes tested in several contexts, including subcutaneously implanted sensors for inflammation detection and circulating sensors that localize within the liver for detection of reactive nitrogen species derived from NO. In vivo detection using this type of platform is possible by specifically designing the chemical interface between organism and sensor. A polyethylene glycol ligated ds($AAAT)_7$ (SEQ ID NO: 1) copolymer stabilizes near infrared fluorescent single-walled carbon nanotube (SWNT) sensors in solution, enabling intravenous injection into mice and the selective detection of local nitric oxide (NO) concentration with a detection limit of 1 µM. The half-life for liver retention is 4 hours, with sensors clearing the lungs within 2 hours after injection, avoiding a dominant route of in vivo nanotoxicology. A novel 2Dλ spatial-spectral imaging approach was introduced to deconvoluted chemical sensing and spatial information. After localization within the liver, the probes allow the study of transient inflammation using NO as a marker and signaling molecule. Alternatively, alginate encapsulated ds($AAAT)_7$-SWNT (SEQ ID NO: 1) is shown to function as an implantable inflammation sensor for NO, with no intrinsic immune reactivity or other adverse response, for more than 400 days. These results open new avenues for the use of such nanosensors in vivo for biomedical applications.

The Chemical and Optical Constraints of In Vivo Sensing

Using the SWNT as a fluorescent sensor in vivo introduces additional complexities over those of a passive delivery agent or imaging fluorophore. The SWNT must be functionalized such that selective molecular recognition is enabled, and that recognition is transduced optically by the SWNT. However, the selective coating must also allow for biocompatibility and stability in vivo, a constraint that significantly limits the available interfaces that can be used. Fluorometric sensors based upon SWNT or other nanoparticles necessarily optimize the extent and selectivity of modulation for a particular analyte over interfering molecules. See, Barone, P. W., Bak S., Heller, D. A. & Strano, M. S. Near-infrared optical sensors based on single-walled carbon nanotubes. *Nature Materials* 4, 86-U16 (2005), Heller, D. A. et al. Optical Detection of DNA Conformational Polymorphism on Single-Walled Carbon Nanotubes. *Science* 311, 508-511 (2006), Ahn, J. H. et al. Label-free, single protein detection on a near-infrared fluorescent single-walled carbon nanotube/protein microarray fabricated by cell-free synthesis. *Nano Letters* 11, 2743-2752 (2011), and Choi, J. H., Chen, K. H. & Strano, M. S. Aptamer-capped nanocrystal quantum dots: a new method for label-free protein detection. *Journal of the American Chemical Society* 128, 15584-15585 (2006), each of which is incorporated by reference in its entirety. However, operation in vivo adds the constraint that an adequate quantum yield (QY) must be maintained to allow detection from within tissue while remaining operable after conjugation with stabilizing components essential for in vivo biocompatibility.

Figure 2A:
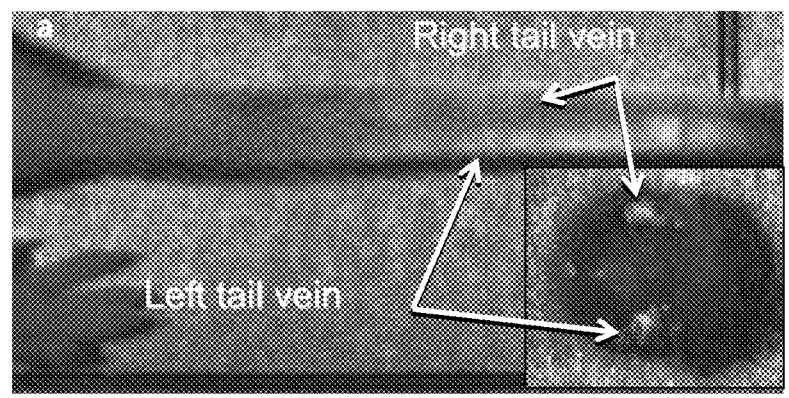
FIGS. 2A-2C depict effects of PEGylation for tail vein injected SWNT.
Figure 2B:
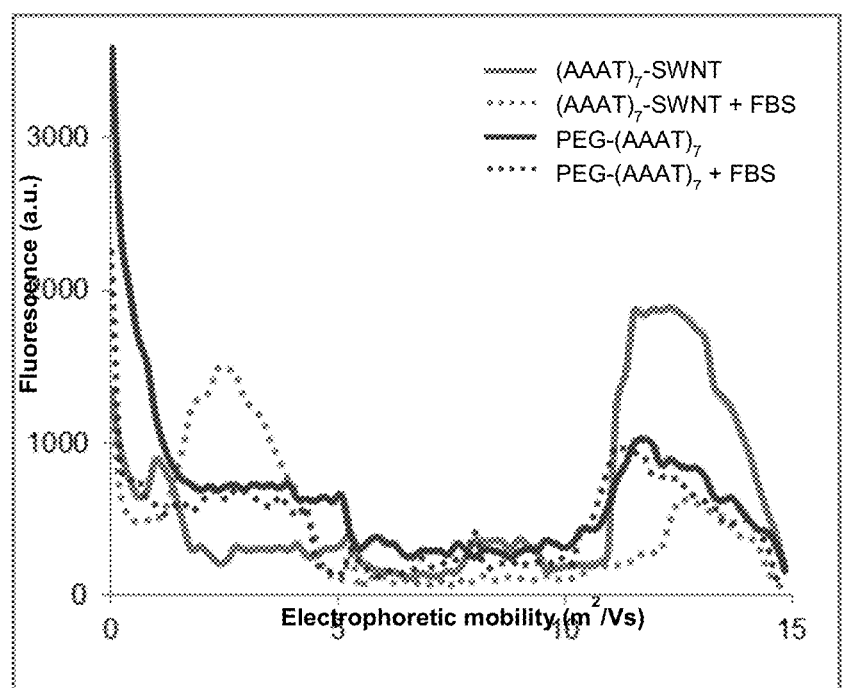
Figure 2C:
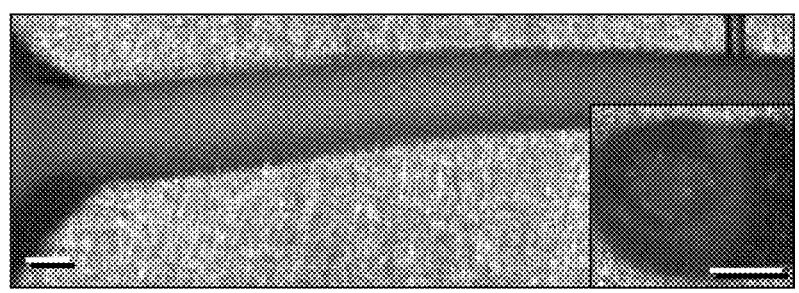
Figure 6:
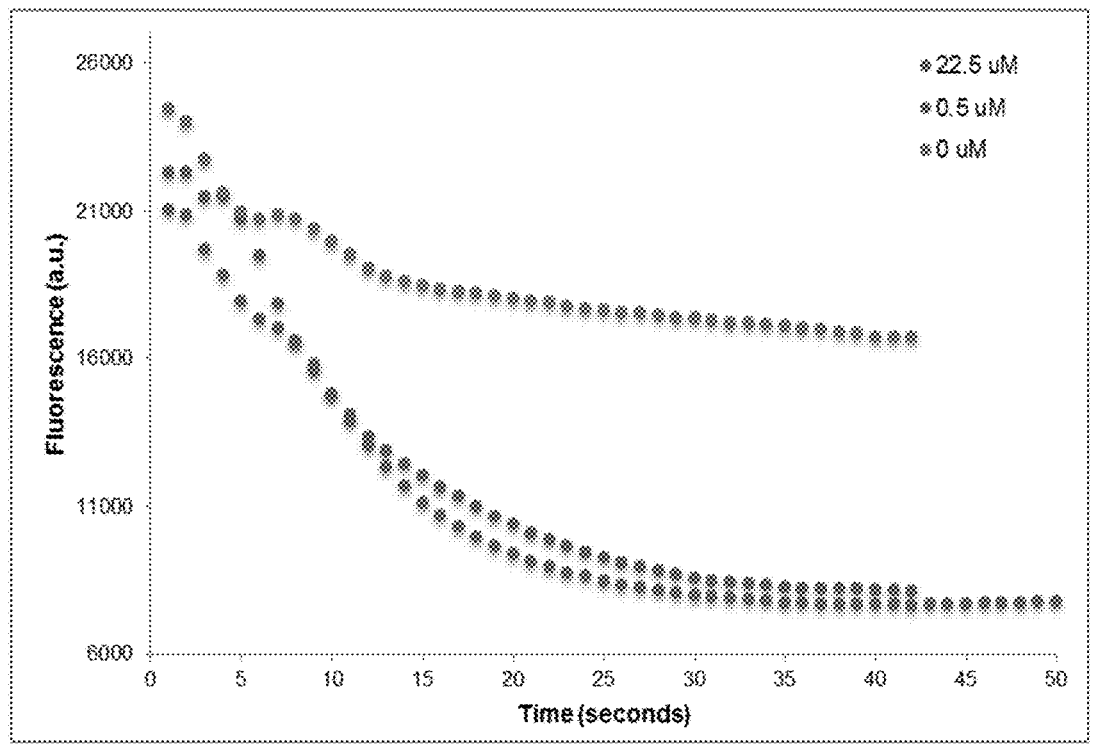
FIG. 6 is a graph depicting nitric oxide detection limit.

To address these constraints, a DNA oligonucleotide ds(AAAT)$_7$ (SEQ ID NO: 1) allows for nitric oxide selectivity that is maintained after ligation to a 5 kDa MW poly ethylene glycol (PEG) segment (FIG. 1A). FIGS. 2B-2C are graphs depicting quenching activity of (AAAT)$_7$-SWNT (SEQ ID NO: 1) (red) and PEG-(AAAT)$_7$-SWNT (SEQ ID NO: 1) (blue) sensors quantified by percent quenching of original fluorescence using a 785 nm photodiode following exposure to RNS and ROS compounds (analyzed continuously for 10 minutes and once at the 12 hours post addition time point) with error bars representing standard error (FIG. 2B) and NO (analyzed continuously for 30 minutes) (FIG. 2C). SWNT were dispersed using both the PEG-ligated and un-ligated DNA versions and tested for fluorescent modulation upon exposure to 30 μM nitric oxide and a battery of common potential interfering molecules, showing a 25% and 17% respectively greater reactivity to NO than any other analyte (FIG. 1B). Interestingly, addition of PEG decreases the SWNT response to HNO, and overall selectivity to NO is substantially higher than a diaminofluorescene standard, which measures only oxidation products of NO, and not the analyte directly, with an NO detection limit of less than 1 μM (FIG. 6). FIG. 6 shows fluorescence quenching of (AA AT)$_7$-SWNT (SEQ ID NO: 1) after addition of different concentrations of NO shows quenching from 0.5 μM of NO. The dynamic response and reversibility for both the PEG attached and unfunctionalized sensors appear in FIG. 1C. The rapid initial quenching rate is invariant for either construct, followed by a slower recovery due to solution degradation of the NO. The reversibility and rapidity of the response mean that for the first time this probe can be utilized to study NO signaling dynamics in vivo.

Spatial and Tissue Spectroscopic Imaging for Chemical Sensors

Figure 1D:
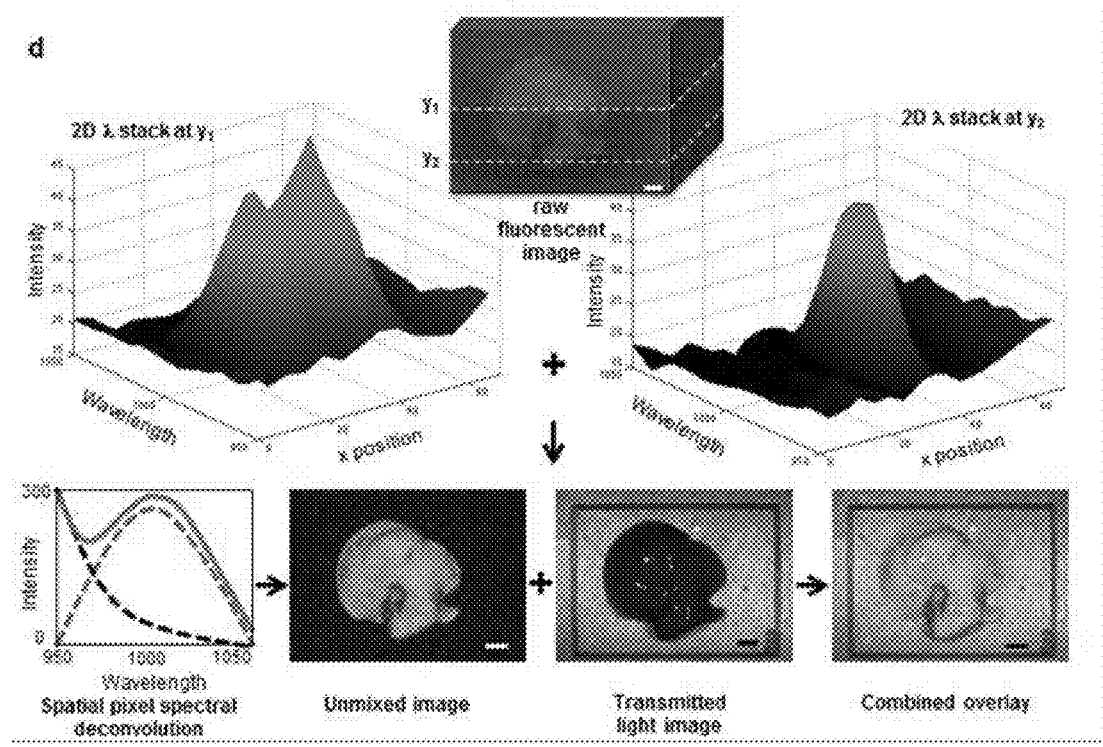

Unlike an invariant fluorescent or radiometric probe, an optical sensor must report both its position within the tissue and its chemical environment via either intensity or wavelength modulation. Hence, schemes that provide 2D static or dynamic images of fluorometric probes in vivo, and necessarily utilize intensity information to reveal location, cannot be used for chemical sensing. The development of liquid crystal tunable grading and filter technology provides a technological solution. By continuously tuning the grating to select a narrow wavelength space, an image stack $I(x,y,\lambda)_{raw}$ can be efficiently obtained via a rapid scan containing two spatial coordinates and the wavelength axis. A liquid crystal filter from CRi that afforded wavelength detection from 950 to 1050 nm was utilized, imposed upon a conventional whole animal field of view in a dark-box imaging configuration. The 2Dλ image stack easily encodes both spatial and chemical information, as demonstrated by the deconvolution of the raw stack to background and sensor components, allowing comparative fluorescence quenching (FIG. 1D). FIG. 1D is an imaging analysis for (AAAT)$_7$-SWNT (SEQ ID NO: 1) in an excised mouse liver 30 minutes after a tail vein injection of PEG-(AAAT)$_7$-SWNT (SEQ ID NO: 1) imaged with white light excitation and an emission spectrum from 950 to 1050 nm with a 10 nm step and 20 second accumulation time (scale bars 4 mm).

The narrow fluorescent full width at half maximum of the PEG SWNT sensor (100 nm) is easily deconvoluted from the sloping autofluorescence background typically encountered in natural and synthetic media. Using a custom Matlab algorithm the raw image intensity stack $I(x,y,\lambda)_{raw}$ was rapidly reduced into SWNT fluorescence, background and autofluorescence noise components:

$$I(x,y,\lambda)_{raw} = I(x,y,\lambda)_{SWNT} + I(x,y,\lambda)_{bkgd} + I(x,y,\lambda)_{auto} = k^{-1}*C_{NO}(x,y) + I(x,y,\lambda)_{bkgd} + I(x,y,\lambda)_{auto}$$

Here, k is a proportionality constant of calibration containing the molar extinction coefficient of the SWNT probe (4400+/−1000 M$^{-1}$ cm$^{-1}$) (see, Schoppler, F. et al. Molar Extinction Coefficient of Single-Wall Carbon Nanotubes. *Journal of Physical Chemistry* 115, 14682-14686 (2011), which is incorporated by reference in its entirety), its local concentration, and tissue optical properties. Note that this scheme easily lends itself to the multiplexing of fluorescent sensors in the wavelength band, or the analysis of the autofluorescence background or tissue absorption simultaneously with the SWNT sensor probe. Unless otherwise noted, fluorescent images in this work are $I(x,y)_{SWNT}$ spatial maps in which fluorescent intensity corresponds to relative NO concentration via quenching once normalized. Organic fluorometric probes, either in a turn-on or turn-off mode, require a reference to convey quantitatively spatial and chemical information simultaneously, and the SWNT probes are no different in this respect. To find the relative contribution of the SWNT fluorescence, background and autofluorescence noise at each point, a least squares minimization of a linear fit of the fluorescence spectrum was performed.

Stability to Tail Vein Injection

Ligation of PEG to the sensor interface is critical for successful circulation in vivo. For example, (AAAT)$_7$-SWNT (SEQ ID NO: 1) does not circulate, instead accumulating near the injection site, as shown using near-infrared imaging in FIG. 2A. FIG. 2A shows the administration of (AAAT)$_7$-SWNT (SEQ ID NO: 1) to first the left and then the right tail vein of a mouse. This procedure was done repeatedly with similar results; (AAAT)$_7$-SWNT (SEQ ID NO: 1) blocks the tail vein, inhibiting solution injection and blood flow. The insert in the image shows a cross section of the tail with the (AAAT)$_7$-SWNT (SEQ ID NO: 1) located within the veins, not the surrounding tissue. Hence, the vein occlusion was attributable to instability of the (AAAT)$_7$-SWNT (SEQ ID NO: 1) and not to erroneous injection. Further experiments show that tail vein blockage is caused by aggregates of serum proteins adsorbed to (AAAT)$_7$-SWNT (SEQ ID NO: 1). Gel electrophoresis in FIG. 2B shows four samples ((AAAT)$_7$-SWNT (SEQ ID NO: 1) and PEG-(AAAT)$_7$-SWNT (SEQ ID NO: 1) samples incubated with either fetal bovine serum (FBS) or buffer for 5 minutes before loading) and their migration distances as measured by fluorescence emission versus position. The zero point is the edge of the well with the fluorescence intensity measured at 1 mm distance intervals for all samples. The electrophoretic mobility of (AA AT)$_7$-SWNT (SEQ ID NO: 1) is 11*10$^9$ to 14*10$^9$ m$^2$ V$^{-1}$ while its FBS containing counterpart's mobility is 2*10$^9$ to 4*10$^9$ m$^2$ V$^{-1}$; confirming adsorption of FBS to (AAAT)$_7$-SWNT (SEQ ID NO: 1). Both the PEG-(AAAT)$_7$-SWNT (SEQ ID NO: 1) solutions with and without FBS had electrophoretic mobilities of 10*10$^9$ to 14*10$^9$ m$^2$ V$^{-1}$ with no perceptible difference between the two, confirming that the PEG moiety on the PEG-(AAAT)$_7$-SWNT (SEQ ID NO: 1) prevents FBS adsorption. The hypothesis that tail vein occlusion was caused by protein binding to (AAAT)$_7$-SWNT (SEQ ID NO: 1) was confirmed by visual inspection of the clearance of PEG-(AAAT)$_7$-SWNT (SEQ ID NO: 1) following injection into the vein, as shown in FIG. 2C. FIG. 2C is an image depicting mouse tail following injection (50 mg L$^{-1}$) of PEG-(AAAT)$_7$-SWNT (SEQ ID NO: 1) into the left tail vein, cross-sectional view shows clearance of SWNT from the vessel. (n=3, scale bars 2 mm). It shows that addition of PEG moieties is necessary to produce stable preparations for in vivo circulation of this type of sensor.

Circulation Time and Biodistribution

Figure 8:
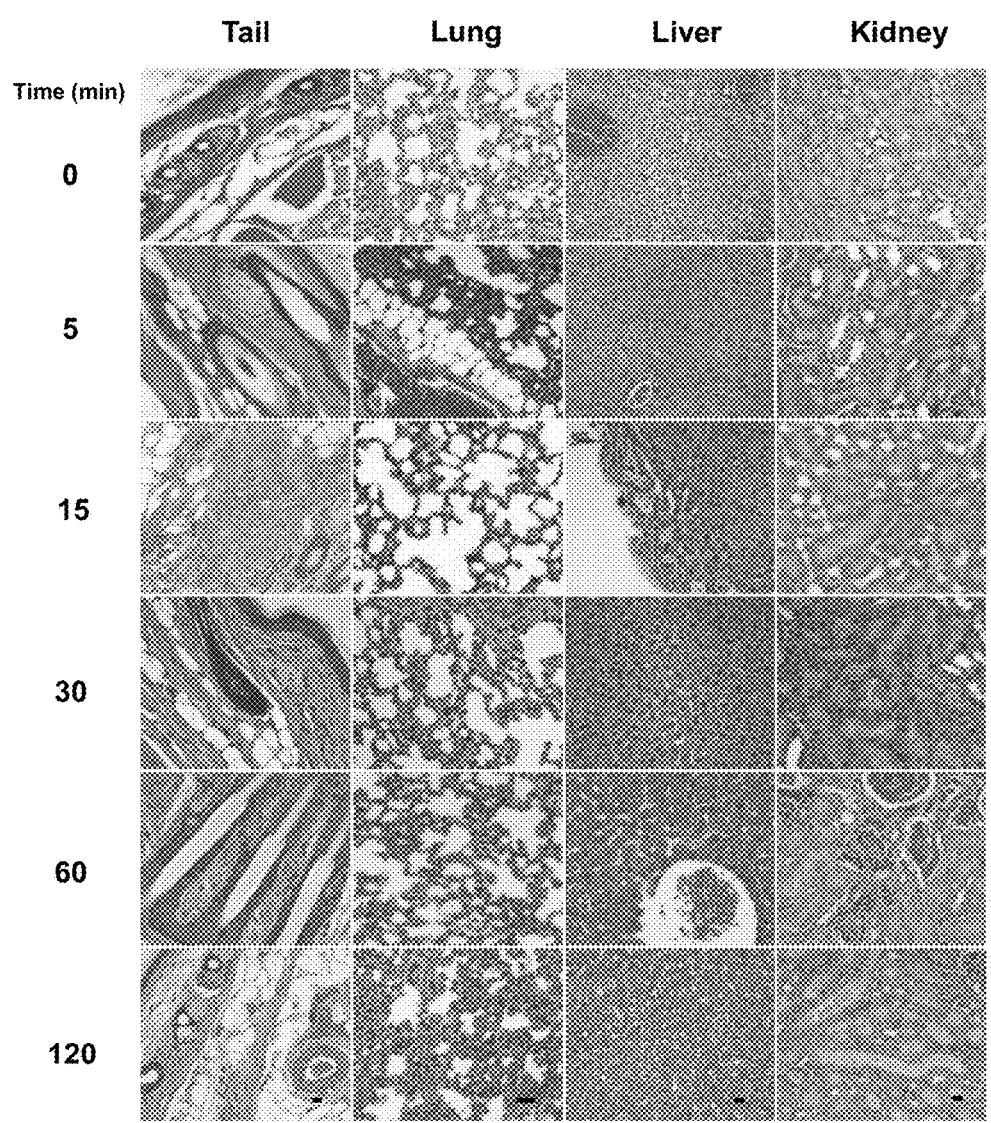
FIG. 8 is a series of images depicting biocompatibility of PEG-(AAAT)$_7$-SWNT (SEQ ID NO: 1) in mice.

Biodistribution and biocompatibility of SWNT was investigated as it is injected and localized within tissue, with results shown in FIGS. 3 and 8. Animals were injected with PEG-(AAAT)$_7$-SWNT (SEQ ID NO: 1) via the tail vein, then sacrificed at 5, 15, 30, 60 and 120 min after the injection (n=3-5 mice per time point, 200 μL injection of 50 mg L$^{-1}$ SWNT); 0 min time point represents control animals that did not receive PEG-(AAAT)$_7$-SWNT (SEQ ID NO: 1). FIG. 3A presents histology of liver tissue (60× magnification, scale bar 10 μm) before and after injection of PEG-(AAAT)$_7$-SWNT (SEQ ID NO: 1), and shows no evidence of an inflammatory response. FIG. 8 shows histology images (H&E stain, 10× for lung, 20× for tail, liver and kidney, scale bars 10 μm) of tissue sections from mice sacrificed at various time points after a tail vein injection of PEG-(AAAT)$_7$-SWNT (SEQ ID NO: 1) (200 μL injection of 50 mg L$^{-1}$ SWNT); no significant differences between time points was observed. (n=3-5 mice per time point).

Histological examination of hematoxylin and eosin (H&E) stained liver tissues shows no detectable evidence of inflammation in tail, lungs, liver or kidneys at any time, demonstrating biocompatibility of SWNT. FIG. 3B shows the presence (+) or absence (−) of PEG-(AAAT)$_7$-SWNT (SEQ ID NO: 1) in tissue samples, as determined by Raman spectroscopy (n=3 mice per time point) (sample spectrum shown in FIG. 3C). Resonance Raman spectroscopy of blood and urine samples shows the presence of SWNT in blood at all points, but no SWNT in urine samples collected from the bladder at each time point, confirming that SWNT remains in vivo for at least 2 hours. PEG-(AAAT)$_7$-SWNT (SEQ ID NO: 1) was also detected in liver and kidneys for the entire 2 hour time interval, but cleared the tail injection site within 1 hour. Clearance of SWNT from the lungs is particularly noteworthy. Due to the highly vascularized nature of lung tissue and its position within the systemic circulation, the lungs are highly susceptible to nanoparticle trapping. See, Donaldson, K. et al. Carbon Nanotubes: A Review of Their Properties in Relation to Pulmonary Toxicology and Workplace Safety. *Toxicological Sciences* 92, 5-22 (2006), Lacerda, L., Bianco, A., Prato, M. & Kostarelos, K. Carbon nanotubes as nanomedicines: From toxicology to pharmacology. *Advanced Drug Delivery Reviews* 58, 1460-1470 (2006), and Poland, C. A. et al. Carbon nanotubes introduced into the abdominal cavity of mice show asbestoslike pathogenicity in a pilot study. *Nature Nanotechnology* 3, 423-428 (2008), each of which is incorporated by reference in its entirety.

Remarkably, visual inspection revealed darkening of the lung tissue 5 minutes after injection, but tissue returns to pretreatment coloration within 30 minutes. This observation was documented quantitatively by Raman tissue spectroscopy, which confirmed that PEG-(AAAT)$_7$-SWNT (SEQ ID NO: 1) was detectable in the lungs 5 minutes after injection but cleared within two hours. This evidence directly supports the ability of PEG-(AAAT)$_7$-SWNT (SEQ ID NO: 1) to penetrate restrictive capillary networks without causing occlusions.

Figure 3D:
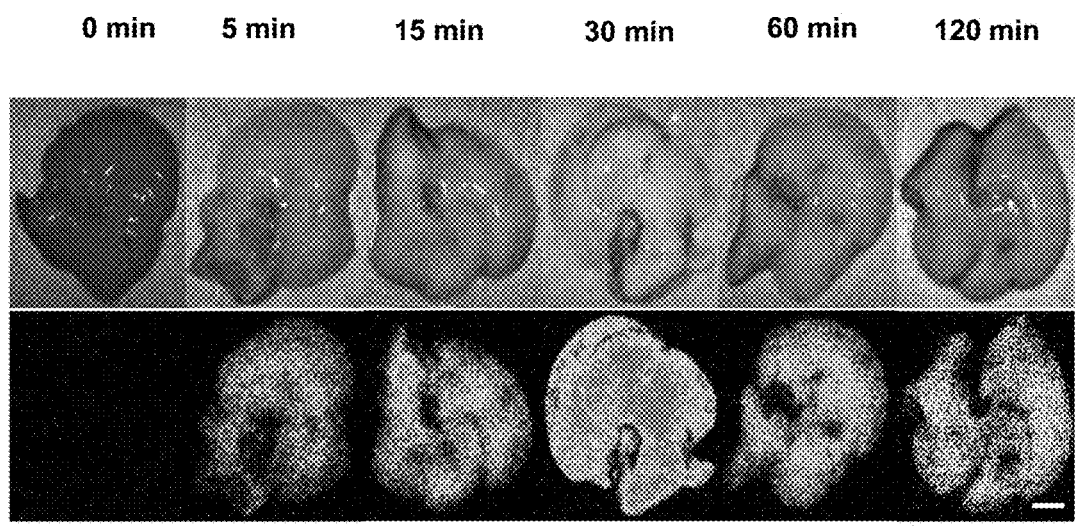
Figure 3E:
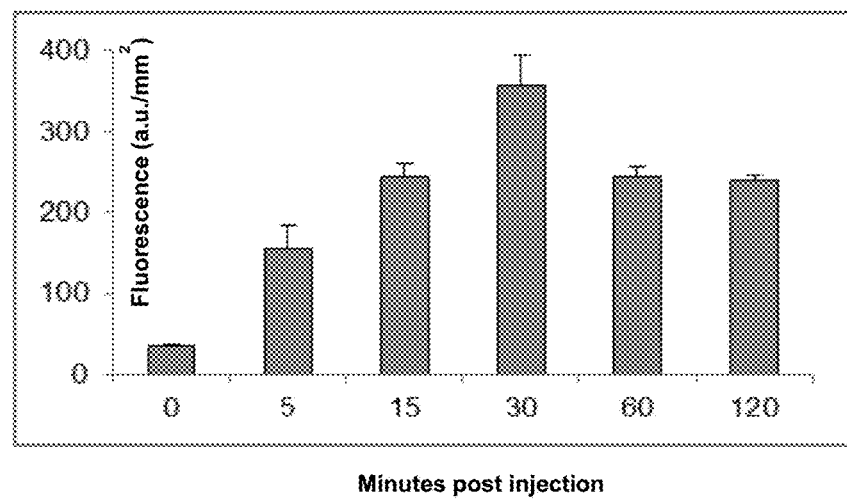
Figure 10:
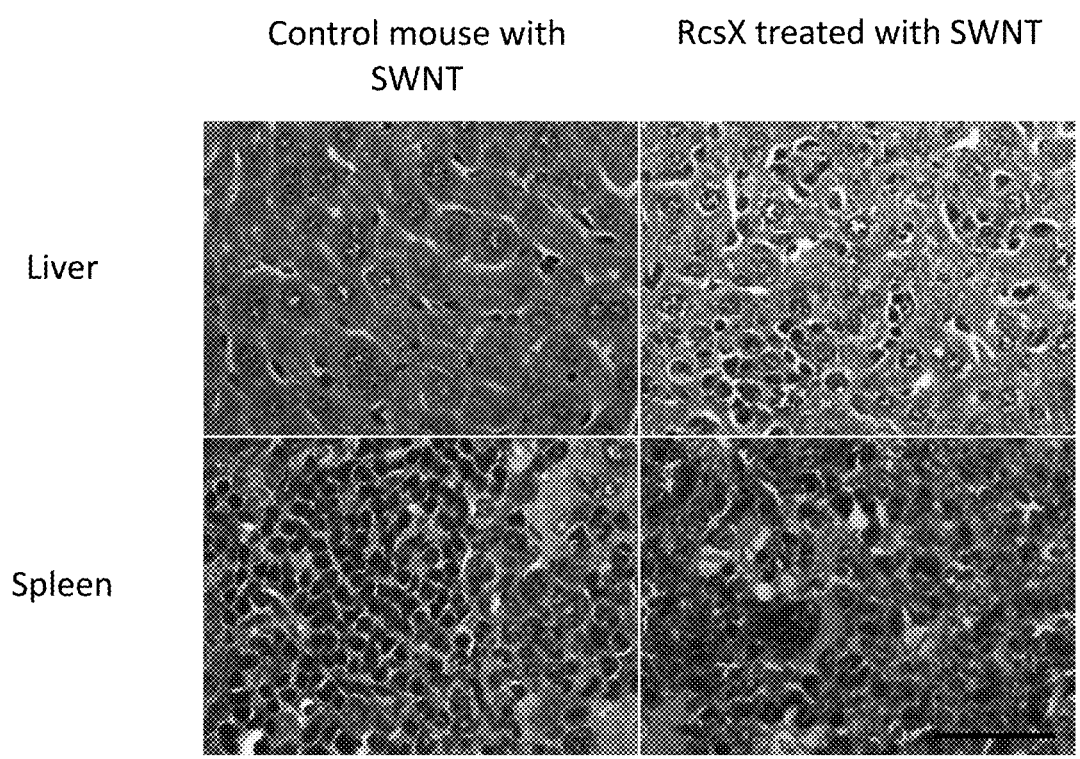
FIG. 10 is a series of images depicting level of inflammation in tissues from SJL mice.

PEG-(AAAT)$_7$-SWNT (SEQ ID NO: 1) accumulation in multiple tissues was observed, but the highest concentration in the liver. FIG. 3D is a series of images of excised livers deconvoluted with 2Dλ technology showing first PEG-(AAAT)$_7$-SWNT (SEQ ID NO: 1) localization relative in the liver then a heatmap of fluorescence (scale bar 4 mm). e, Chart with quantification of SWNT fluorescence in mouse livers excised at various time points following tail vein injection of 200 μL of 50 mg L$^{-1}$ PEG-(AAAT)$_7$-SWNT (SEQ ID NO: 1). (n=3-5 mice per time point, error bars are s.e.m.) FIGS. 3D-3E summarize qualitative and quantitative evidence of PEG-(AAAT)$_7$-SWNT (SEQ ID NO: 1) accumulation in excised livers of mice sacrificed 5, 15, 30, 60 and 120 min after injection, as in the biodistribution study described above. Representative images of the liver clearly show an increase in SWNT fluorescence up to 30 min, followed by a small decrease. Quantitative analysis, performed with the 2Dλ approach described in FIG. 1, shows that the average fluorescence for the livers increases up to 30 min, then decreases slightly and stays constant up to 60 and 120 min. Samples that have been quenched show a fluorescence distribution with larger standard deviations and lower peak value compared to non-quenched samples, shown in FIG. 10. FIG. 10 shows histology images (H&E stain, 40×, scale bar 10 μm) of tissue sections from healthy (control) and inflamed (RcsX treated) mice sacrificed 30 minutes after a tail vein injection of PEG-(AAAT)$_7$-SWNT (SEQ ID NO: 1) (200 μL it injection of 50 mg L$^{-1}$ SWNT). There is no discernible difference between liver samples of control and inflamed mice, while spleen from RcsX treated animals shows lymphoma that is not present in control mice. (n=10)

Figure 3F:
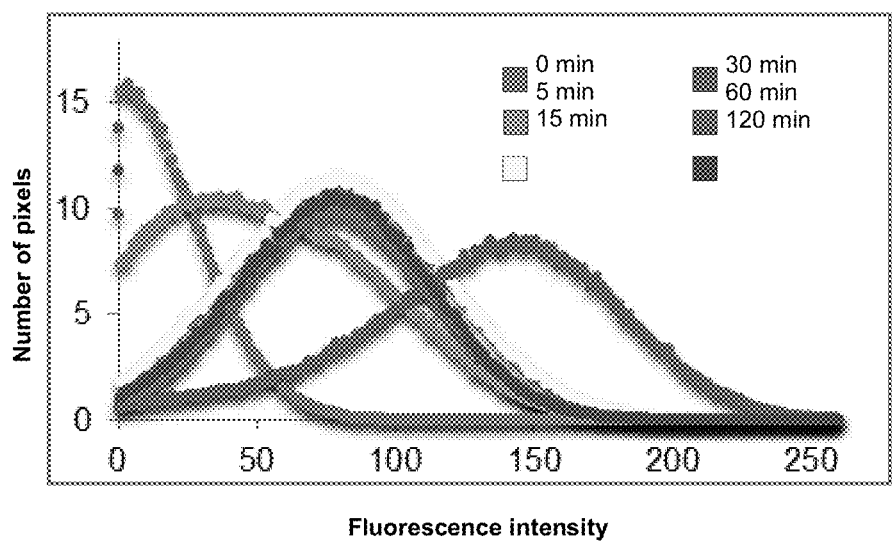
Figure 3G:
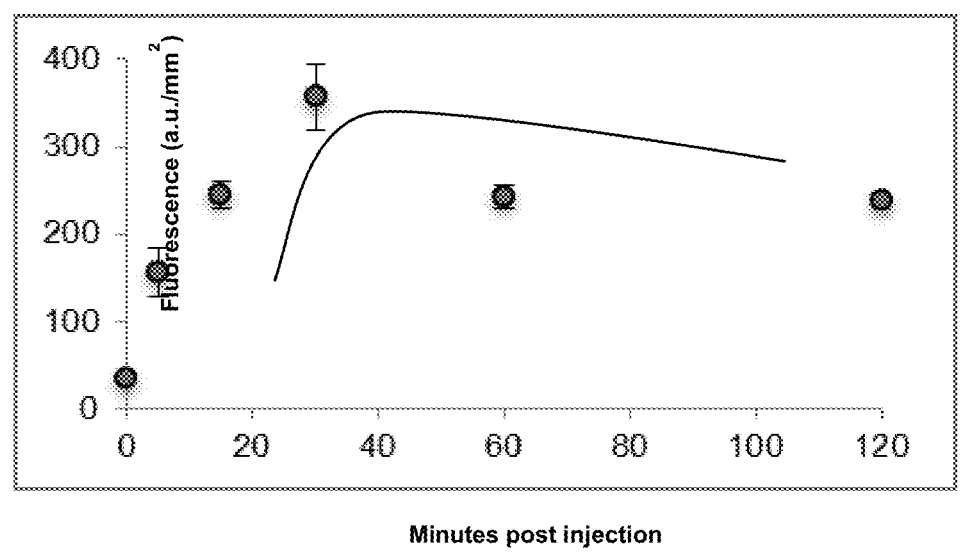

The fluorescence distribution of the data from FIG. 3E, shown in FIG. 3F, shows similar peak values (10.5, 11.2, 8.1, 9.6 and 10.4) and standard deviations (73.19, 56.43, 63.07, 48.92 and 49.51 a.u.) for all time points, implying an increase and then decrease in PEG-(AAAT)$_7$-SWNT (SEQ ID NO: 1) concentration within the liver as opposed to SWNT quenching after the 30 min time point.

Accumulation of the PEG-(AAAT)$_7$-SWNT (SEQ ID NO: 1) in the liver can be modeled as follows, accounting for the circulation half-life from the blood (point A) into the liver (B) and distribution into a variety of sinks (C, bile, degradation, etc.).

$$A \xrightarrow{k_1} B \xrightarrow{k_2} C$$

Here, $k_1$ is the rate constant of transfer from the circulation to the liver, and $k_2$ is the dominant sink rate. Hence, for concentrations A(t), B(t) and C(t), $$A(t) = [A]_0 e^{-k_1 t},$$

$$B(t) = \frac{k_1 [A]_0}{k_2 - k_1}(e^{-k_1 t} - e^{-k_2 t}),$$

$$C(t) = [A]_0 \left(1 + \frac{1}{k_2 - k_1}(k_2 e^{-k_1 t} - k_1 e^{-k_2 t})\right)$$

where $A_0$ is the blood concentration at time t. A regression of the data in FIG. 3e yields $k_1$=0.1169 $k_2$=0.00288 and $[A_0]$=337.96 sec$^{-1}$ such that $$B(t) = -346.51(e^{-0.1169t} - e^{-0.00288t})$$

With $$t_{\frac{1}{2}liver} \approx \frac{\ln(z)}{k_2} \approx 240.17 \text{ minutes} \approx 4 \text{ hours}$$

Therefore, the regression of the data in FIG. 3E yields a SWNT concentration within the liver of $B(t)=-346.51(e^{\wedge}(-0.1169t)-e^{\wedge}(-0.00288t))$ and half life of approximately 4 hours.

More accurate liver half-life values require a more detailed model informed by longer time points, the focus of future efforts. Also of interest are blood concentration studies to enable for bloodstream half-life determination.

Detection of Nitric Oxide in Inflamed Mouse Liver

Figure 4A:
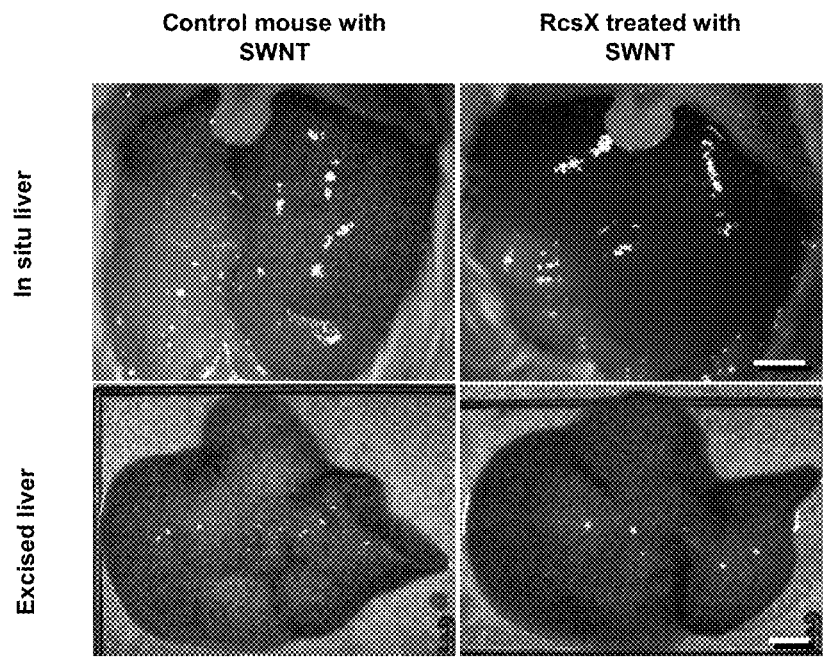
FIGS. 4A-4C depict in vivo sensor quenching due to inflammation.
Figure 4B:
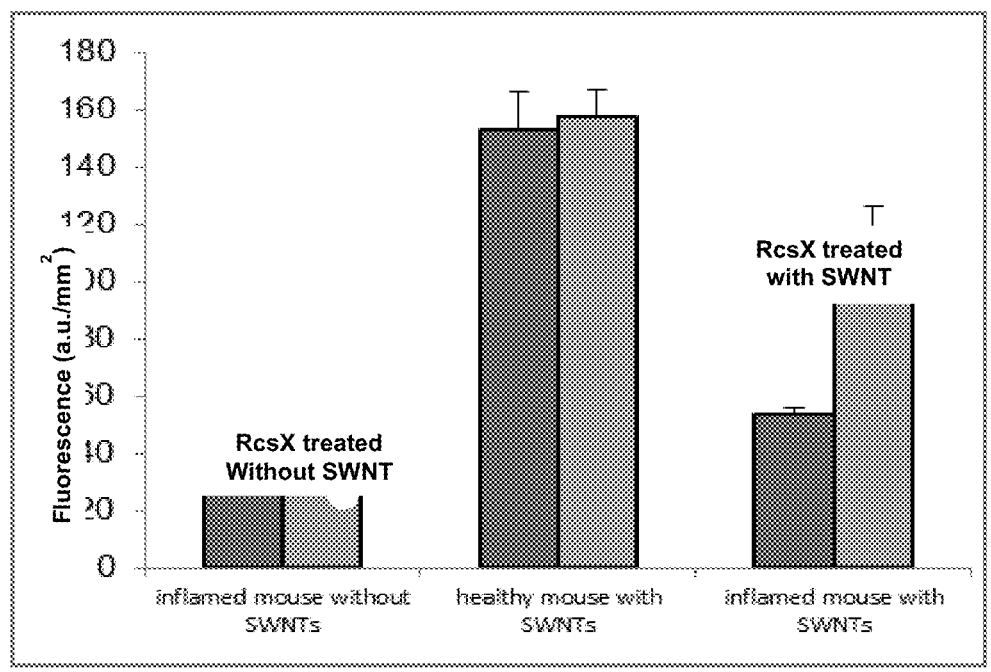
Figure 4C:
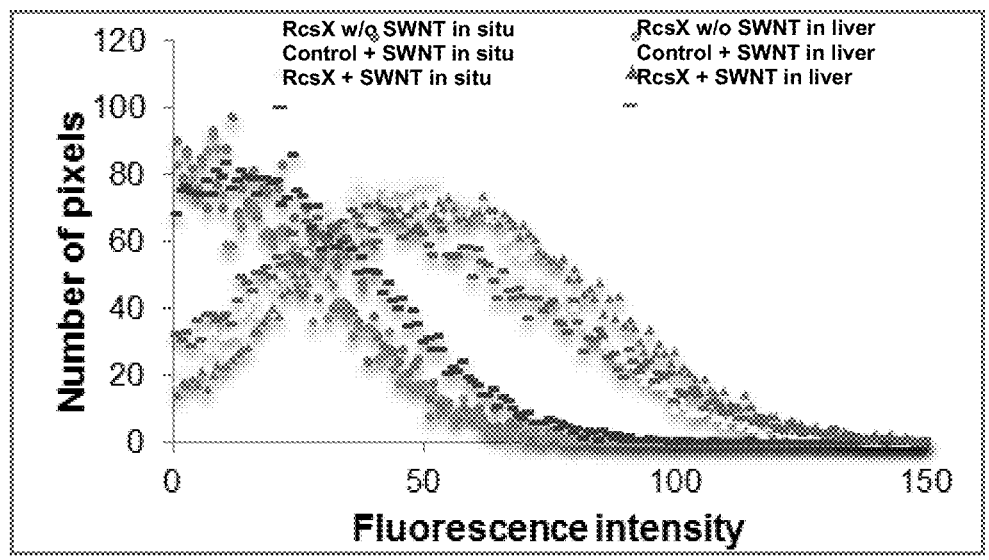

The ability of the sensor to detect NO produced during inflammation in vivo was assessed. For this purpose, the SJL mouse model was chosen due to its intense inflammatory response resulting in massive overproduction of NO over a predictable time course after induction by an injection of RcsX tumor cells, as previously described. See, Gal, A., Tamir, S., Tannenbaum, S. & Wogan, G. Nitric oxide production in SJL mice bearing the RcsX lymphoma: A model for in vivo toxicological evaluation of NO. *Proceedings of the National Academy of Sciences* 93, 11499-11503 (1996), which is incorporated by reference in its entirety. Accordingly, mice were injected intraperitoneally with RcsX cells or saline (n=10, repeated once with n=5). After 12 days, PEG-(AAAT)$_7$-SWNT (SEQ ID NO: 1) (200 µL injection of 50 mg L$^{-1}$ SWNT) was injected into the tail vein of anesthetized mice, and 30 minutes later a cut in the abdominal cavity exposed the liver to allow in situ imaging (FIG. 4A, scale bars 4 mm). Immediately thereafter the animal was sacrificed, the liver excised and the isolated organ imaged a second time. Comparison of in situ images shows that livers of control animals clearly displayed fluorescence, whereas it was undetectable in inflamed organs of RcsX treated mice. In contrast, images of excised livers show that similar levels of SWNT fluorescence are present in both RcsX and control animals. Absence of fluorescence in the in situ images was attributable to NO generated during inflammation, since SWNT was clearly present in the organs as shown by fluorescence in excised organs. The rapid recovery of PEG-(AAAT)$_7$-SWNT (SEQ ID NO: 1) fluorescence after exposure to NO (FIG. 1C) is consistent with this interpretation. Quantification of these data was performed (FIG. 4B, n=10, error bars are s.e.m.) and showed a 55% difference between pre- and post-sacrifice fluorescence in inflamed tissues compared to 3% difference in controls that received a tail vein injection of saline. Fluorescence distribution data shows the similarity between tissue of control mice without SWNT and the signal detected in the inflamed animals with injected SWNT (39 and 54 a.u. mm$^{-2}$ compared to 153 a.u. mm$^{-2}$ for non-inflamed mice with SWNT) while the excised liver samples for both inflamed and non-inflamed mice have similar standard deviations (48.14 and 43.41 a.u.) and peak values (148 and 158 a.u.). A limitation of this study is the need to expose the liver for in situ imaging, which can be addressed by further optimization of the SWNT to enable deeper tissue imaging or the use of a laproscopic probe to allow imaging with an even smaller incision than currently used.

A Nitric Oxide Monitor for Epidermal Tissue Inflammation

Figure 5A:
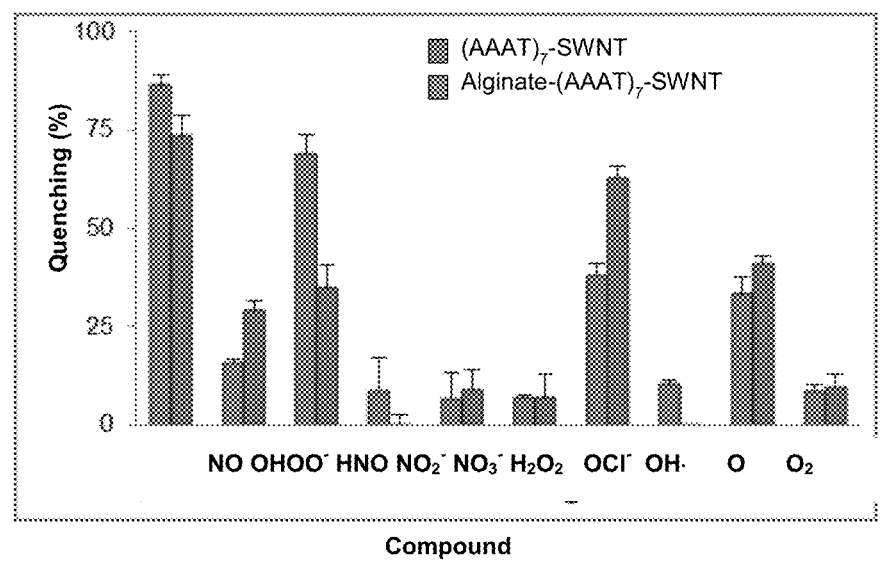
FIGS. 5A-5F depict an additional sensor construct with broader in vivo localization possibilities and long term sensing capabilities.
Figure 5B:
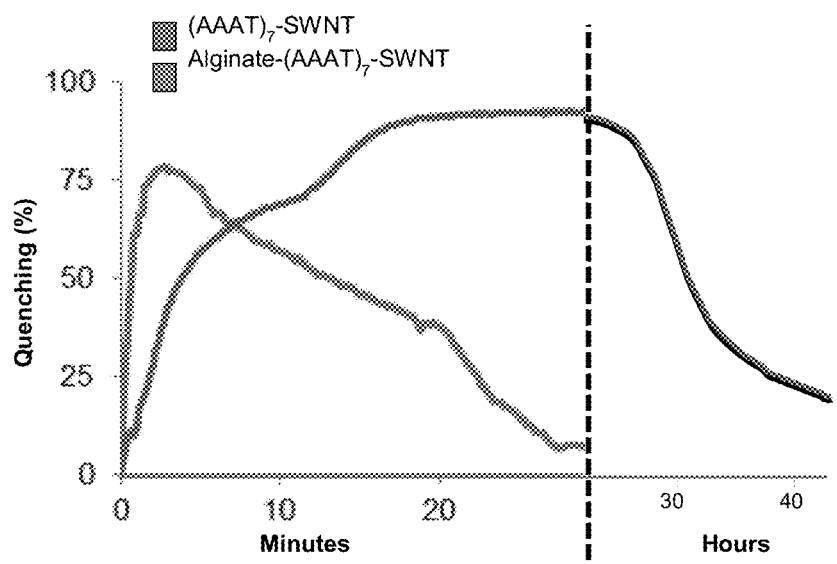
Figure 5C:
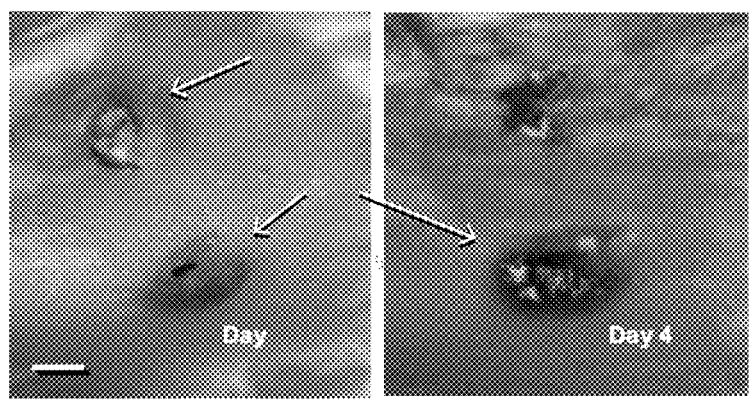

The potential of tissue-specific localization of (AAAT)$_7$-SWNT (SEQ ID NO: 1) was also investigated using an alginate-encapsulated sensor platform that can be implanted and perform on a multiple day/months time scale as opposed to the shorter time scale utilized by the intravenously injected PEG-(AAAT)$_7$-SWNT (SEQ ID NO: 1). FIGS. 5A-5B are graphs depicting quenching activity of (AAAT)$_7$-SWNT (SEQ ID NO: 1) (red) and Alginate-(AAAT)$_7$-SWNT (SEQ ID NO: 1) (green) sensors quantified by percent quenching of original fluorescence using a 785 nm photodiode following exposure to RNS and ROS compounds (FIG. 5A, analyzed continuously for 10 minutes and once at the 12 hours post addition time point) with error bars representing standard error NO (FIG. 5B, analyzed continuously for 30 minutes for (AAAT)$_7$-SWNT (SEQ ID NO: 1) and just under 45 hours for Alginate-(AAAT)$_7$-SWNT (SEQ ID NO: 1)) (n=3). FIG. 5A shows that the alginate-(AAAT)$_7$-SWNT (SEQ ID NO: 1) sensor retains its NO specificity. Interestingly, the fluorescence signal was quenched less rapidly by NO, reaching 93% quenching after 30 minutes of NO exposure (FIG. 5B). The signal remained quenched for 24 hours, after which it returned to 25% after 41 hours. Several possible mechanisms could be responsible for the delayed fluorescence recovery. It is possible that NO adsorbed to alginate-(AAAT)$_7$-SWNT (SEQ ID NO: 1) is more stable than free NO, increasing its half-life significantly and causing the NO to be concentrated in the alginate hydrogel. It is also possible that a long-lived reactive derivative of NO is responsible for the quenching of the alginate-(AAAT)$_7$-SWNT (SEQ ID NO: 1) system. This seems plausible if the NO enters the alginate hydrogel and reacts with another negatively charged analyte trapped in the alginate matrix. Another possibility is that NO forms an alginate intermediate that quenches the SWNT.

Subcutaneous implantation and NO detection was performed with alginate encapsulated (AAAT)$_7$-SWNT (SEQ ID NO: 1), with results shown in FIG. 5. The first study (FIG. 5C, scale bar 4 mm), involved subcutaneous (SQ) placement of two alginate-(AAAT)$_7$-SWNT (SEQ ID NO: 1) gels on both the left and right flanks of a mouse. Total signal quenching of gel 1 was observed in the first image, taken approximately 20 minutes after the gel was placed, while gel 2 retained its fluorescence. In a subsequent image, after gel 2 was in the animal for approximately 20 minutes, gel 2 was also quenched. By day 4 both gels regained their fluorescence. Few quantitative data are available on in vivo levels of NO, which are thought to be very low (i.e., nM) in non-inflamed tissues. However, during a wound healing study by Lee et al. it was shown that NO levels in rat wound fluid increased steadily from 27 to 107 µM over a 14 day period, with nitric oxide synthase activity peaking at 24 hours post injury. See, Lee, R. H., Efron, D., Tantry, U. & Barbul, A. Nitric Oxide in the Healing Wound: A Time-Course Study. *Journal of Surgical Research* 101, 104-108 (2001), which is incorporated by reference in its entirety. Therefore the concentration of NO in the wound bed can be high enough to quench the SWNT shortly after implantation. The prolonged NO presence that Lee et al. observed with polyvinyl alcohol sponges in rats was not observed in this study with alginate gels in mice, but the recruitment of macrophage cells, known NO producers, or foreign body response that has been associated with polyvinyl alcohol sponges was also not observed in this study. See, Davidson, J. M. Animal Models for Wound Repair. *Archives of Dermatological Research* 290, S1-S11 (1998), which is incorporated by reference in its entirety. These observations support the interpretation that the absence of signal observed on day 0 of the experiments resulted from fluorescence quenching associated with a burst of NO due to gel implantation, not to tissue interference with the fluorescence. This fast quenching and multiple day signal recovery corresponds to the data shown in FIG. 5B. Tissue from the animal was collected post-sacrifice on day 4 and stained with H&E (FIG. 5F, 10× (day 4 and day 400) and 20× (day 180), scale bars 10 μm). Negligible inflammation was present at the site of implantation, also supporting the hypothesis relating to the fluorescence signal recovery that was observed.

Figure 11:
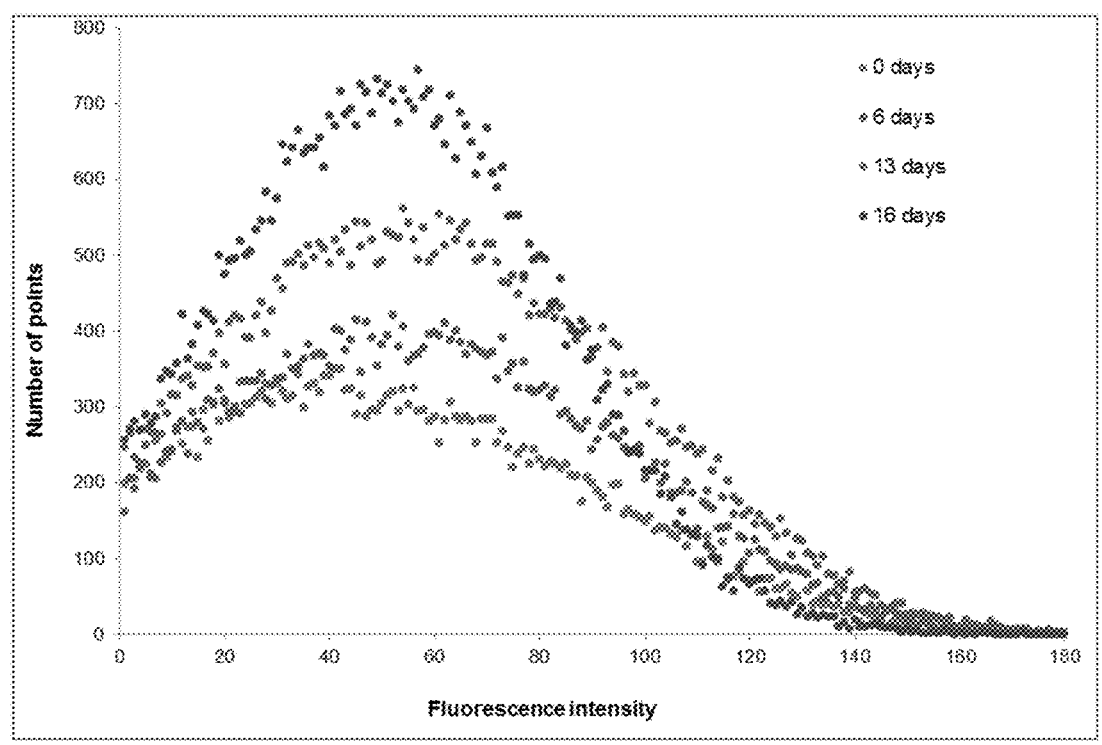
FIG. 11 is a graph depicting fluorescence intensity distribution for mouse with subcutaneous gel following implantation.

FIG. 11 is a graph depicting fluorescence intensity distribution for mouse with subcutaneous gel following implantation. Quantification of Alginate-(AAAT)$_7$-SWNT (SEQ ID NO: 1) fluorescence distribution shows that the signal recovery of the gel, following quenching caused by implantation, leads to a decreasing standard deviation (64.95 to 46.43 a.u.) and increasing peak (336 to 733 points) for the Gaussian shaped curve.

Figure 5D:
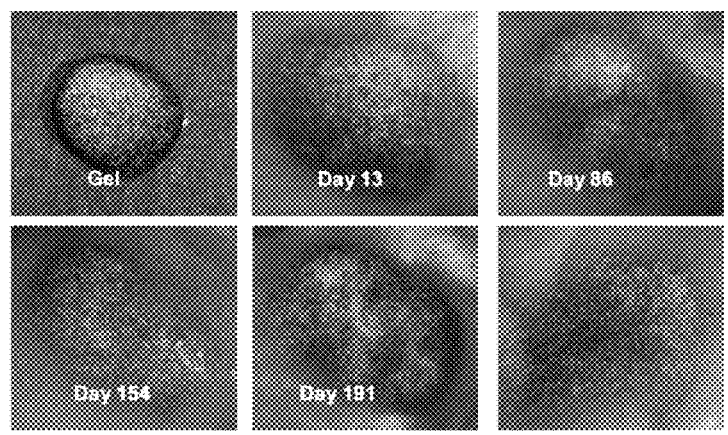
Figure 5E:
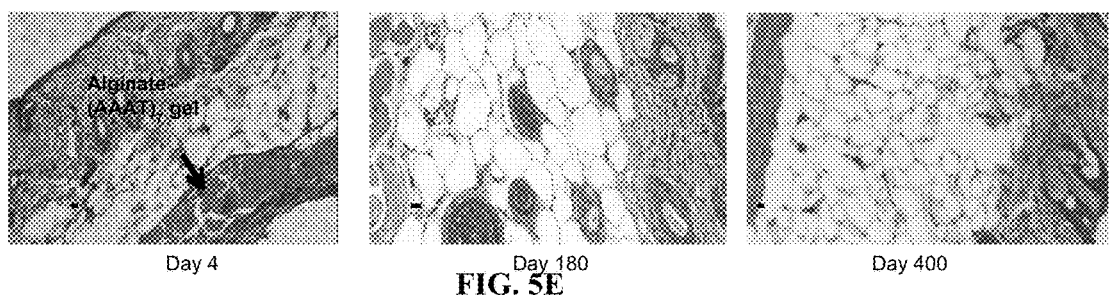
Figure 5F:
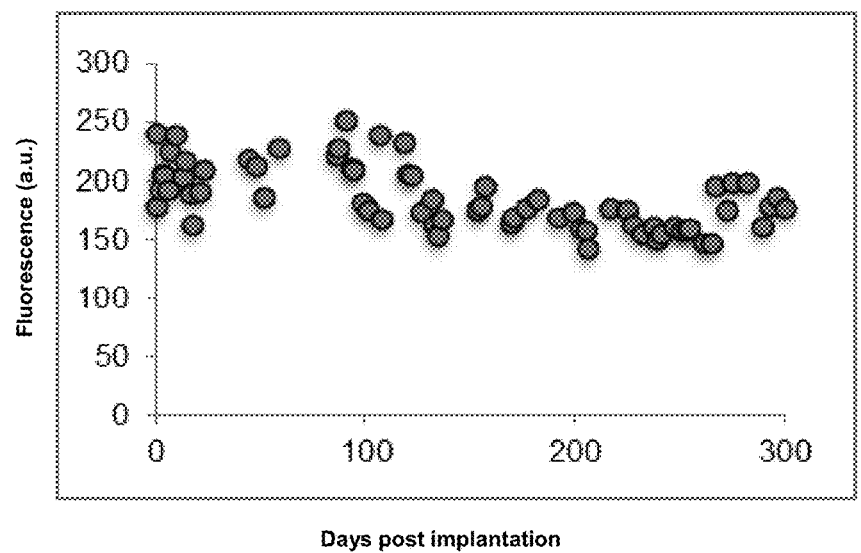
Figure 12:
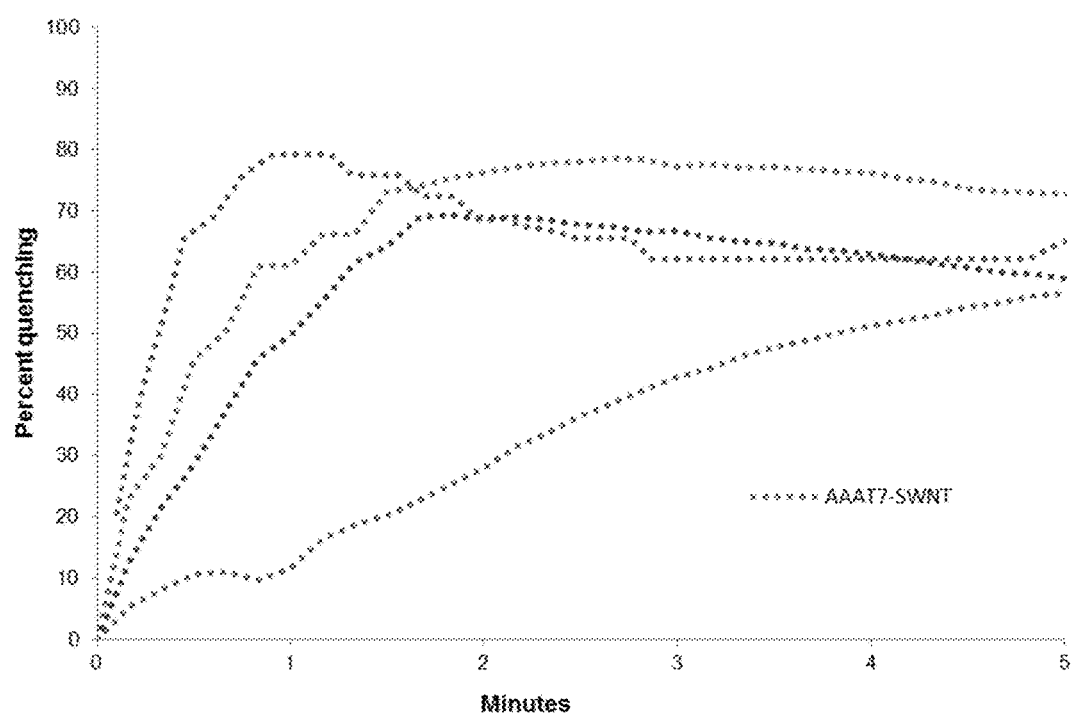
FIG. 12 is a graph depicting fluorescence quenching of SWNT with alternate gel composition. Figure discloses "AAAT7" as SEQ ID NO: 1.

FIGS. 5D-5F show the results from an unprecedented long-term durability study of the alginate-(AAAT)$_7$-SWNT (SEQ ID NO: 1). Here, a single subcutaneous gel implantation into the right flank was monitored and fluorescence imaged for 60 to 400 days, far longer than implantable electrochemical sensors, the closest current technology, have been shown to monitor NO. See, Griveau, S. & Bedioui, F. Overview of significant examples of electrochemical sensor arrays designed for detection of nitric oxide and relevant species in a biological environment. *Analytical and Bioanalytical Chemistry* 405, 3475-3488 (2013), which is incorporated by reference in its entirety. In FIG. 5D, the gel is shown prior to implantation and then in vivo for multiple points during a 300 day study. Prominent fluorescence can be seen throughout the 300 days of the study. Gel morphology appears to change slightly over time due to animal movement, but the gel remains intact and the signal is largely invariant, as seen in FIG. 5F. Quantification of fluorescence intensity over the experimental time course is charted in FIG. 5F (signal recovery after implantation shown in FIG. 11). The signal was retained over the entire period, with variability of 14% in intensity. The small variation suggests that local NO concentration may have changed slightly over the 10 month period, but remained lower than the initial rise observed at the time of implantation, possibly caused by tissue damage involved in the surgical procedure. Consistent with this interpretation, inflammation was not observed in tissue surrounding the sites of gel implantation at the conclusion of the long-term studies (FIG. 5E). A particularly compelling aspect of these findings is that a change in SWNT concentration within the alginate gels or an alteration in gel composition (FIG. 12) changes the timescale and degree of signal quenching. FIG. 12 shows fluorescence signal quenching by NO of PAAm encapsulated (AAAT)$_7$-SWNT (SEQ ID NO: 1) shows a shorter time than its alginate counterpart.

Hence, a sensor library can be constructed to contain gels with different NO concentration limits, allowing for specification directly related to the disease or condition of interest.

In conclusion, this work shows direct optical sensor for in vivo NO detection with a detection limit of about 1 μM made with semiconducting SWNT, and highlights the potential for semiconducting single walled carbon nanotubes to be utilized in vivo for chemical detection, and has produced the first reversible, direct optical sensor for NO capable of in vivo operation. Demonstrated stability of such sensors in vivo for over a year (for at least 400 days, observing negligible change of activity) is unprecedented and, due to the absence of photobleaching, has the potential for even longer time periods. Two modes of operation: injection followed by localization within the liver, as well as direct implantation within tissue, are both demonstrated; allowing for increased knowledge associated with tissue inflammation, cancer and cell signaling. See, Bredt, D. S. & Snyder, S. H. Nitric Oxide: A Physiologic Messenger Molecule. *Annual Review of Biochemistry* 63, 175-195 (1994), and Mantovani, A., Allavena, P., Sica, A. & Balkwill, F. Cancer-related inflammation. Nature 454, 436-444 (2008), each of which is incorporated by reference in its entirety.

In Vivo Detection of Glucose Utilizing Liquid SWNT Solution

In certain circumstance where the sensitivity of the sensor is compromised because of the presence of the hydrogel, SWNT sensors can be place in vivo in their liquid form. In such cases, SWNT sensor are formulated in a liquid medium. A porous housing can be filled with the SWNT sensors in a liquid medium and then placed in a subject. For example, when certain SWNT sensors, such as a glucose sensor, are encapsulated within a hydrogel they lose their ability to react specifically to the analyte of interest. To overcome this issue, the SWNT sensors can be placed in vivo in their liquid form. The glucose sensing SWNT can be filled within a dialysis tube tied off at both ends with suture material. The dialysis tube then can be placed subcutaneously in a mouse (see FIG. 13).

Figure 13:
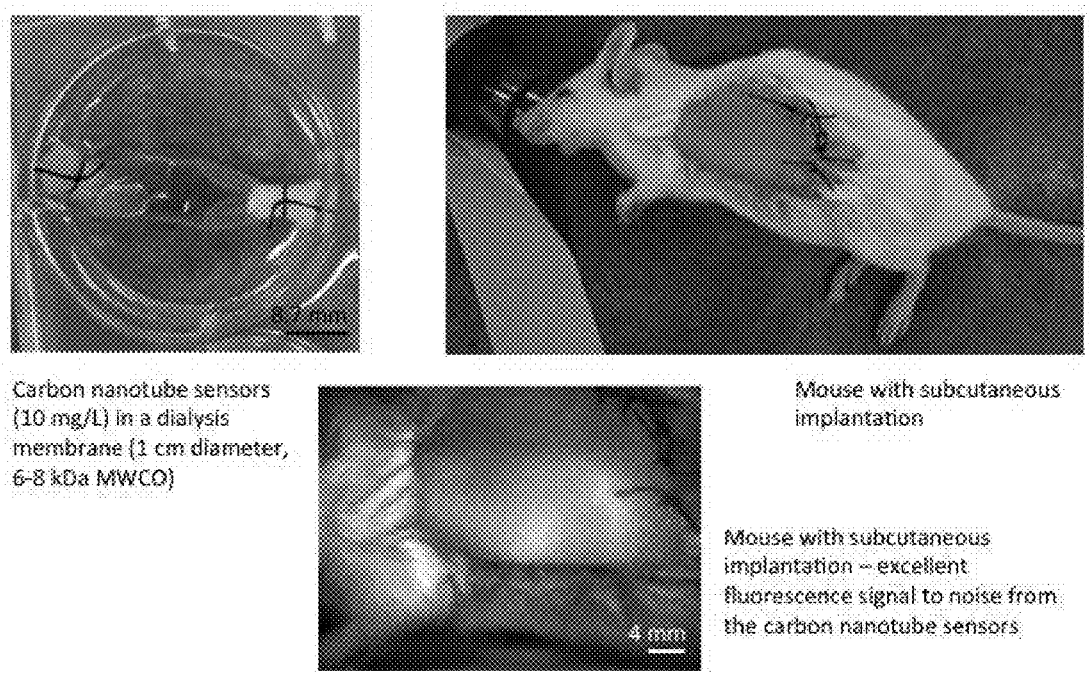
FIG. 13 is a series of images depicting implantation of SWNT sensors in a liquid form.
Figure 14:
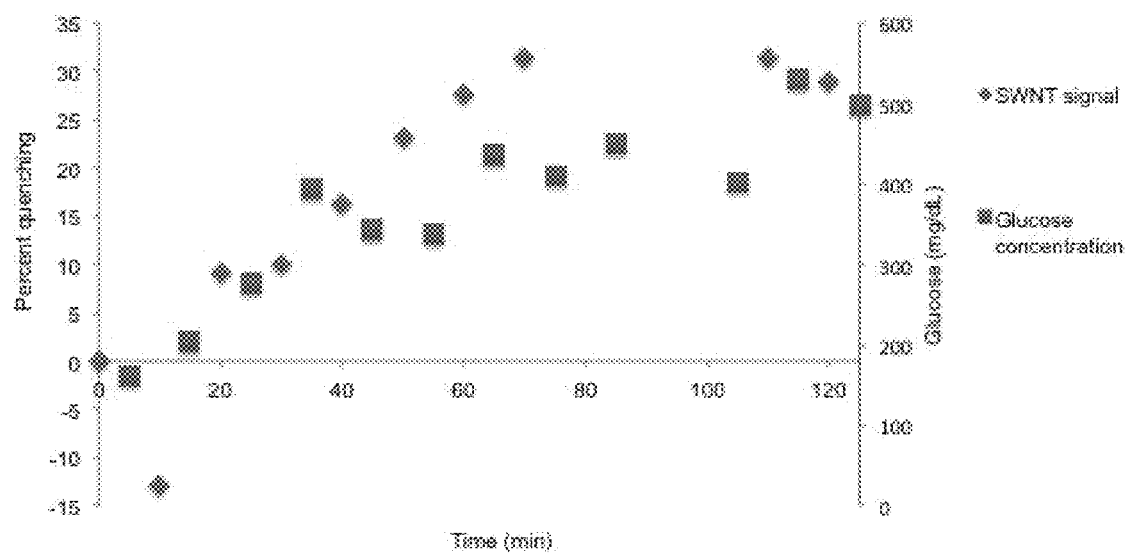
FIG. 14 is a graph depicting glucose tolerance test.

FIG. 13 shows a dialysis tube in a 6-well plate before implantation and a mouse with the dialysis bag implant (both with transmitted light and then the fluorescence of the SWNT). After the animal had healed from the SWNT placement a glucose tolerance test was performed to see if the implantation would react to glucose in vivo. FIG. 14 shows the glucose tolerance test results. At time point 0 glucose was injected IP and the mouse was imaged. A blood glucose meter was used to determine the mouse's blood glucose level and compare these reading to the fluorescence quenching. The trend of glucose concentration and fluorescence quenching were parallel.

Figure 15:
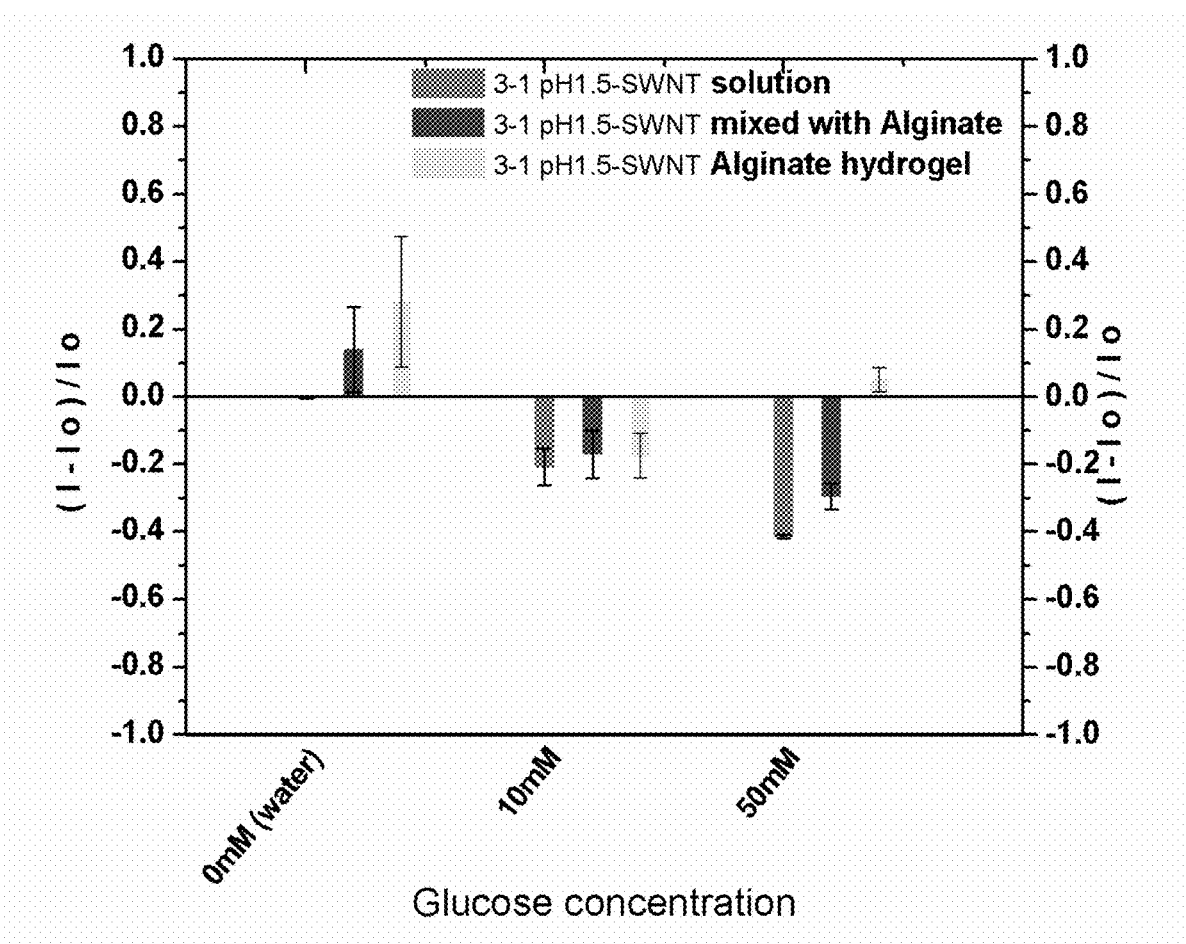
FIG. 15 is a graph depicting comparison of reaction ability of SWNT to glucose in solution, mixed with alginate, or in alginate hydrogel.

To encapsulate the SWNT sensor in the form of hydrogel matrices for its implantation, alginate was used as an encapsulating material for hydrogels. Alginate is an anionic polysaccharide and it is widely used in pharmaceutical applications due to its biocompatibility and simple gelation steps. Here the gel was created by crosslinking the mixture of Alginate and the SWNT solution. FIG. 15 shows the summary of the responses to glucose. By comparing the red bar and the blue bar graph, it is clear that the SWNT sensor does retain its ability to react to glucose even after mixed with alginate. Although there were some fluctuations of the signal upon the addition of water, the overall response was similar to the one of SWNT solution. However, as the alginate-SWNT mixture was crosslinked using Barium Chloride, the SWNT sensor completely lost its ability to react to glucose.

Hydrogel Characterization

Figure 23:
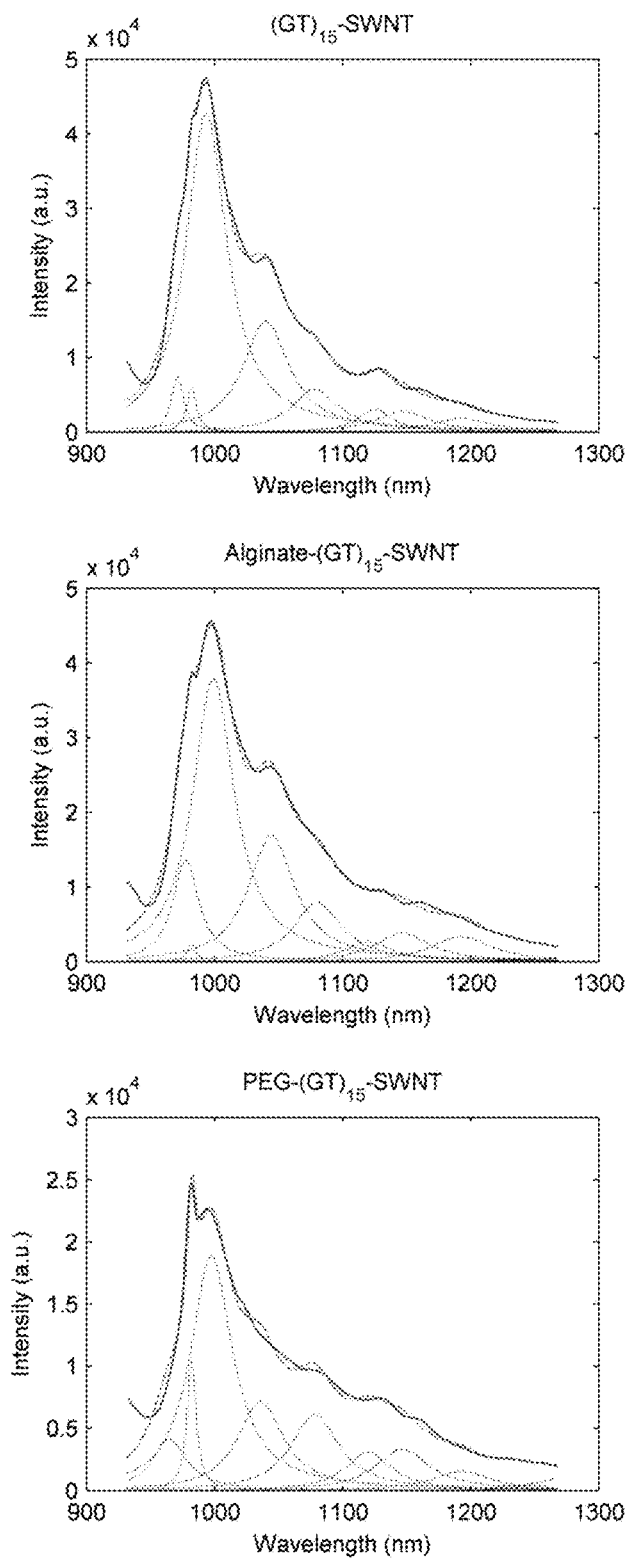
FIG. 23 is deconvolution of the fluorescent spectra of (GT)$_{15}$-SWNT (SEQ ID NO: 2), alginate-(GT)$_{15}$-SWNT (SEQ ID NO: 2), and PEG-(GT)$_{15}$-SWNT (SEQ ID NO: 2), with 10 mg L$^{-1}$ SWNT concentration, to the various nanotubes chiralities confirming the results shown in FIG. 22.

Alginate and PEG hydrogel encapsulating (GT)$_{15}$-SWNT (SEQ ID NO: 2) of various concentration were prepared and crosslinked in a barium chloride bath or by UV illumination, respectively (FIG. 16). The fluorescent signals of the (GT)$_{15}$-SWNT (SEQ ID NO: 2), alginate-(GT)$_{15}$-SWNT (SEQ ID NO: 2) and PEG-(GT)$_{15}$-SWNT (SEQ ID NO: 2) with 2 seconds exposure are shown in FIG. 1b. The spectra were deconvoluted to the different SWNT chiralities (FIG. 23) and the peak values of the fluorescence signal of the (6,5) tubes are summarized in FIG. 16C. The fluorescent signal linearly increases with increasing concentration (dotted lines in FIG. 16C) and plateaus above 10 mg L$^{-1}$ for the SWNT sample, whereas for the PEG-(GT)$_{15}$-SWNT (SEQ ID NO: 2) and alginate-(GT)$_{15}$-SWNT (SEQ ID NO: 2) hydrogel, the 25 mg L$^{-1}$ samples show a decrease in the fluorescence emission. For all the concentration tested, the alginate gels show brighter signal compared to the PEG hydrogels. Moreover, the (6,5) peak fluorescence of the alginate and PEG gels is red shifted (by 2-6 nm) compared to the SWNT samples (FIG. 16D).

Figure 16A:
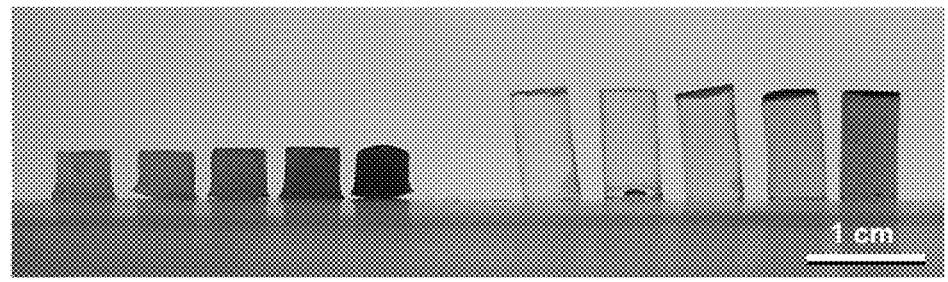
FIG. 16A is an image of the alginate (left) and PEG (right) hydrogels with increasing SWNT concentration of 0, 2, 5, 10, and 25 mg L$^{-1}$ (left to right) showing consistent size and shape of gels.
Figure 16B:
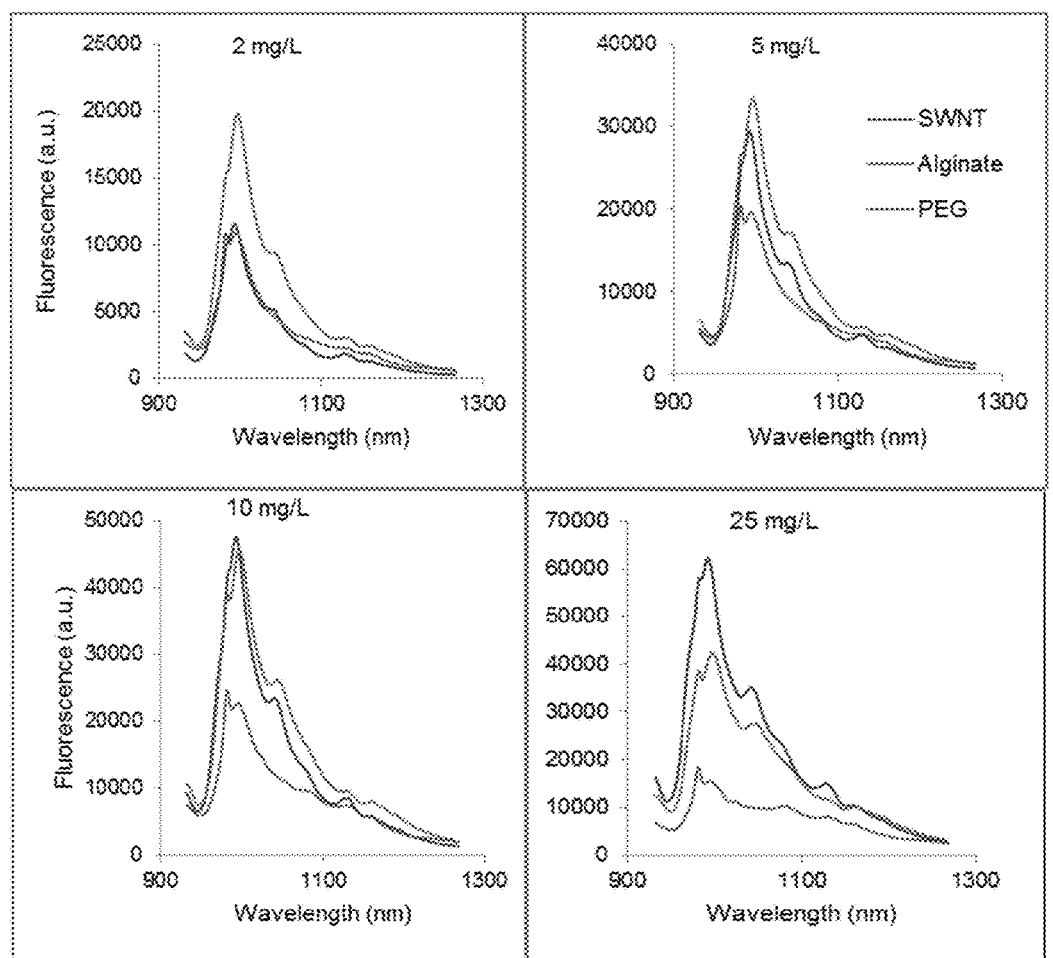
FIG. 16B is fluorescent emission spectra of (GT)$_{15}$-SWNT (SEQ ID NO: 2) solution (blue), alginate-(GT)$_{15}$-SWNT (SEQ ID NO: 2) (red), and PEG-(GT)$_{15}$-SWNT (SEQ ID NO: 2) (green) for concentration of 0, 2, 5, 10, and 25 mg L$^{-1}$.
Figure 16C:
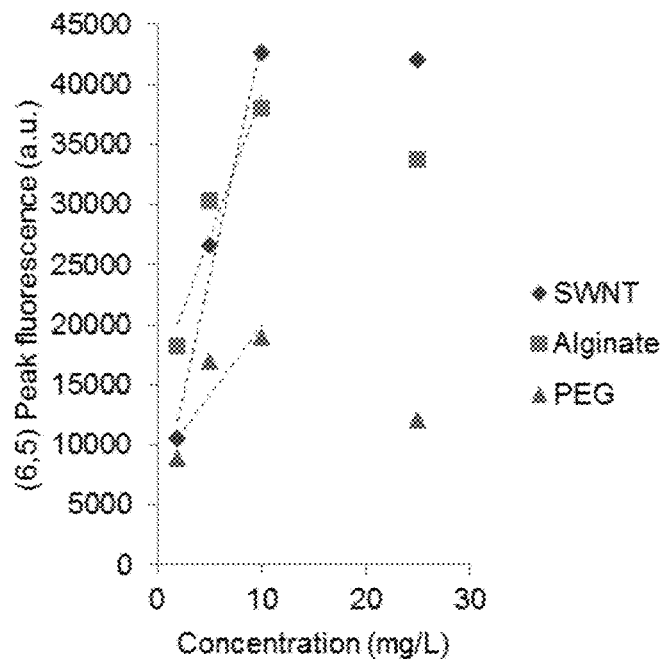
FIG. 16C is the peak fluorescence of the (6,5) chirality (GT)$_{15}$-SWNT (SEQ ID NO: 2) (blue), alginate-(GT)$_{15}$-SWNT (SEQ ID NO: 2) (red), and PEG-(GT)$_{15}$-SWNT (SEQ ID NO: 2) (green) showing the increase in SWNT fluorescence for the lower concentrations 2, 5 and 10 mg L$^{-1}$, dotted line is linear fit, but a drop in fluorescence at the higher concentration (25 mg L$^{-1}$).
Figure 16D:
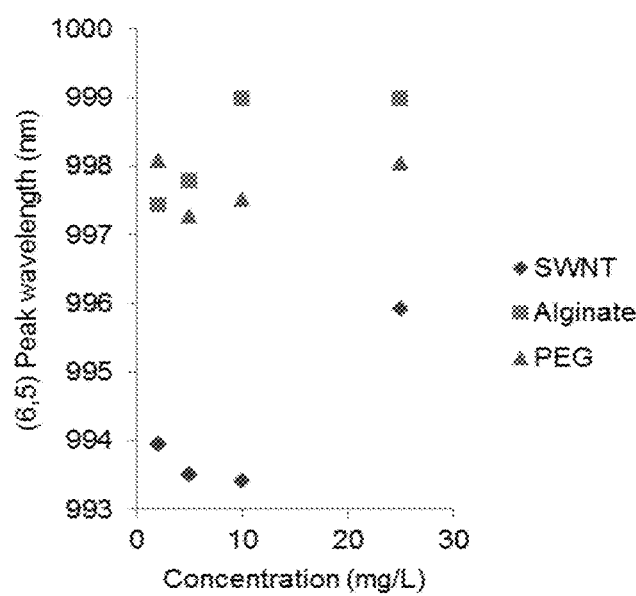
FIG. 16D is the wavelength corresponding to the (6,5) chirality peak fluorescence of (GT)$_{15}$-SWNT (SEQ ID NO: 2) (blue), alginate-(GT)$_{15}$-SWNT (SEQ ID NO: 2) (green), and PEG-(GT)$_{15}$-SWNT (SEQ ID NO: 2) (red) showing a red shift for the hydrogels when compared to the non-encapsulated SWNT signal.
Figure 17A:
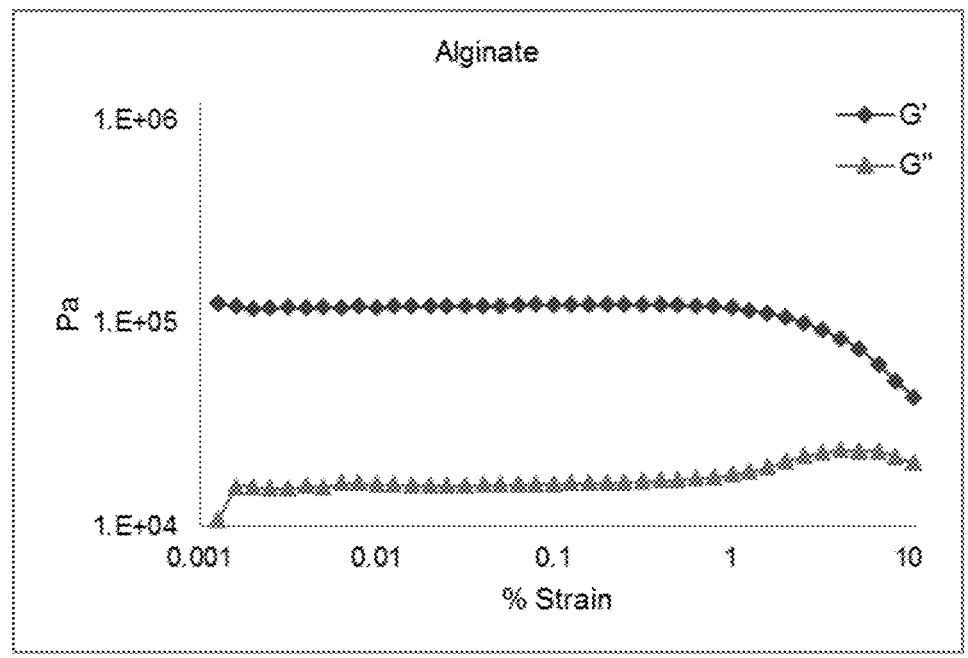
FIGS. 17A-17D show is rheological properties of the alginate and PEG hydrogel.
Figure 17B:
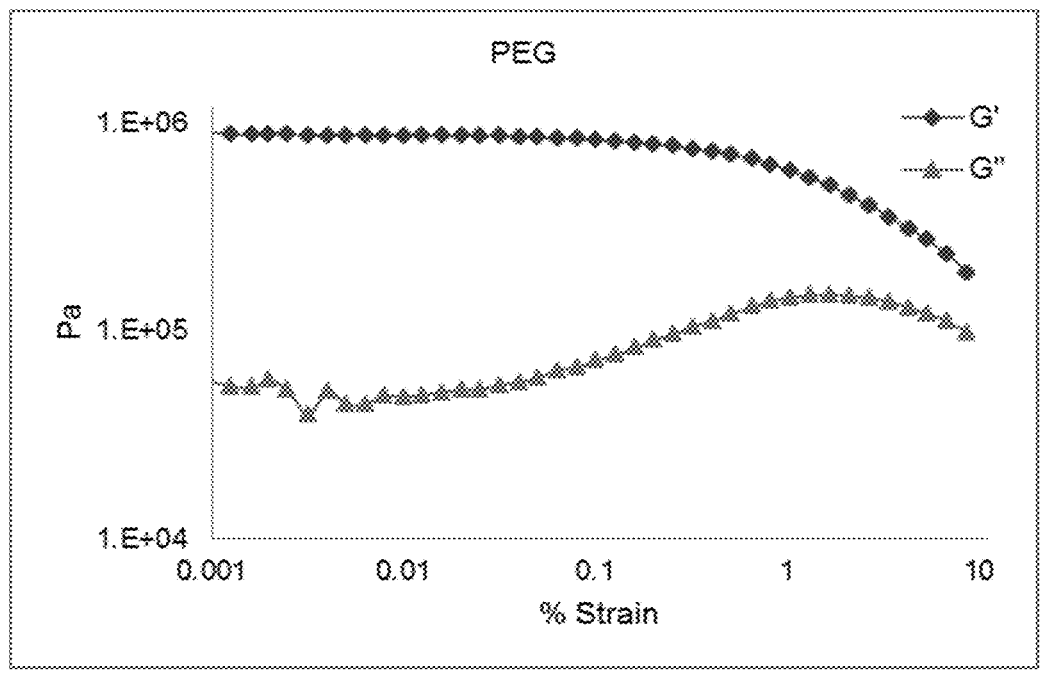
Figure 17C:
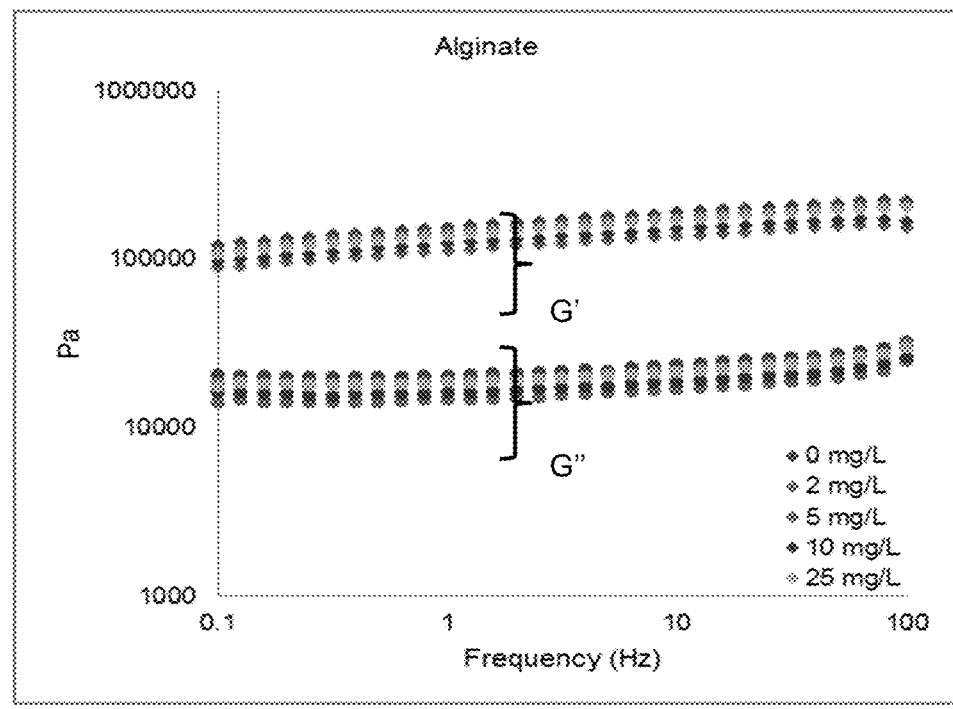
Figure 17D:
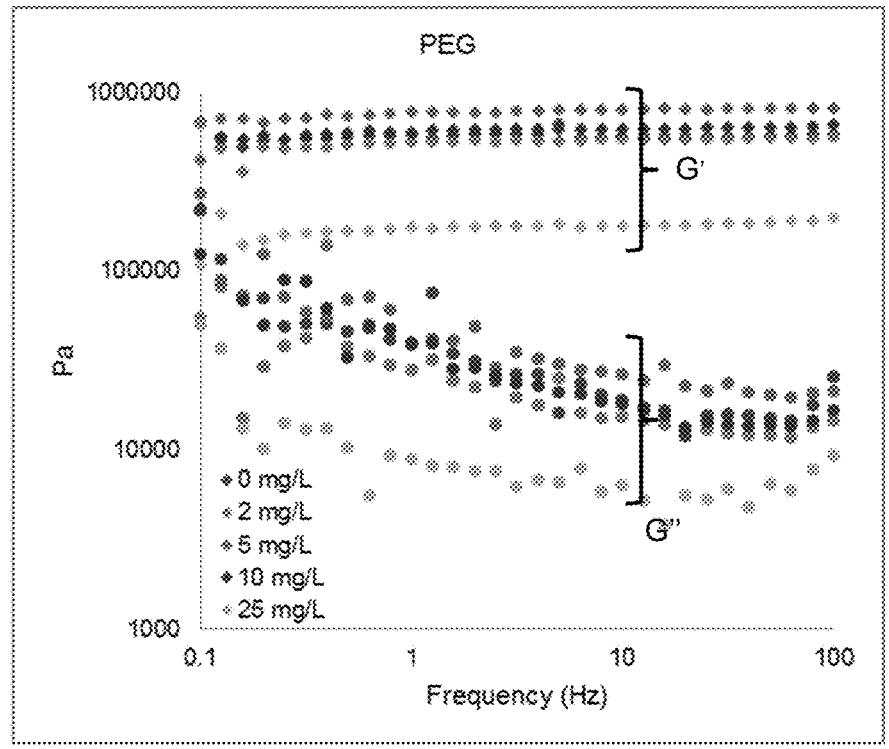

The Rheological properties of the alginate and PEG gels were determined by oscillatory measurements with parallel plate geometry. The linear viscoelastic region (LVR) of the hydrogels without nanoparticles was assessed by a strain sweep with a constant 1 Hz frequency. The storage (G') and loss (G") moduli as a function of the strain percentage are presented in FIGS. 17A and 17B for alginate and PEG respectively. The viscoelastic responses of the gels without nanoparticles and with 2, 5, 10, and 25 mg L$^{-1}$ SWNT were evaluated by a frequency sweep in the LVR, at constant 0.1% and 0.01% strain for alginate and PEG respectively (FIGS. 16C and 16D). The G' values were approximately an order of magnitude larger the G" values for all cases. Moreover, the viscoelastic properties did not vary much with respect to the concentration of the encapsulated nanoparticles, with an exception of the PEG hydrogel with the highest SWNT concentration (25 mg L$^{-1}$), which had much lower storage modulus relative to lower concentrations. This can be attributed to the high absorption of the SWNT in the UV region which might interfere with the UV-initiated crosslinking process in this case.

The crosslinking density $\rho_x$ can be estimated from the storage modulus (G') of the hydrogels using the rubber elasticity theory[41-43]:

$$G' = \rho_x RT \quad (1)$$

where R is the gas constant and T is the temperature. Using the G' value in the LVR regions (FIGS. 16A and 16B) the crosslinking density of alginate and PEG hydrogels were 48 mol m$^{-3}$ and 363 mol m$^{-3}$, suggesting an average distance of 3.2 nm and 1.7 nm between crosslinks, respectively. Although the theory of rubber elasticity was developed for chemically crosslinked hydrogels[43], such as PEG, equation (1) can be applied to alginate, which is physically crosslinked, under certain conditions such as insignificant dependence of the storage modulus G' on the frequency, and low loss ratio (G'/G")[44], which hold in our case.

Figure 18A:
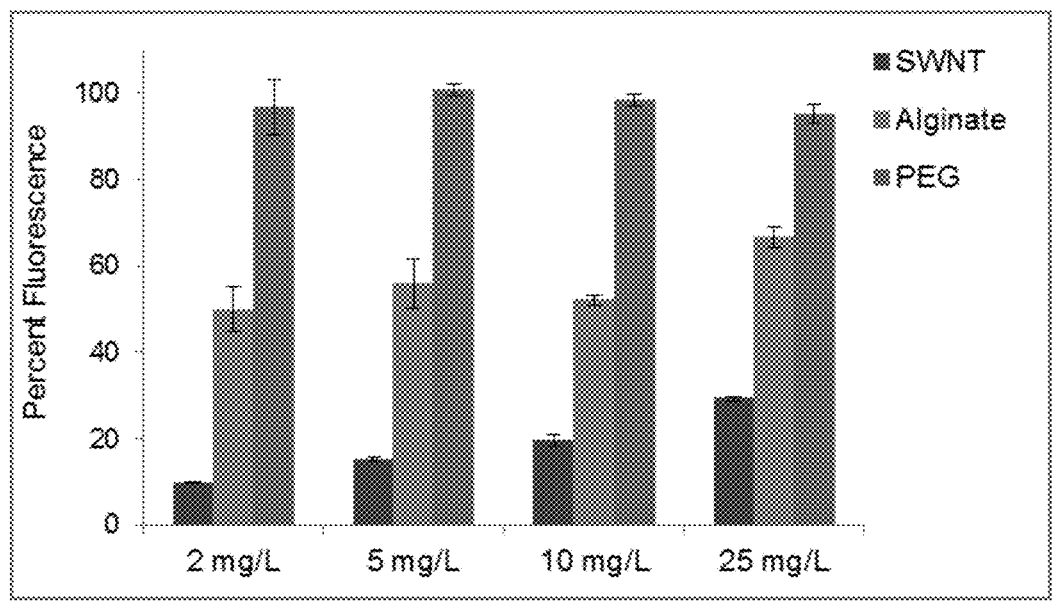
FIG. 18A is fluorescence signal quenching of (GT)$_{15}$-SWNT (SEQ ID NO: 2) (blue), alginate-(GT)$_{15}$-SWNT (SEQ ID NO: 2) (red), and PEG-(GT)$_{15}$-SWNT (SEQ ID NO: 2) (green), measured in the nIR array following 1 hour incubation with riboflavin showing consistent quenching of the SWNT suspension and of alginate encapsulated SWNT, but the lack of signal quenching for PEG encapsulated samples.

Encapsulated Nanoparticles Fluorescence Quenching in Various Hydrogel Geometries In order to simulate and characterize an encapsulated nanoparticle sensor, the fluorescent modulation of the (GT)$_{15}$-SWNT (SEQ ID NO: 2), PEG-(GT)$_{15}$-SWNT (SEQ ID NO: 2) and alginate-(GT)$_{15}$-SWNT (SEQ ID NO: 2) in response to the addition of riboflavin was measured in the nIR array and presented in FIG. 18A. Riboflavin was chosen as a model target analyte since it is a known fluorescent quencher of DNA-wrapped SWNT. See, Zhang, J. et al. Molecular recognition using a corona complex made of artificial polymers adsorbed on carbon nanotubes. *Nature Nanotechnology* 8, 959-968 (2013), and Zhang, J. Q. et al. Single Molecule Detection of Nitric Oxide Enabled by d(AT)(15) (SEQ ID NO: 3) DNA Adsorbed to Near Infrared Fluorescent Single-Walled Carbon Nanotubes. *Journal of the American Chemical Society* 133, 567-581 (2011), each of which is incorporated by reference in its entirety. Following incubation of 1 hour, the signal of the SWNT solutions quenched by 90%, 85%, 80% and 70% for the 2, 5, 10, and 25 mg L$^{-1}$ concentrations, respectively, while the alginate hydrogel were quenched by 50%, 44%, 48% and 33%, respectively. The PEG hydrogels showed less than 5% change for all concentrations, where longer incubation times of up to 6 hours showed no significant change (data not shown).

Figure 18B:
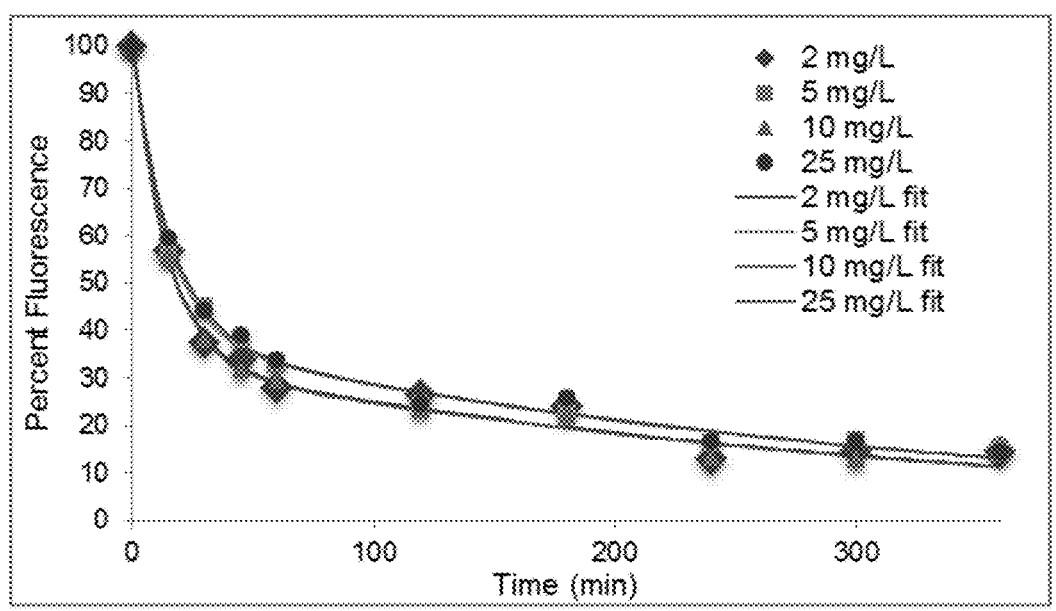
FIGS. 18B-18D are comparison of percent SWNT fluorescence quenching for alginate-(GT)$_{15}$-SWNT (SEQ ID NO: 2) during 6 hr of riboflavin exposure, measured on the whole animal imaging system, showing that changing the concentration (FIG. 18B), size (FIG. 18C) and shape/surface area (FIG. 18D) have little effect on the quenching rate.

The effect of nanoparticles concentration was investigated by studying the quenching of the alginate hydrogels with 2, 5, 10 and 25 mg L$^{-1}$ concentrations over a 6 hour period. Two characteristic quenching time scales were found using a bi-exponential fit (FIG. 18B), where the short being 14.2, 14.5, 14.1, and 15.4 minutes, and the long being 6.18, 5.6, 5.8, and 5.7 hours for the 2, 5, 10, and 25 mg L$^{-1}$ concentrations, respectively. Although the initial intensities varied between the four concentrations, the quenching rates were similar for all suggesting a common mechanism.

Figure 18C:
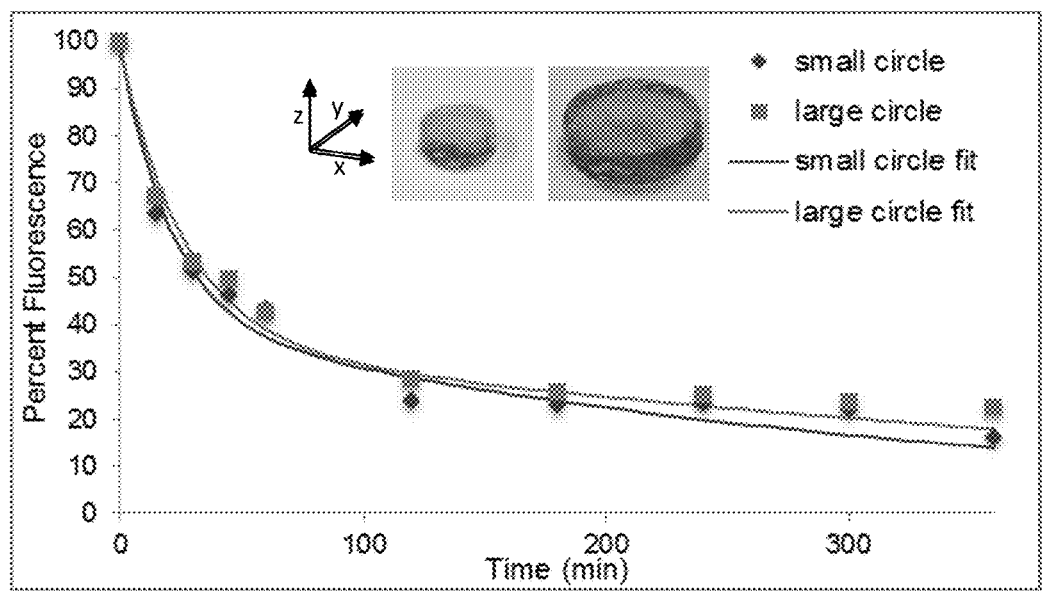

The effects of the gel geometry on the quenching rate and extent were studied with the alginate-(GT)$_{15}$-SWNT (SEQ ID NO: 2) system, with nanoparticles concentration of 10 mg L$^{-1}$. The fluorescent signal of circle shaped alginate gels of volumes 200 μl and 600 μl was monitored for 6 hours (FIG. 18C). Both the small (200 uL) and large (600 uL) circle gels showed two characteristic quenching times in a bi-exponential fit, one of which was of the order of 20 minutes (20.7 and 26.2 min, respectively), where the second was of the order of several hours (6.5 and 10.8 hr, respectively). The comparable time scales demonstrate that minimizing the base surface area of the get has a minor effect on increasing the quenching rate for a fixed gel height (3 mm), given that it is small relative to the gel diameter (7 mm and 15 mm, respectively).

For the star, rectangle, and circle shaped gels, all with identical volume, the long characteristic quenching times in a bi-exponential fit (FIG. 18D) were 15.6, 9.9, and 9.5 hours, respectively, showing a slight decrease for smaller lateral surface area. The short characteristic quenching times were comparable for all shapes, being 34.9, 19.3, and 26.8 minutes for the star, rectangle, and circle shaped gels, respectively. These results indicate that for gels in this size range, there are no mass transfer limitations at the gel surface (shape invariance) and no internal mass transport limitations (size invariance).

Chemical Stability of the Hydrogels

Figure 19A:
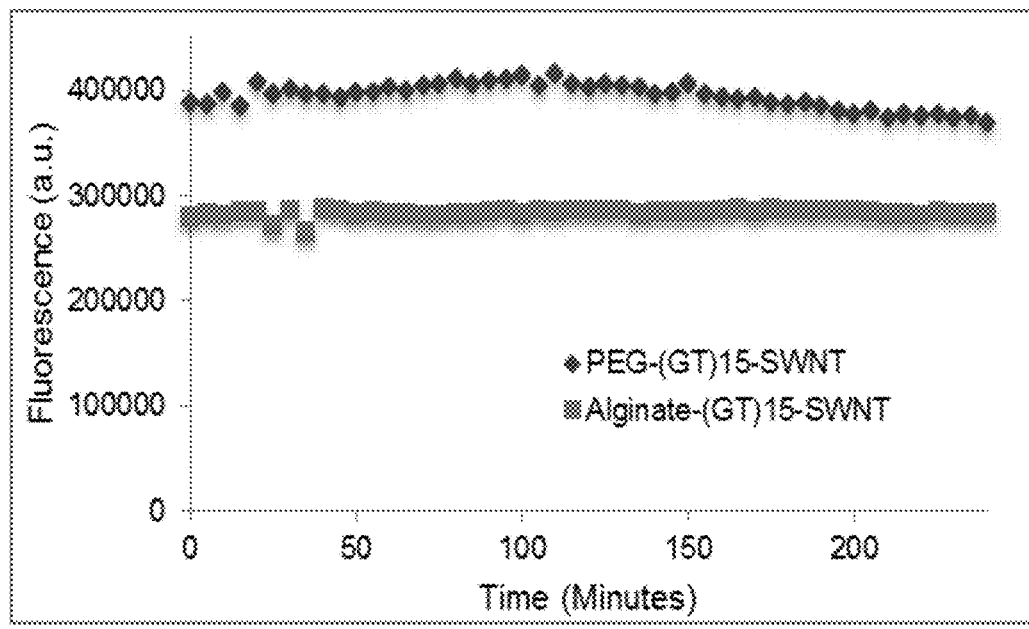
FIG. 19A is short term stability testing of alginate-(GT)$_{15}$-SWNT (SEQ ID NO: 2) (blue) and PEG-(GT)$_{15}$-SWNT (SEQ ID NO: 2) (red) showing no photobleaching when exposed to laser light for 4 hr. Scale bars=2 mm.
Figure 19A:
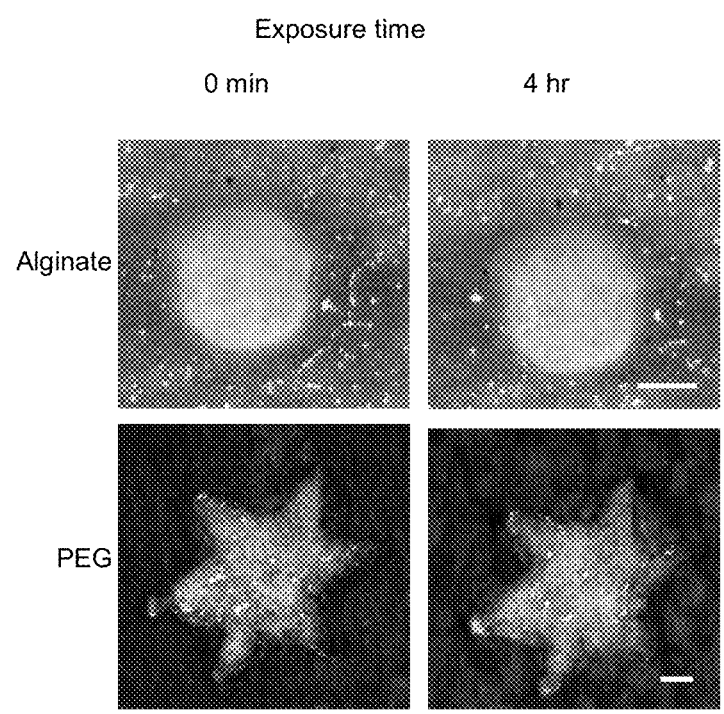

The photothermal and photochemical stability of the two hydrogel model systems was tested by monitoring the fluorescent signal of the encapsulated nanoparticles over time. Since SWNT exhibit no photobleaching (see Liu, Z., Tabakman, S., Welsher, K. & Dai, H. Carbon Nanotubes in Biology and Medicine: In vitro and in vivo Detection, Imaging and Drug Delivery. *Nano Research* 2, 85-120 (2009), Cherukuri, P., Bachilo, S. M., Litovsky, S. H. & Weisman, R. B. Near-infrared fluorescence microscopy of single-walled carbon nanotubes in phagocytic cells. *Journal of the American Chemical Society* 126, 15638-15639 (2004), and Graff, R. A. et al. Achieving individual-nanotube dispersion at high loading in single-walled carbon nanotube composites. *Advanced Materials* 17, 980-984 (2005), each of which is incorporated by reference in its entirety), their fluorescence served as an indicator for the degradation of the hydrogel matrix. The gels were imaged for 4 hours under continuous laser excitation of 14 mW at focal plane, with image collection at 5 minutes intervals. The stability of the signal can be clearly seen in FIG. 19A for both the alginate and the PEG gels (SWNT at 10 mg L$^{-1}$) when the samples remained moist during testing. However, when the samples were dried out, they irreversibly lost their shape and fluorescence, which did not recover upon rehydration.

Figure 19B:
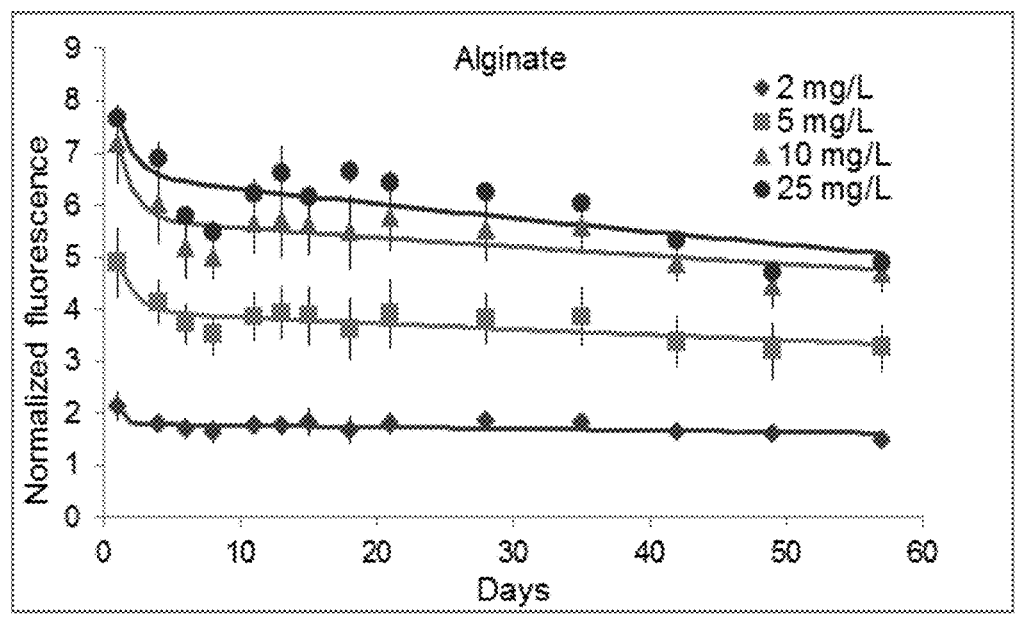
FIG. 19B is long term stability of alginate-(GT)$_{15}$-SWNT (SEQ ID NO: 2) gels showing good fluorescence signal retention over the 90 day testing period. Solid lines represent bi-exponential fit.
Figure 19C:
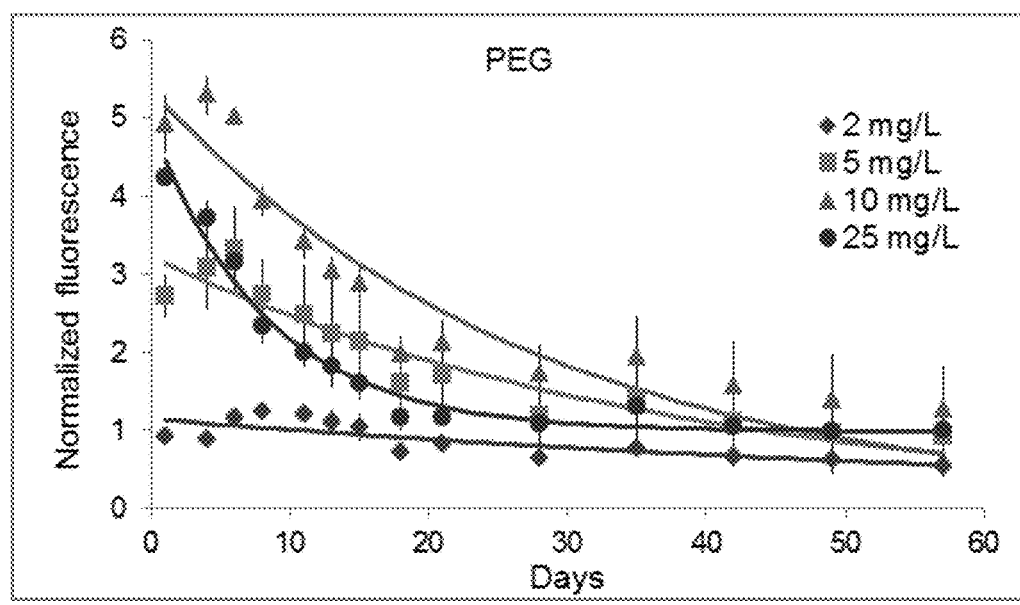
FIG. 19C is PEG-(GT)$_{15}$-SWNT (SEQ ID NO: 2) gels experience fluorescence signal loss shortly after synthesis. Solid lines represent bi-exponential fit.

For assessing the long-term chemical stability of the nanoparticle encapsulated gels, both alginate and PEG hydrogels with encapsulated SWNT at different concentrations were analyzed for 60-90 days in the whole animal and nIR array imaging systems. The peak fluorescence of the alginate and PEG hydrogel plugs was measured at multiple time points in the nIR array with SWNT concentration of 2, 5, 10 and 25 mg L$^{-1}$, and was normalized by the peak fluorescent signal of a standard SWNT suspension that was measured each time in the same condition of the gels. The data points of the PEG and alginate gels were fitted by an exponential and bi-exponential decay models, respectively, showing one and two characteristic decay time scales respectively (FIGS. 19B and 19C). The characteristic decay times of the gels are presented in FIG. 19E and show a fast decay ($t_1$) of the order of 1 day for alginate gels, and a slower decay ($t_2$) which is of the order of 2 years in the case of the alginate gels, and between 10-100 days in the case of the PEG hydrogels. The short decay time scale of the alginate gel can be attributed to swelling in the 96-well plate used for imaging until equilibrium is reached which is typically achieved within 24 hours, whereas PEG-diacrylate gels have shown to reach equilibrium within approximately 20 minutes. See, Davidovich-Pinhas, M. & Bianco-Peled, H. A quantitative analysis of alginate swelling. *Carbohydrate Polymers* 79, 1020-1027, and Mellott, M. B., Searcy, K. & Pishko, M. V. Release of protein from highly cross-linked hydrogels of poly(ethylene glycol) diacrylate fabricated by UV polymerization. *Biomaterials* 22, 929-941, each of which is incorporated by reference in its entirety. The long degradation time scale of the hydrogels is mainly due to hydrolysis in the case of PEG, and diffusion of the divalent cations in the case of alginate. See, Reid, B. et al. PEG hydrogel degradation and the role of the surrounding tissue environment. *Journal of Tissue Engineering and Regenerative Medicine*, n/a-n/a, doi:10.1002/term.1688 (2013), Lin, C.-C. & Anseth, K. PEG Hydrogels for the Controlled Release of Biomolecules in Regenerative Medicine. *Pharm Res* 26, 631-643, (2009), Metters, A. T., Bowman, C. N. & Anseth, K. S. A Statistical Kinetic Model for the Bulk Degradation of PLA-b-PEG-b-PLA Hydrogel Networks. *The Journal of Physical Chemistry B* 104, 7043-7049, (2000), Lee, K. Y., Bouhadir, K. H. & Mooney, D. J. Controlled degradation of hydrogels using multi-functional cross-linking molecules. *Biomaterials* 25, 2461-2466 (2004), and Kong, H. J., Kaigler, D., Kim, K. & Mooney, D. J. Controlling Rigidity and Degradation of Alginate Hydrogels via Molecular Weight Distribution. *Biomacromolecules* 5, 1720-1727, (2004), each of which is incorporated by reference in its entirety.

Figure 19D:
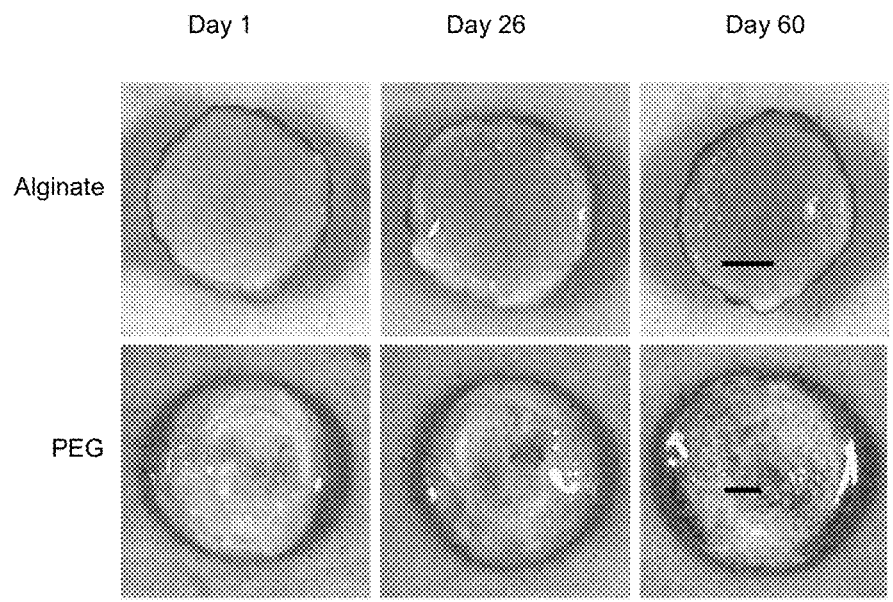
FIG. 19D is images of alginate-(GT)$_{15}$-SWNT (SEQ ID NO: 2) and PEG-(GT)$_{15}$-SWNT (SEQ ID NO: 2) acquired on the whole animal imaging system showing the gels' retention (alginate) or loss (PEG) of signal over time. Scale bars=2 mm.
Figure 19E:
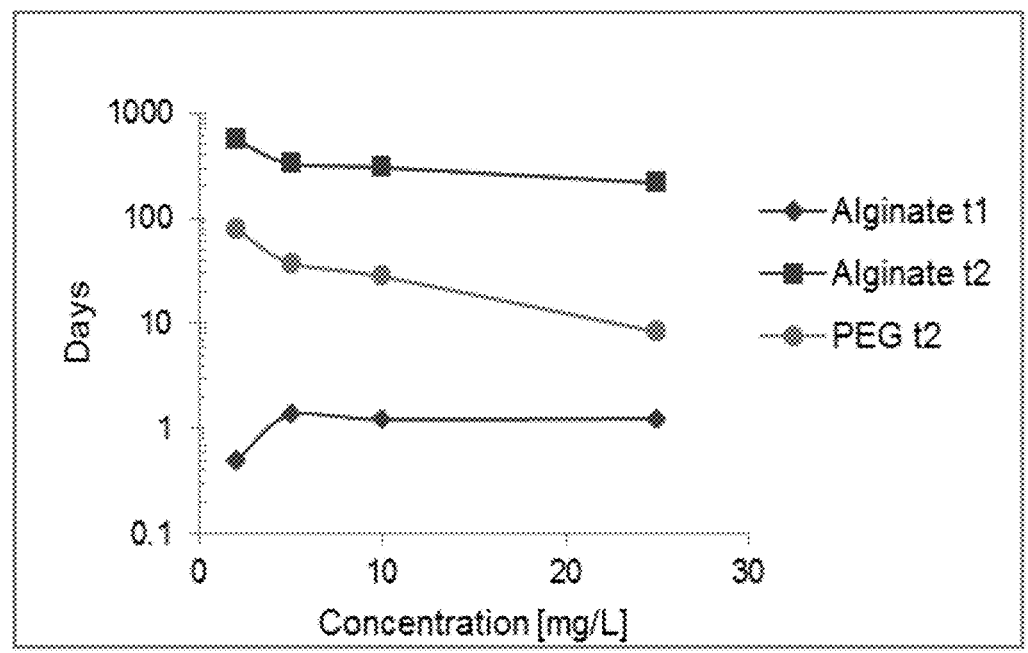
FIG. 19E is shelf life of alginate and PEG gels estimated by the fit function of FIGS. 19B and 19C corresponding to the observed longevity and breakdown of alginate and PEG hydrogels respectively.
Figure 24:
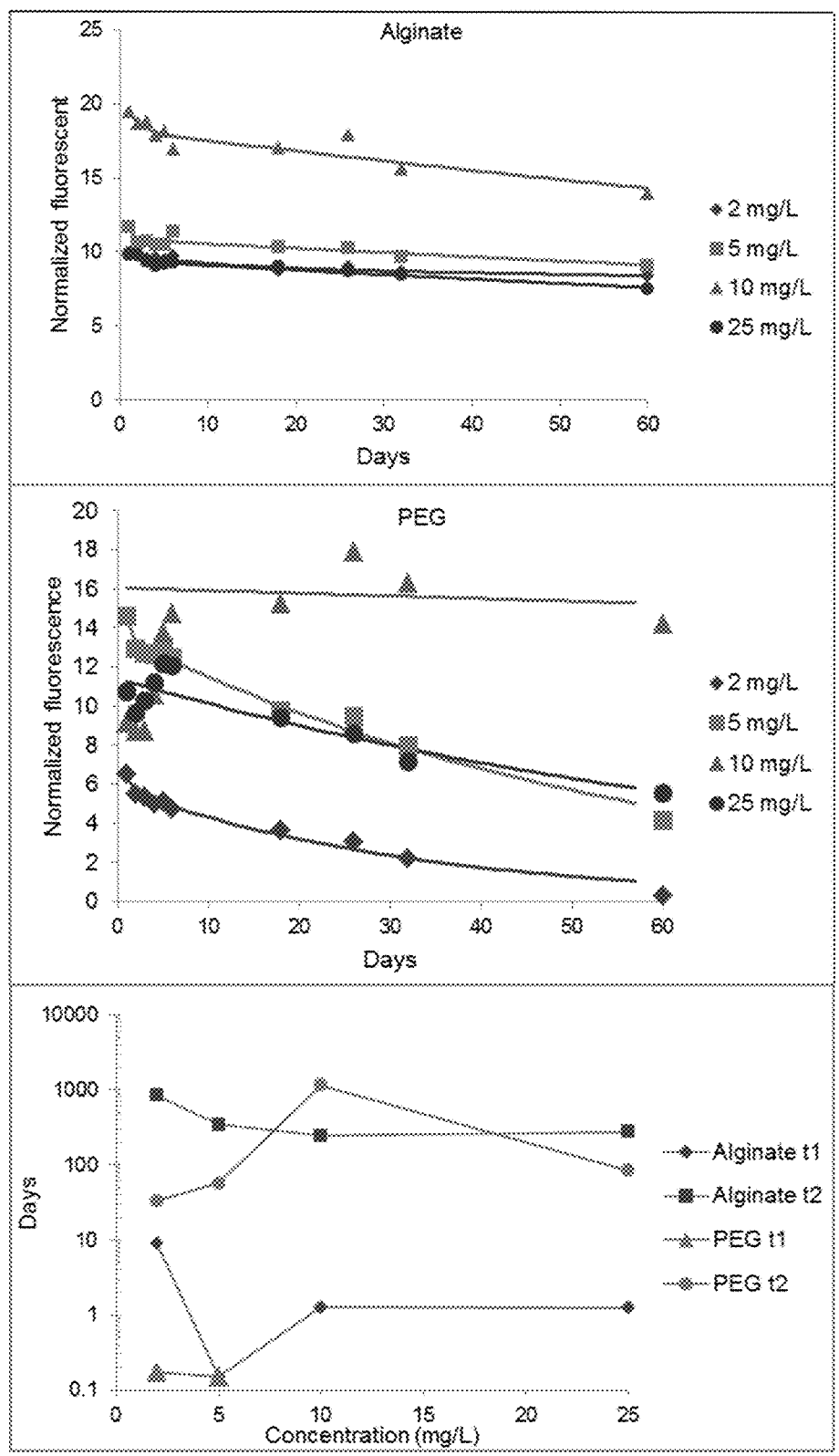
FIG. 24 is data for long term shelf life analysis from the whole animal imaging system—parallel study and results to that seen in FIG. 19.

In addition, according to the whole animal imaging system, which integrates the fluorescent signal in the range of 950-1050 nm, the alginate gels better retained their shape and their fluorescence over the entire test period while the PEG gels lost both their fluorescence and their shape over time (FIG. 19D and FIG. 24).

Detection Depth Limit

In order to estimate the maximal detection depth within tissue, the nanoparticles fluorescent signal was collected thought tissue phantom samples. Assuming a one dimensional absorption and scattering model, for a hydrogel imaged through tissue of thickness d, the detected fluorescence intensity F is:

$$F = AI_0\rho\phi e^{-(\mu_{ex}+\mu_{em})d} \quad (2)$$

where $I_0$ is the excitation laser intensity, $\mu_{ex}$ and $\mu_{em}$ are the tissue extinction coefficients for the excitation and emission wavelengths, respectively, $\rho$ is the fluorescent nanoparticles concentration in the hydrogel, $\phi$ is the quantum yield, and A is a proportional constant.

Figure 20A:
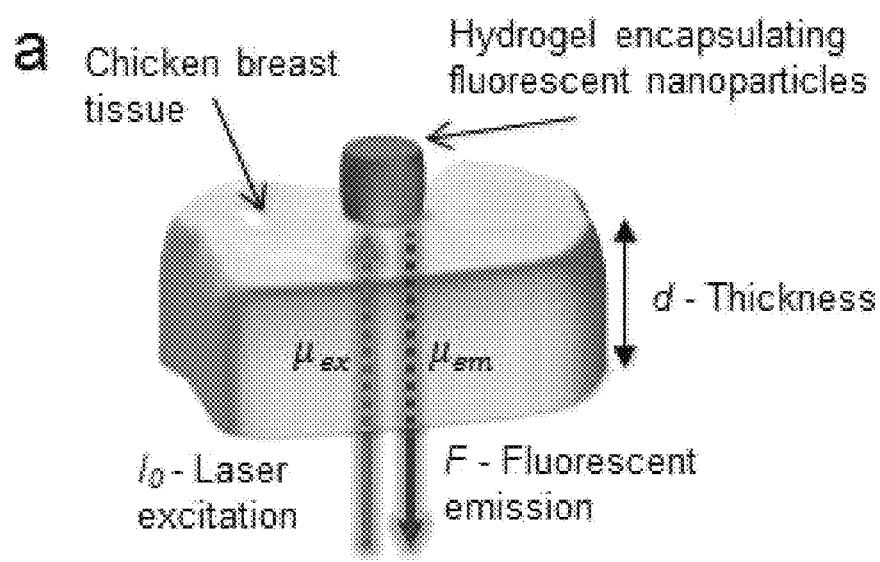
FIG. 20A is illustration of the tissue spectroscopy measurement setup for nIR analysis.
Figure 20B:
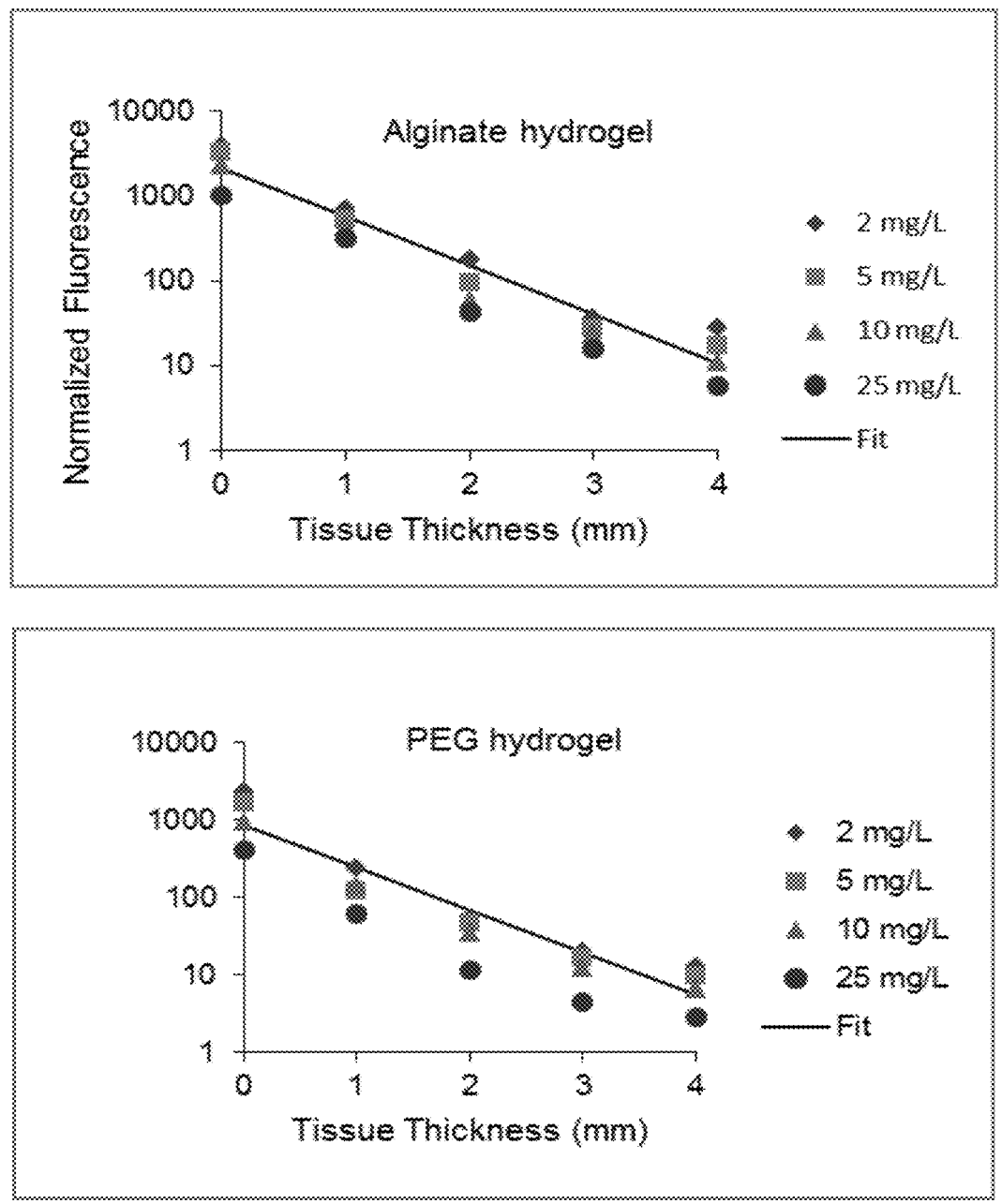
FIGS. 20B and 20C are normalized fluorescent signal of alginate and PEG gels imaged through chicken breast tissue with in house nIR array (FIG. 20B) and whole animal imaging systems (FIG. 20C).

(GT)$_{15}$-SWNT (SEQ ID NO: 2) encapsulated within PEG and alginate hydrogels were imaged through chicken breast tissue of various thicknesses (FIG. 20A). The normalized fluorescent signal measured by the nIR array of the alginate-(GT)$_{15}$-SWNT (SEQ ID NO: 2) and the PEG-(GT)$_{15}$-SWNT (SEQ ID NO: 2) as a function of the tissue thickness is presented in FIG. 5b for the various concentrations used in this study. The fluorescent intensity was evaluated at the (6,5) chirality emission peak normalized by the SWNT concentration and the exposure time such that the data points would collapse to a single curve, assuming linear dependence of the fluorescent signal on the exposure time. Since the fluorescent intensity is linearly dependent on the SWNT concentration only up to 10 mg L$^{-1}$, only the results for the 2, 5, and 10 mg L$^{-1}$ were fitted by an exponential decay function. The absolute values of the exponent coefficients were 1.325±0.095 mm$^{-1}$ and 1.257±0.103 mm$^{-1}$ for the alginate and PEG gels respectively.

For determining the maximal detection depth, a detection limit was defined to be three times the root mean square of the background noise signal of the nIR array imaging system, and maximal exposure time of 30 seconds. The calculation was done based on the exponential fit function for the 2, 5, and 10 mg L$^{-1}$ SWNT concentrations. The detection limits are summarized in Table 1.

TABLE 1

Detection limit for the alginate and PEG hydrogel systems determined by the exponential fit function (Equation (2)) for the three lower concentration of nanoparticles encapsulated within the hydrogels.

|  | 2 mg L$^{-1}$ | 5 mg L$^{-1}$ | 10 mg L$^{-1}$ |
| --- | --- | --- | --- |
| Alginate | 4.1 mm | 4.8 mm | 5.4 mm |
| PEG | 3.8 mm | 4.5 mm | 5.1 mm |

Figure 21A:
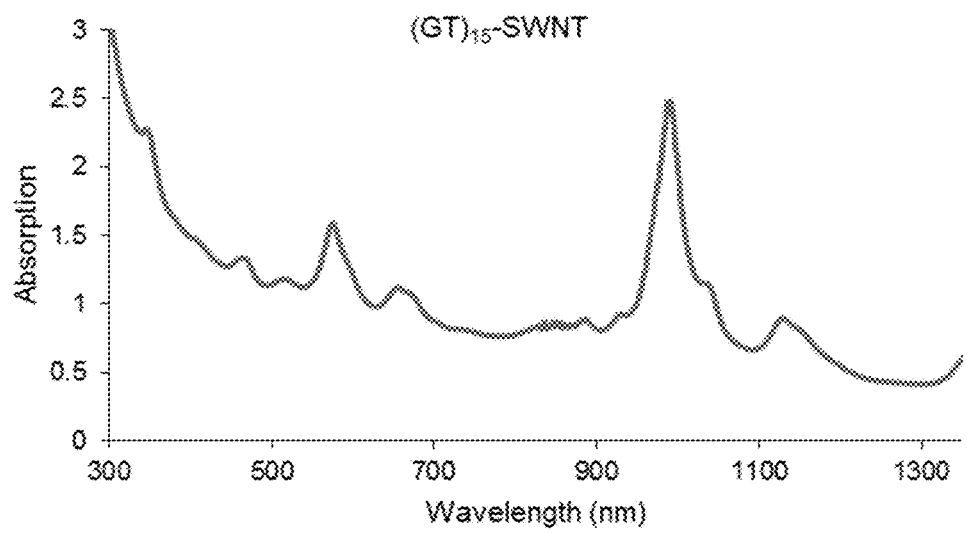
FIGS. 21A-21B are absorption spectra of (GT)$_{15}$-SWNT (SEQ ID NO: 2) (FIG. 21A) and chicken breast (FIG. 21B).
Figure 21B:
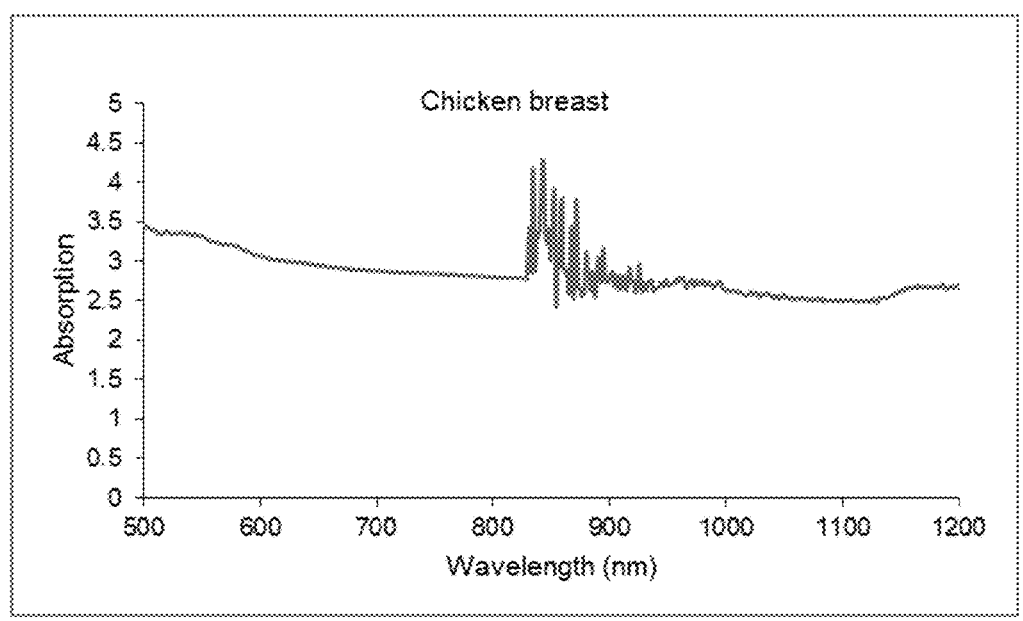
Figure 22:
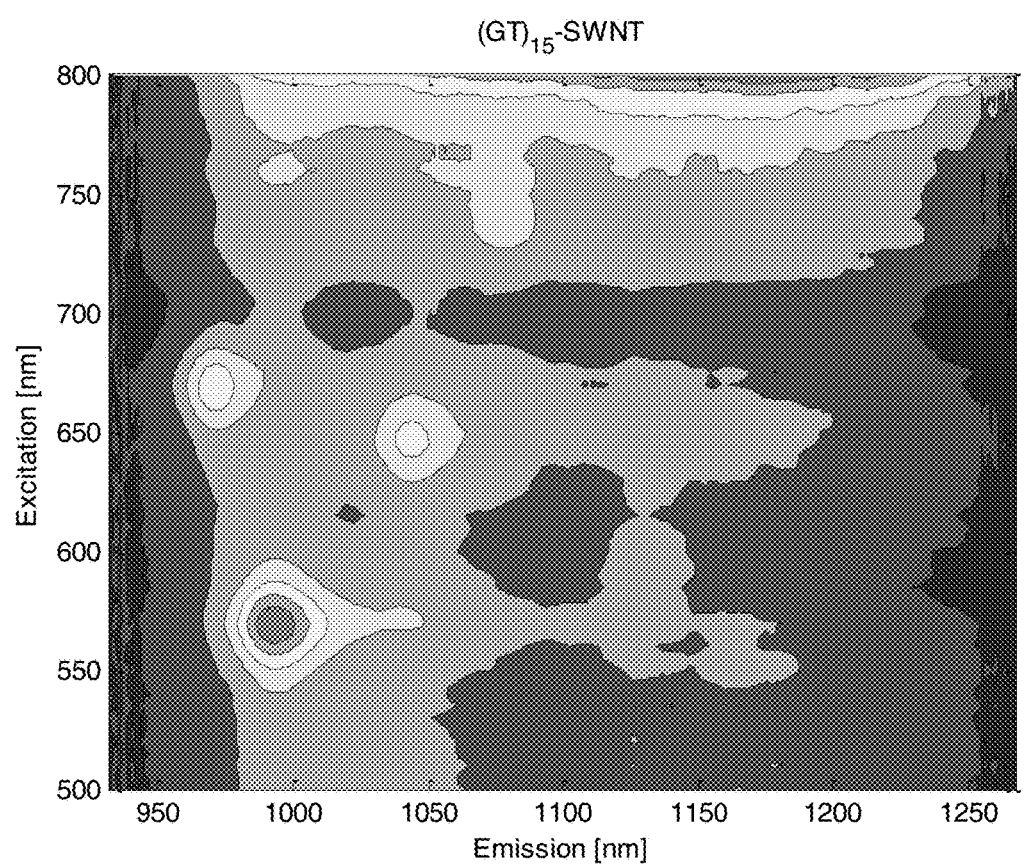
FIG. 22 is (GT)$_{15}$-SWNT (SEQ ID NO: 2) excitation-emission profile shows large concentration of (6,5) SWNT, corresponding to the prominent 996 nm peak.

According to the 1D model presented in equation (2), the exponential coefficient is equal to the sum of the extinction coefficients of the excitation and emission wavelengths, which were evaluated independently by measuring the absorption spectrum of chicken breast tissue (FIG. 21B) in the corresponding spectral range. The sum of the extinction coefficients corresponding to the excitation laser wavelength (785 nm) and the emitted fluorescence wavelength (996 nm) was 2.121±0.022 mm$^{-1}$ according to the spectrum, which is comparable to the coefficients found in the exponential fit.

Figure 20C:
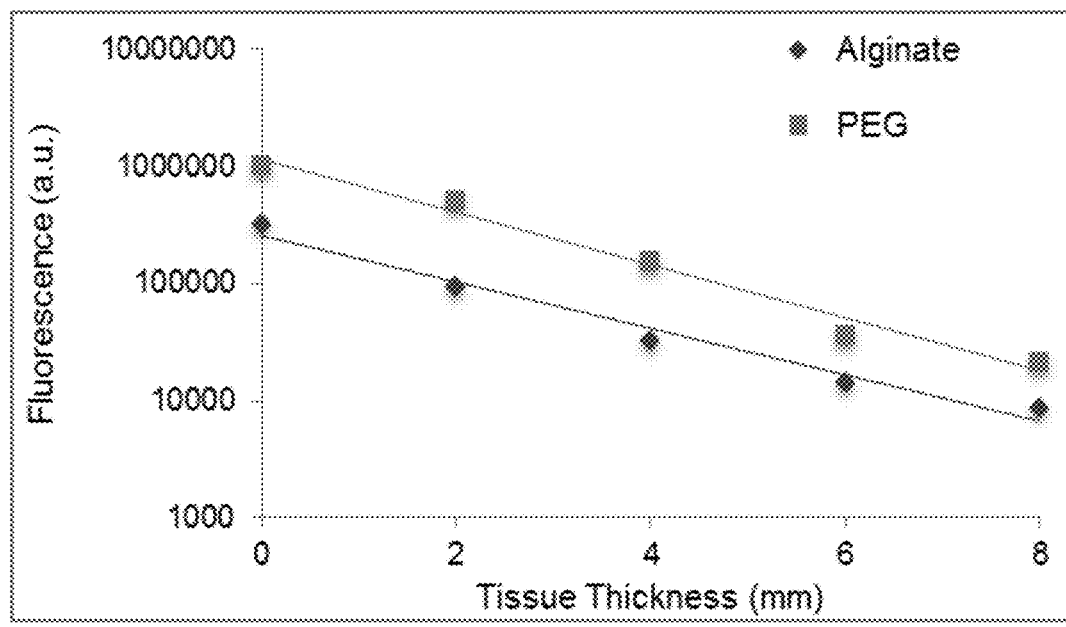

Maximum detection limit was further analyzed by imaging with the whole animal imaging system at depths of 2, 4, 6 and 8 mm. This data (FIG. 20C) confirmed the nIR results, showing a clear signal for 10 mg L$^{-1}$ gels at 2 and 4 mm depths, whereas the readings of 6 and 8 mm deep samples where comparable to the background noise of the instrument.

In Vivo Detection

Figure 20D:
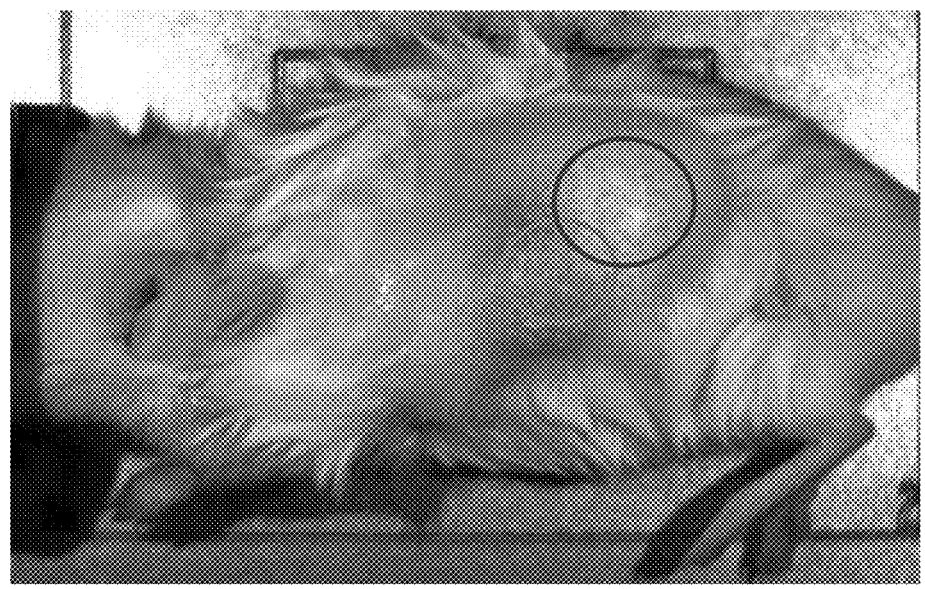
FIG. 20D is in vivo florescent imaging of (GT)$_{15}$-SWNT (SEQ ID NO: 2) encapsulated in PEG (red circle) and alginate (blue circle) gels 14 days post implantation, showing mice had no negative reactions to the gels and the fluorescence is clearly visible in live animal.

In order to ensure the viability of the gels in vivo, both PEG and alginate gels were implemented encapsulating the fluorescent nanoparticles in mice (n=3) and tested the fluorescent signal in the whole animal imaging system. As seen in FIG. 20D, both PEG and alginate gels were visible 14 days post implantation. Mice retained implants for 60 days and showed no adverse reactions to either hydrogel.

The relationship between tissue depth and signal detection in two types of hydrogels was analyzed by creating a model for future in vivo use of fluorescence sensors and determining the extent to which these gels can be utilized in vivo. A consistent and reproducible method for hydrogel fabrication of various geometries was developed. Alginate gels showed a much brighter fluorescent signal than their PEG counterparts, typically emitting 1.5 to 3 times more intense, and found an optimal nanoparticles concentration for both systems of 10 mg $L^{-1}$ in the case of SWNT, above which the fluorescent signal decreases. The encapsulated SWNT redshifted fluorescent signal, with respect to the SWNT fluorescence in aqueous suspension, indicates SWNT aggregation within the gel, which contributes to the decrease of the fluorescence emission in high concentration. See, O'Connell, M. J. et al. Band gap fluorescence from individual single-walled carbon nanotubes. *Science* 297, 593-596 (2002), which is incorporated by reference in its entirety. This effect must be taken under consideration in any system of hydrogel encapsulating fluorescent sensors, since increasing nanoparticles concentration can lead to self-quenching. See, Resch-Genger, U., Grabolle, M., Cavaliere-Jaricot, S., Nitschke, R. & Nann, T. Quantum dots versus organic dyes as fluorescent labels. *Nat Meth* 5, 763-775 (2008), which incorporated by reference in its entirety.

The alginate hydrogels are less stiff than their PEG counterparts and can sustain higher strain deformations before undergoing mechanical failure. The rigidity of the PEG gels may be a limiting factor for in vivo applications since natural tissue movement requires a compliant gel to avoid discomfort to the patient. Reducing the PEG concentration or shortening the duration of UV illumination for crosslinking can decrease rigidity, and improve the gel properties for in vivo applications.

Riboflavin, whose hydrodynamic radius is 0.58 nm, was used as a model target analyte as it quenches the fluorescent emission of the nanotubes encapsulated within the hydrogel. See, Tao, X. *Smart Fibres, Fabrics and Clothing*. (Woodhead Publishing, 2001), and Zhang, J. Q. et al. Single Molecule Detection of Nitric Oxide Enabled by d(AT)(15) (SEQ ID NO: 3) DNA Adsorbed to Near Infrared Fluorescent Single-Walled Carbon Nanotubes. *Journal of the American Chemical Society* 133, 567-581 (2011), each of which is incorporated by reference in its entirety. The average distance between crosslinking points in the alginate gel was almost twice of that in the PEG (3.2 nm and 1.7 nm, respectively), allowing for more rapid diffusion of analytes within. Hence, when exposed to riboflavin at t=0 min, the fluorescent signal of the SWNT in the alginate gels decreased significantly, where the nanoparticles in the PEG hydrogel showed little to no response. The shorter diffusion time in alginate enables rapid signal modulation by analytes of similar hydrodynamic radius, where the PEG gel encapsulation used in this work impedes signal quenching which makes it less favorable for encapsulation. The two characteristic quenching times in the case of the alginate hydrogel system are attributed to the fast riboflavin-SWNT reaction and the slow diffusion rates, respectively. A rough estimation of riboflavin diffusion coefficient $D_R$ in solution ($3.23\times10^{-10}$ $m^2$ $s^{-1}$, See, Sen, F. et al. Observation of Oscillatory Surface Reactions of Riboflavin, Trolox, and Singlet Oxygen Using Single Carbon Nanotube Fluorescence Spectroscopy. *ACS Nano* 6, 10632-10645, doi:10.1021/nn303716n (2012), which is incorporated by reference in its entirety) results in an upper bound of the diffusion time of 8 hours for 3 mm gel thickness, in agreement with the experimental results.

Figure 18D:
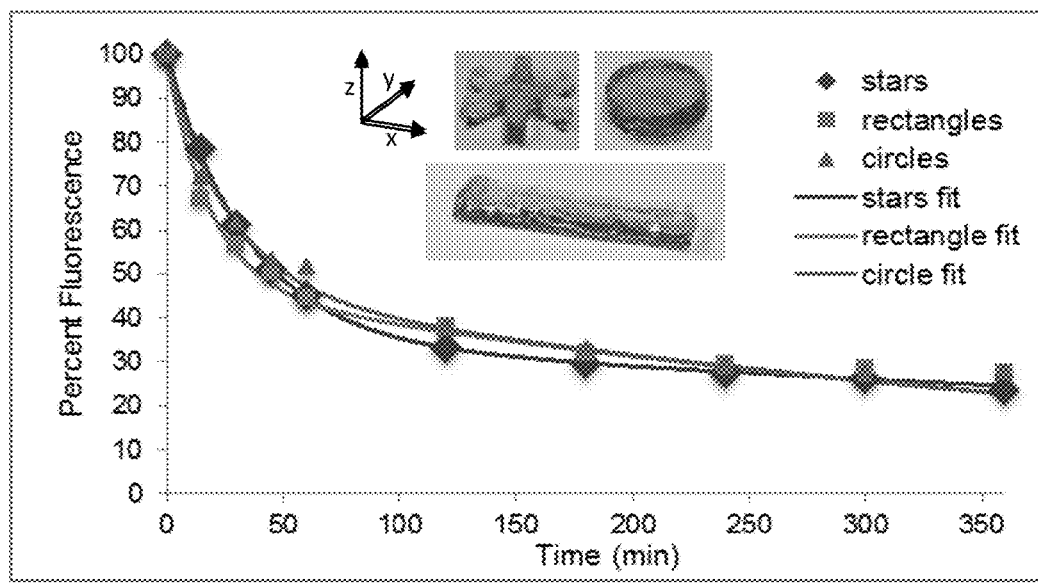

Since both types of hydrogels demonstrate diffusion limited quenching responses, it was explored whether the geometrical properties of the gels can modulate the diffusion rate. However, the results indicate that changing the size and shape of the lateral dimension of the hydrogel, while keeping thickness constant, have only little effect on the quenching rate. Since the thickness of the gels was small relative to their diameter, the diffusion was dominated by the transverse component along the z-axis (FIGS. 18C and 18D). In addition, the shape, and therefore the surface area of the gel, was also found to have only minor effect in terms of quenching rates.

Both the alginate and PEG properties can be adjusted by changing the final concentration of the gel solution prior to crosslinking, and the specification of the gel must be tailored according to the analyte properties, and the detection time scale required. Modulation of the hydrogel pore size can be exploited for increased specificity by excluding molecules with lower diffusion rates, or higher hydrodynamic radius, than the analyte of interest.

Long term stability experiments significantly manifested longer chemical stability of the alginate gels compared to the PEG hydrogel, rendering them more appropriate for long term in vivo sensing and detection as well as affording the opportunity to make larger batches of hydrogels, decreasing production time and sample variability. The impaired stability of the PEG hydrogel relative to the alginate can be partly attributed to the significant UV absorption of the nanoparticles used in this study which can interfere with the photo-induced crosslinking of the PEG hydrogel utilizing this part of the spectrum. Since hydrogels encapsulating lower nanoparticle concentrations were shown to exhibit longer shelf life, it is preferable to use the lowest possible concentration that would still allow for a reliable detection of the signal, for long term applications.

The $(GT)_{15}$-SWNT (SEQ ID NO: 2) encapsulated in PEG and alginate hydrogels can be imaged within tissue in the nIR array and in the whole animal imaging systems for more than 4 mm in depth, depending on the exposure time, where the signal reduces to half of its maximal value after approximately 0.55 mm and 0.52 nm for PEG and alginate, respectively. Hence, subcutaneous or intraperitoneal implants of such constructs can be optically imaged by an external device in a noninvasive manner, enabling real time in vivo detection and sensing of analytes. For animal research purposes, such platform could potentially reduce the number of animals sacrificed for tumor harvesting, for example, by monitoring biomarkers of interest externally. One must take into account that different tissues, such as bone or fat, may have higher or lower detection depth limits than skeletal muscle tissue which was the object of this study. The detection of a hydrogel through alternate tissues is predicted to vary depending on tissue transparency and organization, which could alter light scattering and absorption properties.

The maximum detection depth for our specific detection time, power output and signal capture, which was found to be of the order of magnitude of 4-5 mm, is a limiting factor for deep tissue detection especially in large animals or humans, but possible setup optimization could extend the working range. By increasing the intensity of the excitation laser from 14 mW, within biosafety restrictions that are specific for laser wavelength and tissue pigmentation, the enhanced emission signal could penetrate thicker tissue. An extension of the time over which the signal is acquired and more advanced emission signal collection techniques would also extend the viable detection depth for the sensors. Alternately, the detection depth limit could be overcome with a minimally invasive procedure of surgically inserting an endoscopic optical fiber to the implementation region to transfer the excitation and detection light channels.

Finally, the detection of the nanoparticle fluorescent signal was demonstrated when encapsulated in either PEG or alginate hydrogels and implanted subcutaneously within a mouse. This confirms the fusibility of our hydrogel-sensor system to be used for in vivo sensing and detection applications This model, which was demonstrated with the $(GT)_{15}$ (SEQ ID NO: 2) DNA wrapped single walled carbon nanotubes, can be applied to other polymers that suspend SWNT and alter the sensor specificity as well as to any other fluorescent nanoparticles. Moreover, the exhaustive experimentation performed here give valuable tools for engineering such hydrogel encapsulated nIR fluorescent sensors, assessing their performance and predicting detection depth limit.

Nanoparticle sensor encapsulation within hydrogels can be a promising platform for in vivo detection applications. The hydrogel composition plays a crucial role in determining the fluorescent signal intensity and stability. In addition to the physical properties of the gel, the concentration of the fluorescent nanoparticle within the hydrogel effects signal detection limits, creating a template for incident specific sensor assays. Finally, the correlation between maximal tissue detection depth and fluorescence intensity of nanoparticle sensors has been demonstrated, providing a formula to determine the optimal gel parameters for in vivo use.

Materials and Methods

DNA Oligonucleotide Nanotube Suspension.

SWNT were suspended with $d(AAAT)_7$ (SEQ ID NO: 1) oligonucleotide using methods similar to the one published previously. Briefly, SWNT purchased from SouthWest NanoTechnologies (SG65i, tube diameter 0.77+/−0.02 nm, high aspect ratio of >1,000, carbon content of >95% by weight, >40% (6,5) chirality SWNT and >95% of SWNT are semiconducting) were suspended with a 28-base $(dAdA-dAdT)_7$ (SEQ ID NO: 1) sequence of ssDNA (Integrated DNA Technologies). DNA and SWNT were added in a 2:1 DNA:SWNT mass ratio to 0.1 M NaCl dissolved in nanopure water. Typical DNA concentrations used in this study were 2 mg mL$^{-1}$. The DNA/SWNT solutions were sonicated while on ice with a 3 mm probe tip sonicator (Cole Parmer) for 10 min at a power of 10 W, followed by bench top centrifugation for 180 min (Eppendorf Centrifuge 5415D) at 16,100 RCF. The top ⅔ of the supernatant was collected and the pellet discarded.

PEG-DNA Conjugation and PEG-DNA-CoMoCAT Suspension.

Figure 7:
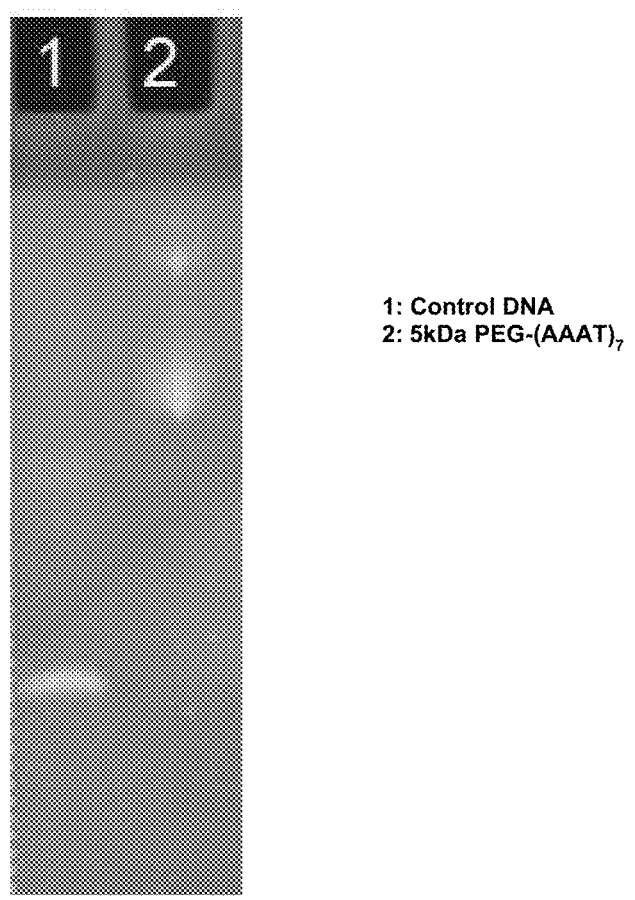
FIG. 7 is an image depicting gel electrophoresis of (AAAT)$_7$ (SEQ ID NO: 1) with and without PEG conjugation.

10 mM (10 µL of 0.5 M stock solution) TCEP (Tris(2-carboxyethyl)phosphine hydrochloride solution) (Sigma Aldrich) and 4.49 µL, 5' thiol-modified $d(AAAT)_7$ (SEQ ID NO: 1) (Integrated DNA Technologies) were mixed for 1 hour in 485.5 µL, water to break the disulfide bonds on DNA strands. Methoxy PEG (5 kDa) maleimide was dissolved at a concentration of 100 mg mL$^{-1}$ in PBS (1× phosphate buffered saline). Equal amounts of reduced DNA solution and mPEG-maleimide solution were then mixed for 20 min to complete PEG-DNA conjugation. The PEG-DNA conjugation was confirmed via gel electrophoresis (see FIG. 7). Suspension of SWNT with PEG-DNA followed a similar procedure as above. Briefly, 1 mg SWNT were combined with 1 mL PEG-DNA solution followed by sonication on ice with a 3 mm probe tip sonicator (Cole Parmer) for 40 min at 10 W. The resulting solution was centrifuged for 180 min (Eppendorf Centrifuge 5415D) at 16,100 RCF with the top ⅔ of supernatant collected and the pellet discarded. After centrifugation, free PEG-DNA was removed using centrifugal filtration (Amicon Ultra-4 100K Centrifugal Filter Units) with the solvent replaced by nanopure water. Centrifugal filtration was performed 4× to completely remove all residual DNA.

Alginate-$(AAAT)_7$-SWNT (SEQ ID NO:1) Preparation.

$(AAAT)_7$-SWNT (SEQ ID NO: 1) was mixed with 2% PRONOVA SLM 20 alginate (NovaMatrix) dissolved in normal saline and placed within a 1 cm glass bottom petri dish (MatTek). The alginate was cross-linked with an excess of 0.1 M barium chloride. Samples were rinsed with normal saline prior to implantation.

PAAm-$(AAAT)_7$-SWNT (SEQ ID NO: 1) Preparation.

$(AAAT)_7$-SWNT (SEQ ID NO: 1) was cast in a 3% T 5% C polyacrylamide hydrogel (PAAm) at a concentration of 1.5 mg mL$^{-1}$. The hydrogel polymerization was initiated with 1% by volume 100 mg mL$^{-1}$ ammonium persulfate initiator and the radical reaction was stabilized with 1% by volume Tetramethylethylenediamine. After crosslinking, the hydrogel was soaked in PBS to allow for maximum swelling and equilibrate the SWNT pH with the test buffers.

Screening of $(AAAT)_7$-SWNT (SEQ ID NO: 1), PEG-$(AAAT)_7$-SWNT (SEQ ID NO: 1) and Alginate-$(AAAT)_7$-SWNT (SEQ ID NO: 1) Against Other Reactive Oxygen and Nitrogen Species.

Sodium peroxynitrite and Angeli's salt were purchased from Cayman Chemical. Other chemicals used in the experiments were purchased from Sigma. Stock solutions of $NO_2^-$, $NO_3^-$, $H_2O_2$, and $ClO^-$ were prepared by dissolving them in water at 6 mM; Angeli's salt and $ONOO^-$ were dissolved at 6 mM in solutions of 0.3 M NaOH and 0.01 M NaOH, respectively. $O_2^-$ was prepared following a procedure in the literature.[41] Briefly, excess $KO_2$ was mixed with DMSO, vortexed and then centrifuged to remove the pellet. The resultant supernatant yields a stock solution of 3.6 mM $O_2^-$. SWNT solutions were diluted to 2 mg L$^{-1}$ in 50 mM PBS, pH 7.4. While monitoring SWNT fluorescence using a custom built near infrared (nIR) fluorescent microscope (described later), analyte solutions were added such that the final concentration was 60 µM and the SWNT fluorescent response was monitored for 10 min. Hydroxyl radicals were generated using Fenton's reaction, where $H_2O_2$ and $FeSO_4$ (60/0.6, 300/3, and 1000/10 µM as final concentration) were added into the SWNT solution. The SWNT fluorescent response was monitored for the first 10 minutes, and 12 hours after reagent addition. Singlet oxygen was generated using rose bengal using a similar procedure reported previously.[4,42] In brief, 60 µM of rose bengal was added to the SWNT solution (2 mg L$^{-1}$) and was excited at 560 nm to generate singlet oxygen. The SWNT fluorescence response at each minute was recorded by rapidly switching the excitation source to a 785 nm laser for 3 s. After 10 min the 560 nm excitation source was turned off and three additional spectra were taken every minute using 785 nm laser.

NO Solution.

Saturated NO solution was prepared using a method similar to that reported previously.[6] In brief, 3 mL of PBS was introduced into a 5 mL round-bottom flask and sealed with a septum with an inlet and an outlet needle. Argon gas (Airgas) was bubbled into the PBS for 2 h to remove dissolved oxygen NO gas (99.99%, Electronicfluorocarbons) was then bubbled for 20 min at an outlet pressure of 2 psi. The final NO concentration was determined using the horseradish peroxidase assay.[43,44]

nIR Fluorescence for Quenching and Signal Recovery.

SWNT nIR fluorescence spectra for $(AAAT)_7$-SWNT (SEQ ID NO: 1), PEG-$(AAAT)_7$-SWNT (SEQ ID NO: 1) and alginate-$(AAAT)_7$-SWNT (SEQ ID NO: 1) were measured via a custom built near infrared fluorescence microscope. In brief, a Zeiss AxioVision inverted microscope was coupled to a Princeton Instruments InGaAs 1-D array detector through a PI-Acton SP150 spectrograph. SWNT solutions are excited using a 785 nm photodiode (B&W Tek Inc.) with the resultant fluorescence collected by the microscope and coupled optics. NO quenching experiments were conducted as follows. A 150 µL sample of (AAAT)$_7$-SWNT (SEQ ID NO: 1) or PEG-(AAAT)$_7$-SWNT (SEQ ID NO: 1) (2.66 mg L$^{-1}$ solution for a 2 mg L$^{-1}$ final concentration after NO was added) was placed in a 96-well plate, excited with a 785 nm photodiode, and spectra were recorded every second 10 seconds. A 120 µM NO solution was added to the well (creating a 30 µM NO concentration in the well) and sample collection was continued for 30 minutes. Similarly, a 150 µL alginate-(AAAT)$_7$-SWNT (SEQ ID NO: 1) gel (25 mg L$^{-1}$) was placed in a 96-well plate and excited with a 785 nm photodiode with fluorescence spectra recorded for almost 45 hours following NO addition.

nIR Fluorescence Quenching of PAAm-(AAAT)$_7$-SWNT (SEQ ID NO: 1).

A 5 µL PAAm-(AAAT)$_7$-SWNT (SEQ ID NO: 1) (1.5 mg mL$^{-1}$) gel was placed in a glass well on a custom tabletop detector. The sample was excited at 565 nm and data was collected for the (6,5) SWNT emission peak of 990 nm 30 minutes following the addition of NO.

Subcutaneous Gel Implantation.

Mice were anesthetized with up to 5% isoflurane gas for the entirety of the study. Sterile, no touch technique was used for gel placement. Animals were covered with sterile drape and a small, less than 1 cm, incision was made and blunt dissection of skin from muscle was performed. Following baseline imaging of the alginate gel it was inserted and immobilized by nylon sutures or surgical glue application. The animal was then imaged (Maestro™ Cambridge Research & Instrumentation) and placed under a heating lamp to awake. Animals were monitored and imaged for the duration of the study and sacrificed with $CO_2$ for histological analysis at pre-determined time points.

Imaging with CRi's Maestro™.

In vivo imaging was performed on the Cambridge Research & Instrumentation's Maestro instrument. The Maestro contains a liquid crystal tuning element that allows transmitted light to be electronically tuned. The liquid crystal filter utilized in this study has a maximum wavelength range of 650-1050 nm and a 40 nm bandpass. Maestro software looks at the spectral emission wavelengths of the signal, background and autofluorescence and separates these three components (FIG. 1D) to allow for analysis of the signal of interest. An emission window from 950 to 1050 nm with a 10 nm step size and 20 second reading at each step was used for this study.

Histology.

Tissue samples were fixed overnight in 10% neutral-buffered formalin and sent to the Division of Comparative Medicine (Massachusetts Institute of Technology) for routine processing and paraffin embedding. Four-µm-thick sections were stained with hematoxylin and eosin (H&E) for microscopic examination by a board-certified pathologist (N.P.) who was blinded to treatment groups.

Agarose Gel Preparation.

Analytical gel electrophoresis was carried out in a 0.75% DNA grade high melt agarose gel in TBE buffer using a Powerpac Basic (Bio-Rad Laboratories) power supply at 200 V for 1 hour. (AAAT)$_7$-SWNT (SEQ ID NO: 1) and PEG-(AAAT)$_7$-SWNT (SEQ ID NO: 1) dispersions were mixed with Fetal Bovine Serum (FBS) and Tris-borate-EDTA (TBE) buffer (50 mM Tris-borate, 1 mM Na-EDTA, pH 8.4), and then loaded in separate wells in an electrophoresis gel after being supplemented with glycerol. The spatial position of SWNT in the gel was measured using the custom-built nIR fluorescent microscope. The gel was held on an automated x-y translation stage that moved 1 mm between every spectrum taken. This produced spatially parsed sets of nIR spectra over the length of the gel.

PEG-(AAAT)$_7$-SWNT (SEQ ID NO: 1) Injection for SWNT Localization.

Mice were sedated with up to 5% isoflurane gas for the entirety of the study. Freshly prepared PEG-(AAAT)$_7$-SWNT (SEQ ID NO: 1) was diluted to 50 mg L$^{-1}$ in normal saline, thoroughly mixed and injected (200 µL) into the mouse's tail vein with a 0.3 cc 29 gauge 0.5 inch insulin syringe. Mice were then sacrificed through $CO_2$ administration at the appropriate time point (0, 5, 15, 30, 60 or 120 min post injection) immediately followed by necropsy and sample imaging. Blood was collected through cardiac puncture and urine collected from the bladder, followed by tail, lung, liver and kidney harvest. Fluids and tissues were immediately imaged (Maestro™ Cambridge Research & Instrumentation), followed by histology and/or Raman analysis.

Raman Detection for SWNT Localization.

Raman scattering measurements were performed using a LabRam-IR (jobin Yvon Horiba) Raman microscope. Samples were excited with a 633 nm photodiode and focused onto the sample with a 10× objective. Scattered light was collected in a 180° configuration and focused onto a Si CCD camera. The excitation power at the sample was 12.6 mW having a final power density of ~550 kW cm$^{-2}$.

PEG-(AAAT)$_7$-SWNT (SEQ ID NO: 1) Injection for Detection of Inflammation.

Figure 9:
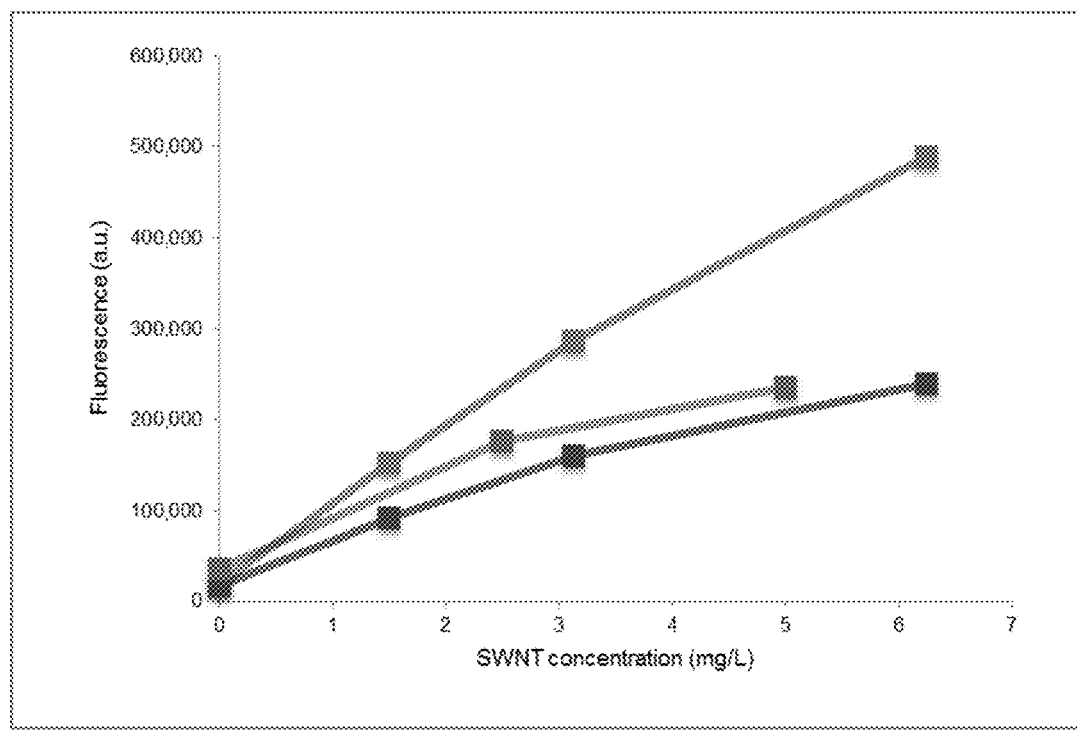
FIG. 9 is a graph depicting linear relationship between fluorescence intensity and SWNT concentration.

SJL mice (Charles River) were separated into two groups; (1) inflamed, receiving 1*10$^6$ RcsX cells in 200 µL saline through IP injection, and (2) non-inflamed, receiving an IP injection of 200 µL saline. After 12 days mice were sedated with up to 5% isoflurane gas and 200 µL of freshly prepared PEG-(AAAT)$_7$-SWNT (SEQ ID NO: 1), diluted to 50 mg L$^{-1}$ in normal saline, was injected into the tail vein with a 0.3 cc 29 gauge 0.5 inch insulin syringe. After 30 minutes mice were opened to expose their liver, imaged using the Cri Maestro, and then immediately sacrificed through $CO_2$ administration. Necropsy and tissue harvest (liver, lung, kidney, and spleen) was promptly performed, followed by tissue imaging (Maestro™ Cambridge Research & Instrumentation) and fixture for histology (to ensure inflammation and health of inflamed and non-inflamed mice, FIG. 9). FIG. 9 shows Quantification of (AAAT)$_7$-SWNT (SEQ ID NO: 1) (red), PEG-(AAAT)$_7$-SWNT (SEQ ID NO: 1) (blue) and Alginate-(AAAT)$_7$-SWNT (SEQ ID NO: 1) (green) fluorescence versus concentration. (n=3).

Gel Mold.

A mold for cross-linking the gels was created by cutting a 3.175 mm thick piece of silicone (HT-6240 Transparent 0.125" performance solid silicone, Rogers Corporation) with a water jet. The shapes chosen for the mold were designed to alter surface area of the gel while keeping the total volume constant.

Alginate-(GT)$_B$-SWNT (SEQ ID NO: 2) Preparation.

(GT)$_{15}$-SWNT (SEQ ID NO: 2) suspension was mixed with 2% PRONOVA SLM 20 alginate (NovaMatrix) dissolved in normal saline and pipetted into a specially cut mold (described above), with dialysis tubing (10,000 MWCO) stretched across the bottom, that was elevated 2 mm from the bottom of a basin. The alginate was cross-linked with an excess of 0.1 M barium chloride ($BaCl_2$) that was added to the basin without covering the top of the mold, for 24 hours. Samples were then transferred to a 0.1 M $BaCl_2$ bath until testing.

PEG-$(GT)_{15}$-SWNT (SEQ ID NO: 2) Preparation.

$(GT)_{15}$-SWNT (SEQ ID NO: 2) suspension was mixed with a solution of Polyethylene glycol-diacrylate (700 g/mol, Sigma-Aldrich, 1.12 g mL$^{-1}$ at 25° C.), 2-hydroxy-4'-(2-hydroxyethoxy)-2-methylpropiophenone (7 mg mL$^{-1}$, Sigma-Aldrich) and water in a 1:0.05:0.95 volume ratio and pipetted into a specially cut mold (described above), with tape adhered to the bottom. The PEG was cross-linked by exposure to UV-B light (365 nm) for 15 minutes and transferred to a water bath until testing. See, Kruss, S., Erpenbeck, L., Schon, M. P. & Spatz, J. P. Circular, nanostructured and biofunctionalized hydrogel microchannels for dynamic cell adhesion studies. *Lab Chip* 12, 3285-3289, doi:10.1039/c21c40611j (2012), and Kruss, S., Srot, V., van Aken, P. A. & Spatz, J. P. Au—Ag hybrid nanoparticle patterns of tunable size and density on glass and polymeric supports. *Langmuir* 28, 1562-1568, doi:10.1021/la204395d (2012), each of which is incorporated by reference in its entirety.

Optical Characterization of SWNT Gels.

Alginate-$(GT)_{15}$-SWNT (SEQ ID NO: 2) and PEG-$(GT)_{15}$-SWNT (SEQ ID NO: 2) solutions were prepared as described above, where 150 µl aliquots of the alginate solution were casted into 2 kDa molecular weight cutoff slide-A-lyzer mini dialysis units and placed in a 0.1 M barium chloride bath for crosslinking, and 150 µl aliquots of the PEG solution were casted into a 4.5 mm in diameter and 9 mm in height tubing for crosslinking by UV-B light. The crosslinked PEG and alginate hydrogel plugs were placed in a 96-well plate in 150 µl of water and 150 µl of 0.1 M barium chloride in each well, respectively, and were allowed to equilibrate for 24 hours before testing.

Fluorescent emission of the SWTN hydrogels was measured in a custom built near infrared fluorescence microscope (nIR array). In brief, a Zeiss AxioVision inverted microscope was coupled to a Princeton Instruments InGaAs 1-D array detector through a PI-Acton SP150 spectrograph. SWNT solutions are excited using a 785 nm, 150 mW (80 mW on the sample plane) photodiode laser (B&W Tek Inc.) with the resultant fluorescence collected by the microscope with x20 objective, and coupled optics.

Rheological Characterization of SWNT Gels.

Alginate-$(GT)_{15}$-SWNT (SEQ ID NO: 2) and PEG-$(GT)_{15}$-SWNT (SEQ ID NO: 2) solutions were prepared as described above, where 1.25 ml aliquots ware casted for crosslinking in a 20 mm diameter ring mold, forming a hydrogel disk. Rheological characterization was performed on an AR2000 Rheometer (TA Instruments) with a 20 mm parallel steel plate geometry. An adhesive sand paper was used to ensure proper and constant contact of the top and bottom surfaces of the gel. Initial strain sweep was done with 1 Hz frequency and followed by a frequency sweep with 0.1% and 0.01% strain for the alginate and PEG gels respectively.

Tissue Imaging.

In vivo imaging was performed on a whole animal imaging platform described previously (see, Iverson, N. M. et al. In Vivo Biosensing Via Tissue Localizable Near Infrared Fluorescent Single Walled Carbon Nanotubes. *Nature Nanotechnology* 8, 873-880 (2013), which is incorporated by reference in its entirety) using a liquid crystal tunable band pass filter and a CCD camera (Maestro™ CRi). Filter wavelengths utilized in this study ranged from 650 to 1050 nm at a 40 nm bandpass. Spectral 2D image-wavelength stacks were background subtracted from any autofluorescence segregated into three components as described previously (see, Iverson, Nanotechnology, 2013). Specific images were collected with an emission window from 950 to 1050 nm at 10 nm increments and 20 second integration times at each step.

SWNT Fluorescence Quenching.

SWNT nIR fluorescence spectra for PEG-$(GT)_{15}$-SWNT (SEQ ID NO: 2) and alginate-$(GT)_{15}$-SWNT (SEQ ID NO: 2) were measured in a 96-well plate on the nIR microscope described previously (see, Iverson, Nanotechnology, 2013). The $(GT)_{15}$-SWNT (SEQ ID NO: 2) samples of 150 µL were prepared with concentrations of 2, 5, 10, and 25 mg L$^{-1}$ and tested within a 96-well plate as well. Model quenching experiments were conducted by adding 1.5 µL of 10 mM riboflavin (Sigma) to each well, comparing to control samples to which 1.5 µL of water was added. The samples were incubated for 1 hour in room temperature on a shaker and then Imaged in the nIR array.

Photobleaching of SWNT Gels.

PEG-$(GT)_{15}$-SWNT (SEQ ID NO: 2) and alginate-$(GT)_{15}$-SWNT (SEQ ID NO: 2) were placed on a wetted piece of filter paper (BioRad mini Trans-Blot), exposed to a 651 nm 14 mW laser and imaged by the animal imaging system every 5 minutes for a 4 hour interval. The samples were continuously exposed to the laser irradiation for the entire course of the photobleaching study.

Long Term Stability of SWNT Gels.

PEG-$(GT)_{15}$-SWNT (SEQ ID NO: 2) and alginate-$(GT)_{15}$-SWNT (SEQ ID NO: 2) were analyzed for 60-90 days on the nIR array and whole animal imaging systems. Gels were imaged as described above and stored in their buffer solutions (water and $BaCl_2$ for PEG and alginate gels respectively) at 25° C. between imaging.

Tissue Depth Detection with Phantom Tissue.

Tissue phantom (chicken breast) was sectioned to thicknesses of 2, 4, 6, 8 or 10 mm with a uniform radius of 2 cm. A 1 cm thick section of tissue was placed on the whole animal imaging platform, with a gel sample centered on the tissue and sample tissue of specified thickness was placed on top of this stack for imaging. This was repeated with three different gels and three different sample tissues for each thickness tested. For the nIR array imaging system, slices of various thicknesses of chicken breast tissue were placed on a microscope slide, and the gel plugs were placed on top on the tissue sample. The exposure times for the PEG hydrogels were 9, 14, 16, 24, and 36 seconds for 0, 1, 2, 3, and 4 mm thick samples respectively, and 4, 6, 8, 12, and 20 seconds for the alginate gels, for the same chicken breast samples. The absorption of the chicken breast tissue was measured using a UV-Visible-nIR spectrophotometer (UV-3101 PC Shimadzu).

Mathematical Formulas Used to Deconvolute Raw Data

The image data provided by Maestro is in the form of a 3D image stack, with each layer being a regular 2D image of the number of detected photons at a particular wavelength. These images are scaled by maestro before processing. Prior to analysis, the image stacks are deconvoluted to provide images that represent the relative contribution of the nanotubes, the background tissue, and the autofluorescence noise. This is done by doing a least squares minimization of a linear fit of the fluorescence spectrum. The following model was used:

$$\text{Measured} = l_x, \text{Model} = B \cdot b_x + N \cdot n_x + A \cdot a_x$$

Where $l_x$ is the measured spectrum for a particular pixel (normalized to 1), $b_x$ and $n_x$ are the background and nanotube spectra respectively, and $a_x$ is a white noise autofluorescence spectrum. The $b_x$ and $n_x$ spectra are obtained directly from a Maestro .csl file. These files were initially calculated by the Maestro software through singular value decomposition or other user assisted method. The $a_x$ spectrum is constant with respect to x. All of the spectra are normalized to have an average value of 1. The following system of equations defining the minimization is solved for each pixel with positive coefficients:

$$\frac{\partial \sum_x (i_x - (Bb_x + Nn_x + Aa_x))^2}{\partial B} = 0,$$

$$\frac{\partial \sum_x (i_x - (Bb_x + Nn_x + Aa_x))^2}{\partial A} = 0,$$

$$\frac{\partial \sum_x (i_x - (Bb_x + Nn_x + Aa_x))^2}{\partial N} = 0$$

Subsequently, black on white region of interest images are created to define an area encompassing the livers, and subsequent data analysis is done on these regions.

For each pixel, to find the linear combination of fluorescent spectra that provide the best fit to the measured spectrum, the following sum should be minimized:

$$\sum_x (Bb_x + Nn_x + Aa_x - i_x)^2$$

Where $b_x, n_x, a_x, i_x$ are the spectra for background, nanotubes, autofluorescence, and image normalized to have an average of 1. A, B, N are the linear coefficients. However, since it is assumed that nanotubes, background, and autofluorescence are the only sources of fluorescence, there are the following constraints:

$$A+B+N=1, \; 0 \leq A,B,N \leq 1$$

These constraints can be used to simplify the problem. Now the following should be minimized:

$$\sum_x (Bb_x + Nn_x + (1-N-B)a_x - i_x)^2 = \sum_x (B(b_x - a_x) + N(n_x - a_x) - (i_x - a_x))^2$$

Taking the partial derivative with respect to B and N and equating to zero gives us:

$$\sum_x (b_x - a_x)(B(b_x - a_x) + N(n_x - a_x) - (i_x - a_x)) = 0$$

$$\sum_x (n_x - a_x)(B(b_x - a_x) + N(n_x - a_x) - (i_x - a_x)) = 0$$

Solving these two equations yields:

$$N = \frac{\sum_x (b_x - a_x)(i_x - a_x) \sum_x (n_x - a_x)(b_x - a_x) - \sum_x (n_x - a_x)(i_x - a_x) \sum_x (b_x - a_x)^2}{\left(\sum_x (n_x - a_x)(b_x - a_x)\right)^2 - \sum_x (b_x - a_x)^2 \sum_x (n_x - a_x)^2}$$

$$B = \frac{\sum_x (n_x - a_x)(i_x - a_x) \sum_x (n_x - a_x)(b_x - a_x) - \sum_x (b_x - a_x)(i_x - a_x) \sum_x (n_x - a_x)^2}{\left(\sum_x (n_x - a_x)(b_x - a_x)\right)^2 - \sum_x (b_x - a_x)^2 \sum_x (n_x - a_x)^2}$$

$$A = 1 - N - B$$

This allows us to recalculate the following values:

$$constDenom = \left(\sum_x (n_x - a_x)(b_x - a_x)\right)^2 - \sum_x (b_x - a_x)^2 \sum_x (n_x - a_x)^2$$

$$sumsquaredNanoAutoDif = \sum_x (n_x - a_x)^2$$

$$sumsquaredBackAutoDif = \sum_x (b_x - a_x)^2$$

$$sumcrossNanoBack = \sum_x (n_x - a_x)(b_x - a_x)$$

And also the following vectors:

vecNanoAutoDif=$(n_x-a_x)$ vecBackAutoDif=$(b_x-a_x)$

However, because of the non-negativity constraint, if any of the calculated constants is negative, it is taken to be 0, and the calculation is redone (using a similar minimization and recalculated constants and vectors for optimization). If this results in another value being negative, both are set to 0 and the remaining value becomes 1 by default.

This problem was explicitly solved for 3 sources, but it is possible to be solved for as many sources as is desired, so long as there are more wavelengths (x) in the spectrum than there are sources (otherwise the problem doesn't have a unique solution). The constraints of normegativity and summation to one must still be observed.

Matlab Code used to deconvolute raw data

```
function Unmixing_Program_v1
%
% Code to unmix a maestro cube file into a background and
% nanotube fluorescence image. Calculates maximum, total, and average
% fluorescence for a particular region of interest (ROI).
% Create a heat map of fluorescent signal.
```

| Matlab Code used to deconvolute raw data |
| --- |

```
%
%Default Size for the image.
ri = 520; %number of pixel rows
ci = 696; %number of pixel columns
n = 11; %spectrum size
% Read in the spectrum file.
[filename,PathName] = uigetfile({'*.csl', 'Maestro Spectrum Files (*.csl)'}, 'Choose a
Spectral Library');
Spectra = parse_maestro(strcat(PathName, filename), n);
Library = Spectra(:,2); %Nanotube Spectrum
Background = Spectra(:,3); %Background Spectrum
%Precompute algorithm constants and vectors.
normLibrary = Library/mean(Library);
normBackground = Background/mean(Background);
autoSpecConst = 1;
%Constants for no Autofluorescence
vecNanoBackDif = normLibrary - normBackground;
sumsquaredNanoBackDif = sum(vecNanoBackDif.^2);
%Constants for Monotone Autofluorescence
vecNanoAutoDif = normLibrary - autoSpecConst;
vecBackAutoDif = normBackground - autoSpecConst;
sumsquaredNanoAutoDif = sum(vecNanoAutoDif.^2);
sumsquaredBackAutoDif = sum(vecBackAutoDif.^2);
sumcrossNanoBack = sum(vecNanoAutoDif.*vecBackAutoDif);
constDenom = sumsquaredNanoAutoDif*sumsquaredBackAutoDif -
sumcrossNanoBack^2;
Reply = 'Yes';
while(strcmp(Reply,'Yes')==1)
    %Chose a Cube File
    [filename,PathName] = uigetfile({'*.im3', 'Maestro Cube Files (*.im3)'}, 'Choose a
Cube File to Unmix');
    file_root = filename(1:(length(filename)-4));
    SpecData = parseCube3(strcat(PathName, filename));
    SpecData = double(SpecData);
    %Create Arrays for Background and Nanotube Images
    BackgroundImage = zeros(ri,ci);
    NanotubeImage = zeros(ri,ci);
    AutofluorescenceImage = zeros(ri,ci);
    totalValue = 1;
    for i = 1:ri
        rowStart = (i-1)*ci*n;
        for j = 1:ci
            vec = SpecData((rowStart+(j-1)*n+1):(rowStart+j*n));
            SumVec = sum(vec);
            normvec = (vec.*n)./SumVec;
            totalValue = SumVec./255;
            DifVec = normvec - autoSpecConst;
            sumVecNano = sum(DifVec.*vecNanoAutoDif);
            sumVecBack = sum(DifVec.*vecBackAutoDif);
            %General Case
            BackgroundValue = (sumsquaredNanoAutoDif*sumVecBack -
sumVecNano*sumcrossNanoBack)/constDenom;
            NanotubeValue = (sumsquaredBackAutoDif*sumVecNano -
sumVecBack*sumcrossNanoBack)/constDenom;
            BackNanoTotal = BackgroundValue + NanotubeValue;
            %Specific Cases to guarantee non-negativity
            if(BackNanoTotal>1)
                sumVecBoth = sum((normvec - normBackground).*vecNanoBackDif);
                NanotubeValue = sumVecBoth/sumsquaredNanoBackDif;
                if NanotubeValue < 0
                    BackgroundImage(i,j) = totalValue;
                elseif NanotubeValue > 1
                    NanotubeImage(i,j) = totalValue;
                else
                    NanotubeImage(i,j) = totalValue.*NanotubeValue;
                    BackgroundImage(i,j) = (1 - NanotubeValue).*totalValue;
                end
            elseif(BackgroundValue < 0)
                NanotubeValue = sumVecNano/sumsquaredNanoAutoDif;
                if NanotubeValue < 0
                    AutofluorescenceImage(i,j) = totalValue;
                elseif NanotubeValue > 1
                    NanotubeImage(i,j) = totalValue;
                else
                    NanotubeImage(i,j) = totalValue.*NanotubeValue;
                    AutofluorescenceImage(i,j) = (1 - NanotubeValue).*totalValue;
                end
```

| Matlab Code used to deconvolute raw data |
|---|

```
        elseif(NanotubeValue < 0)
           BackgroundValue = sumVecBack/sumsquaredBackAutoDif;
           if BackgroundValue < 0
              AutofluorescenceImage(i,j) = totalValue;
           elseif BackgroundValue > 1
              BackgroundImage(i,j) = totalValue;
           else
              BackgroundImage(i,j) = totalValue.* BackgroundValue;
              AutofluorescenceImage(i,j) = (1 - BackgroundValue).*totalValue;
           end
        else
           NanotubeImage(i,j) = NanotubeValue.*totalValue;
           BackgroundImage(i,j) = BackgroundValue.*totalValue;
           AutofluorescenceImage(i,j) = (1 - BackNanoTotal).*totalValue;
        end
     end
  end
  %Fixing NaN values
  NanotubeImage(isnan(NanotubeImage)) = 0;
  BackgroundImage(isnan(BackgroundImage)) = 0;
  AutofluorescenceImage(isnan(AutofluorescenceImage)) = 0;
  %Save resulting images in folder containing cube file
  imwrite(BackgroundImage,strcat(PathName, file_root,
'_Unmixed_Background.tif'),'tif');
  imwrite(NanotubeImage,strcat(PathName, file_root, '_Unmixed_Nanotube.tif'), 'tif');
  imwrite(AutofluorescenceImage,strcat(PathName,file_root,
'_Unmixed_Autofluorescence.tif'), 'tif');
  %Define the colorscheme for the heatmap
  col = colormap(jet(256));
  col(54:192, :) = colormap(jet(139));
  col(1:53,1:3) = 0;
  col(193:256,1) = 1;
  col(193:256,2) = 0;
  col = colormap(col);
  imwrite(NanotubeImage*255, col, strcat(PathName, file_root,
'_Unmixed_Nanotube_Heatmap.tif'),'tif'); %Save heatmap
  close all;
  %*******************************
  %Beginning of the Image Analysis
  %*******************************
  %Choose Region of Interest file
  [filename2,PathName2] = uigetfile({'*.tif', 'ROI Image File (.tif)'}, 'Choose ROI');
  %Convert Image to usable ROI matrix
  ROI = 255-imread(strcat(PathName2, filename2));
  ROI = ROI(:,:,1)>0;
  RegionSize = sum(sum(ROI));
  ROIbackground = (ROI-1).*(-1);
  %Data values to be calculated(within ROI):
  %Maximum Fluorescence, Total Fluorescence
  %Average Fluorescence, Standard Deviation
  Export = zeros(1,4); %matrix where they are stored
  MaximumValue = max(max(ROI.*NanotubeImage))*255;
  TotalCount = 0;
  for i = 1:ri
     for j = 1:ci
        if(ROI(i, j)== 1)
           TotalCount = TotalCount + NanotubeImage(i, j);
        end
     end
  end
  TotalCount = TotalCount*255;
  AverageCount = TotalCount./RegionSize;
  StDevCount = 0;
  for i = 1:ri
     for j = 1:ci
        if(ROI(i, j)== 1)
           StDevCount = StDevCount + (NanotubeImage(i, j).*255 - AverageCount).^2;
        end
     end
  end
  StandardDeviation = sqrt(StDevCount./RegionSize);
  Export = [MaximumValue TotalCount AverageCount StandardDeviation];
  %save the data to be easily viewable in excel
  csvwrite(strcat(PathName,file_root, '_Data.csv') , Export);
  %Prompt user to repeat
  Reply = questdlg('Unmix Another Cube?','','Yes','No','Yes');
end
```

| Matlab Code used to deconvolute raw data |
|---|
| function outData = parse_maestro(filename, count)<br>  % Function to import spectral values from a .csl file.<br>  % Intended for two spectra.<br>  % Open and get the file handle of the specified Maestro file<br>  fileid = fopen(filename);<br>  % Read file as string to get 'Wavelengths' and 'Magnitudes' indices<br>  A = fscanf(fileid, '%c');<br>  waveLoc = regexp(A, 'Wavelengths@');<br>  magLoc = regexp(A, 'Magnitudes@');<br>  outData = zeros(count, 3);<br>  % Read the wavelengths<br>  fseek(fileid, waveLoc(1) + 26, −1);<br>  outData(:, 1) = fread(fileid, count, 'float32', 0, 'a');<br>  % Read the first set of magnitudes<br>  fseek(fileid, magLoc(1) + 25, −1);<br>  outData(:, 2) = fread(fileid, count, 'float32', 0, 'a');<br>  % Read the second set of magnitudes<br>  fseek(fileid, magLoc(2) + 25, −1);<br>  outData(:, 3) = fread(fileid, count, 'float32', 0, 'a');<br>  % Release the file handle<br>  fclose(fileid);<br>end<br>function returnImageStack = parseCube3( filename )<br>  % Function to extract a vector of fluorescence<br>  % values from an .im3 format file. To read larger<br>  % files, make the scan size larger.<br>  % Opens .im3 file and scans to find<br>  % the beginning of image data<br>  fileid = fopen(filename);<br>  fseek(fileid, 50000, −1);<br>  A = fscanf(fileid, '%c', 20000000); %scan size<br>  dataLoc = regexp(A, 'Dataú~y');<br>  dataLoc = dataLoc + 50000;<br>  fseek(fileid, dataLoc(1) + 27, −1);<br>  returnImageStack = fread(fileid, ri*ci*n, 'int16', 0);<br>  fclose(fileid);<br>end<br>end |

Other embodiments are within the scope of the following claims.

What is claimed is:

1. A nanosensor for detecting an analyte, comprising:
a substrate hydrogel arranged on a support;
a sensor hydrogel arranged on the substrate hydrogel;
a photoluminescent nanostructure embedded in the sensor hydrogel; and
a polymer interacting with the photoluminescent nanostructure,
wherein the polymer is ligated with the sensor hydrogel.

2. The nanosensor of claim 1, wherein the analyte has a molecule weight of less than 100 g/mol.

3. The nanosensor of claim 2, wherein the analyte is nitric oxide.

4. The nanosensor of claim 1, wherein the photoluminescent nanostructure comprises a carbon nanotube.

5. The nanosensor of claim 4, wherein the carbon nanotube is a single-walled carbon nanotube.

6. The nanosensor of claim 5, wherein the single-walled carbon nanotube is a semiconductive single-walled carbon nanotube.

7. The nanosensor of claim 1, wherein the polymer includes an oligonucleotide or a polynucleotide.

8. The nanosensor of claim 7, wherein the oligonucleotide includes $ds(AAAT)_7$ (SEQ ID NO: 1).

9. The nanosensor of claim 1, wherein the photoluminescent nanostructure emits near-infrared radiation in the absence of the analyte.

10. The nanosensor of claim 1, wherein the photoluminescent nanostructure emits near-infrared radiation in the presence of the analyte.

11. The nanosensor of claim 1, wherein the polymer includes polyvinyl alcohol, poly(acrylic acid), poly(ethylene oxide), poly(vinyl pyrrolidinone), poly(allyl amine), poly(2-vinylpyridine), or poly(maleic acid).

12. The nanosensor of claim 1, wherein the concentration of the analyte is less than 1 micromolar.

13. The nanosensor of claim 1, wherein the interaction between the analyte and the nanosensor includes an interaction between the analyte and the photoluminescent nanostructure.

14. The nanosensor of claim 1, wherein the substrate hydrogel includes alginate hydrogel.

15. The nanosensor of claim 1, wherein the sensor hydrogel includes alginate hydrogel.

16. The nanosensor of claim 1, wherein the polymer includes a copolymer of a hydrophilic polymer and an oligonucleotide.

17. The nanosensor of claim 16, wherein the hydrophilic polymer is poly(ethylene oxide).

18. The nanosensor of claim 16, wherein the oligonucleotide is $ds(AAAT)_7$ (SEQ ID NO: 1).

19. The nanosensor of claim 16, wherein the copolymer includes poly(ethylene oxide) and $ds(AAAT)_7$ (SEQ ID NO: 1).

20. The nanosensor of claim 1, wherein the substrate hydrogel includes polyethylene glycol.

21. The nanosensor of claim 1, wherein the sensor hydrogel includes polyethylene glycol.

22. A method of detecting an analyte in a subject, comprising:
introducing a sensor into a subject, wherein the sensor includes:
a substrate hydrogel arranged on a support;
a sensor hydrogel arranged on the substrate hydrogel;
a photoluminescent nanostructure embedded in the sensor hydrogel; and
a polymer interacting with the photoluminescent nanostructure, wherein the polymer is ligated with the sensor hydrogel; and
monitoring emission of radiation from the sensor in the subject.

23. The method of claim 22, further comprising detecting photoluminescence from the photoluminescent nanostructure.

24. The method of claim 22, wherein introducing the sensor includes injecting the sensor into a tissue of the subject.

25. The method of claim 22, wherein the substrate hydrogel includes alginate hydrogel.

26. The method of claim 22, wherein the sensor hydrogel includes alginate hydrogel.

27. The method of claim 22, wherein the analyte has a molecule weight of less than 100 g/mol.

28. The method of claim 27, wherein the analyte is nitric oxide.

29. The method of claim 22, wherein the photoluminescent nanostructure comprises a carbon nanotube.

30. The method of claim 29, wherein the carbon nanotube is a single-walled carbon nanotube.

31. The method of claim 30, wherein the single-walled carbon nanotube is a semiconductive single-walled carbon nanotube.

32. The method of claim 22, wherein the polymer includes an oligonucleotide or a polynucleotide.

33. The method of claim 32, wherein the oligonucleotide includes $ds(AAAT)_7$ (SEQ ID NO: 1).

34. The method of claim 22, wherein the polymer includes polyvinyl alcohol, poly(acrylic acid), poly(ethylene oxide), poly(vinyl pyrrolidinone), poly(allyl amine), poly(2-vinylpyridine), or poly(maleic acid).

35. The method of claim 22, wherein the polymer includes a copolymer of a hydrophilic polymer and an oligonucleotide.

36. The method of claim 35, wherein the hydrophilic polymer is poly(ethylene oxide).

37. The method of claim 35, wherein the oligonucleotide is $ds(AAAT)_7$ (SEQ ID NO: 1).

38. The method of claim 35, wherein the copolymer includes poly(ethylene oxide) and ds(AAAT)$_7$ (SEQ ID NO: 1).

39. The method of claim 22, wherein the photoluminescent nanostructure emits near-infrared radiation in the absence of the analyte.

40. The method of claim 22, wherein the photoluminescent nanostructure emits near-infrared radiation in the presence of the analyte.

41. The method of claim 22, wherein the concentration of the analyte is less than 1 micromolar.

42. The method of claim 22, wherein the substrate hydrogel includes polyethylene glycol.

43. The method of claim 22, wherein the sensor hydrogel includes polyethylene glycol.

* * * * *

```
                        SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaataaataa ataaataaat aaataaat                                           28

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgtgtgtgt gtgtgtgtgt gtgtgtgtgt                                         30

<210> SEQ ID NO 3
```

-continued

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 atatatat atatatatat atatatatat                                            30
```